(12) United States Patent
White et al.

(10) Patent No.: US 10,369,313 B2
(45) Date of Patent: Aug. 6, 2019

(54) AIRWAY ADAPTERS AND SUCTION CATHETER SYSTEMS

(71) Applicant: CareFusion 2200, Inc., San Diego, CA (US)

(72) Inventors: Dennis White, Yorba Linda, CA (US); Haojun Fu, Yorba Linda, CA (US); Sibgat Ulla, Placentia, CA (US); Ming Lu, Pasadena, CA (US); Christopher Varga, Laguna Hills, CA (US); Simon Jung, Placentia, CA (US); Charles Edward Beuchat, Trabuco Canyon, CA (US)

(73) Assignee: Vyaire Medical Consumables LLC, Yorba Linda, CA (US)

(*) Notice: Subject to any disclaimer, the term of this patent is extended or adjusted under 35 U.S.C. 154(b) by 898 days.

(21) Appl. No.: 14/821,438

(22) Filed: Aug. 7, 2015

(65) Prior Publication Data

US 2016/0038700 A1    Feb. 11, 2016

Related U.S. Application Data

(60) Provisional application No. 62/035,367, filed on Aug. 8, 2014, provisional application No. 62/035,366, filed
(Continued)

(51) Int. Cl.
*A61M 16/20* (2006.01)
*A61M 16/04* (2006.01)
*A61M 16/08* (2006.01)

(52) U.S. Cl.
CPC .... *A61M 16/0463* (2013.01); *A61M 16/0825* (2014.02); *A61M 16/0833* (2014.02);
(Continued)

(58) Field of Classification Search
CPC ...... A61M 16/0477; A61M 2039/2446; A61M 39/06; A61M 16/0816; A61M 16/0825;
(Continued)

(56) References Cited

U.S. PATENT DOCUMENTS 4,240,417 A    12/1980 Holever
4,416,273 A *  11/1983 Grimes ............. A61M 16/0463
                                              128/207.15
(Continued)

FOREIGN PATENT DOCUMENTS

CN    205181939 U    4/2016
JP    H6197953 A     1/1994
(Continued)

OTHER PUBLICATIONS

Invitation to Pay Fees and Partial Search Report for Application No. PCT/US2015/044244, dated Oct. 20, 2015, 9 pages.
(Continued)

*Primary Examiner* — Annette Dixon
(74) *Attorney, Agent, or Firm* — Morgan, Lewis & Bockius LLP

(57) ABSTRACT

Airway adapters and suction catheter systems, and methods of using the same, are described herein. An exemplary airway adapter assembly may comprise a connector body portion having a first end and a second end. The connector body portion may define an elongate cavity having an axial center between the first and the second end. The exemplary airway adapter assembly may also comprise a valve coupled to the second end of the connector body. The exemplary airway adapter assembly may also comprise a ventilation base member comprising a tubular portion coupled to the second end of the connector body portion and ventilator port. The ventilator port may comprises a conduit having a first conduit end and a second conduit end, and the first
(Continued)

conduit end may be coupled to the tubular portion through an articulable connection. An exemplary closed suction catheter system may comprise a suction control valve assembly and a closed suction catheter sheath.

14 Claims, 70 Drawing Sheets

Related U.S. Application Data on Aug. 8, 2014, provisional application No. 62/035,364, filed on Aug. 8, 2014, provisional application No. 62/035,380, filed on Aug. 8, 2014, provisional application No. 62/035,379, filed on Aug. 8, 2014.

(52) U.S. Cl.
CPC ..... *A61M 16/208* (2013.01); *A61M 2205/276* (2013.01); *A61M 2205/585* (2013.01)

(58) Field of Classification Search
CPC ............ A61M 16/0833; A61M 1/0035; A61M 1/0043; A61M 1/0045; A61M 16/0463; A61M 16/0486; A61M 16/08; A61M 16/0808; A61M 16/0841; A61M 16/085; A61M 16/0858; A61M 16/208; A61M 2016/0027; A61M 2039/0646; A61M 2039/0653; A61M 2039/0666; A61M 2039/242; A61M 2039/2426; A61M 2039/2433; A61M 2039/244; A61M 2205/276; A61M 2205/585; A61M 25/0097; A61M 25/0111; A61M 25/0606; A61M 25/0618; A61M 3/02; A61M 39/22; A61M 39/24; A61M 39/26; A61M 5/16881; A61B 5/087; A61B 46/10; F16K 15/147; Y10S 128/26; Y10S 128/912; Y10T 137/788

See application file for complete search history.

(56) References Cited

U.S. PATENT DOCUMENTS

| | | | |
|---|---|---|---|
| 4,696,296 A | 9/1987 | Palmer | |
| D300,361 S | 3/1989 | Tokarz | |
| 4,825,859 A | 5/1989 | Lambert | |
| 4,834,726 A | 5/1989 | Lambert | |
| 4,836,199 A | 6/1989 | Palmer | |
| 4,838,255 A | 6/1989 | Lambert | |
| 4,848,331 A | 7/1989 | Northway-Meyer | |
| 4,850,350 A | 7/1989 | Jackson | |
| 4,938,741 A | 7/1990 | Lambert | |
| 5,025,806 A | 6/1991 | Palmer et al. | |
| 5,029,580 A | 7/1991 | Radford et al. | |
| 5,031,613 A | 7/1991 | Smith et al. | |
| 5,060,646 A | 10/1991 | Page | |
| 5,083,561 A | 1/1992 | Russo | |
| 5,254,083 A | 10/1993 | Gentelia et al. | |
| 5,300,043 A | 4/1994 | Devlin et al. | |
| 5,775,325 A * | 7/1998 | Russo ............. | A61M 16/0463 128/202.27 |
| 6,070,582 A | 6/2000 | Kee | |
| D449,106 S | 10/2001 | Madsen et al. | |
| D449,107 S | 10/2001 | Madsen et al. | |
| 6,530,504 B2 * | 3/2003 | Socier ............. | B65D 47/2031 222/212 |
| 6,543,451 B1 * | 4/2003 | Crump ............. | A61M 16/0463 128/207.14 |
| 6,609,520 B1 | 8/2003 | Carlsen et al. | |
| 6,612,304 B1 | 9/2003 | Cise et al. | |
| D492,030 S | 6/2004 | Rani | |
| D519,632 S | 4/2006 | Bayron et al. | |
| D650,478 S | 12/2011 | Lewis | |
| D653,329 S | 1/2012 | Lee-Sepsick | |
| D654,583 S | 2/2012 | Lee-Sepsick | |
| D655,412 S | 3/2012 | Luk et al. | |
| D660,957 S | 5/2012 | Lee-Sepsick | |
| 8,187,234 B2 * | 5/2012 | Weaver ............. | A61M 39/24 604/247 |
| 8,490,622 B2 | 7/2013 | Stenzler et al. | |
| D691,717 S | 10/2013 | McLean et al. | |
| D712,027 S | 8/2014 | Zerwic et al. | |
| 8,814,838 B2 * | 8/2014 | Landis ............. | A61M 16/0463 604/317 |
| D713,958 S | 9/2014 | Srinivasan et al. | |
| D714,436 S | 9/2014 | Lee-Sepsick | |
| D727,492 S | 4/2015 | Scampoli | |
| D730,518 S | 5/2015 | Lombardi, III et al. | |
| 9,022,036 B2 * | 5/2015 | Graham ............. | A61M 16/0463 128/207.14 |
| 9,114,231 B2 * | 8/2015 | Woehr ............. | A61M 25/0075 |
| D747,473 S | 1/2016 | Martin et al. | |
| D749,721 S | 2/2016 | Dziak et al. | |
| D764,660 S | 8/2016 | Babbs et al. | |
| 9,427,541 B2 | 8/2016 | Chiu | |
| D771,806 S | 11/2016 | Steele | |
| 2003/0047704 A1 | 3/2003 | Svendsen | |
| 2004/0144435 A1 * | 7/2004 | Dark ............. | F16K 15/147 137/844 |
| 2006/0005841 A1 | 1/2006 | Anderson et al. | |
| 2007/0282250 A1 | 12/2007 | Anderson et al. | |
| 2011/0067699 A1 * | 3/2011 | Caruso ............. | A61M 16/0463 128/205.29 |
| 2013/0144268 A1 | 6/2013 | Chung | |
| 2013/0296653 A1 | 11/2013 | Brown et al. | |
| 2013/0312755 A1 | 11/2013 | Ho | |
| 2013/0312756 A1 | 11/2013 | Ho | |
| 2013/0312759 A1 | 11/2013 | Ho | |
| 2015/0306349 A1 * | 10/2015 | Bonnal ............. | A61M 25/0097 604/272 |
| 2016/0022942 A1 * | 1/2016 | Millar ............. | A61M 16/0463 128/202.13 |
| 2016/0038700 A1 | 2/2016 | White et al. | |
| 2016/0038701 A1 | 2/2016 | White et al. | |
| 2017/0143921 A1 | 5/2017 | White et al. | |

FOREIGN PATENT DOCUMENTS

| | | |
|---|---|---|
| JP | 2007111558 A | 5/2007 |
| JP | 2011529740 A | 12/2011 |
| WO | WO-0015276 A1 | 3/2000 |
| WO | WO-0024439 A1 | 5/2000 |
| WO | WO-0176673 A1 | 10/2001 |
| WO | WO-2005094925 A1 | 10/2005 |
| WO | WO-2007146613 A2 | 12/2007 |
| WO | WO-2010014735 A1 | 2/2010 |
| WO | WO-2010052241 A1 | 5/2010 |

OTHER PUBLICATIONS

International Search Report and Written Opinion for Application No. PCT/US2015/044244, dated Feb. 4, 2016, 21 pages.
Chinese Office Action for Application No. 201510484397.0, dated Sep. 4, 2018, 6 pages.
Extended European Search Report for Application No. 18168278.2, dated Jul. 23, 2018, 10 pages.
Japanese Office Action for Application No. 2017-527539, dated May 7, 2019, 6 pages.

* cited by examiner

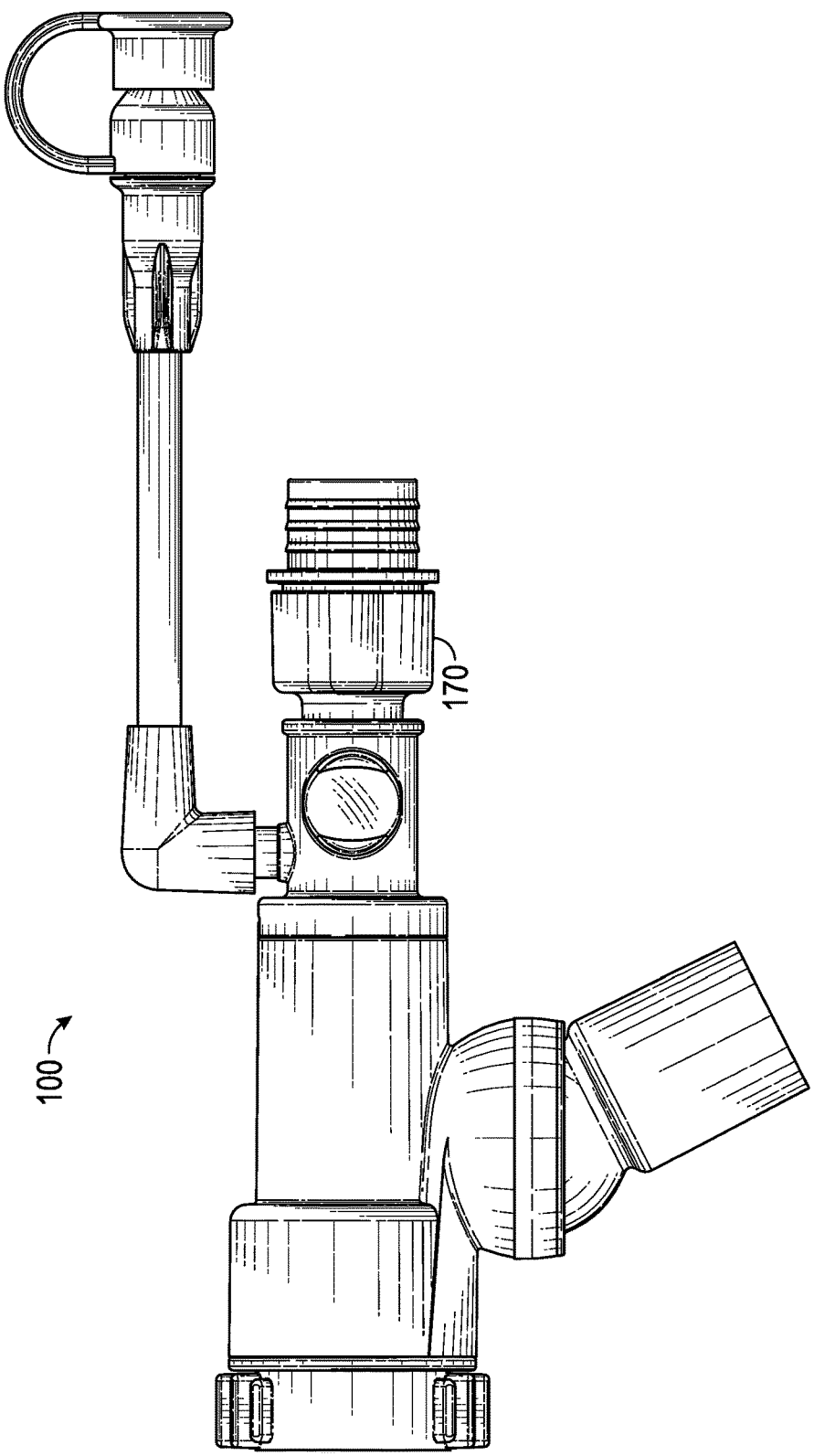

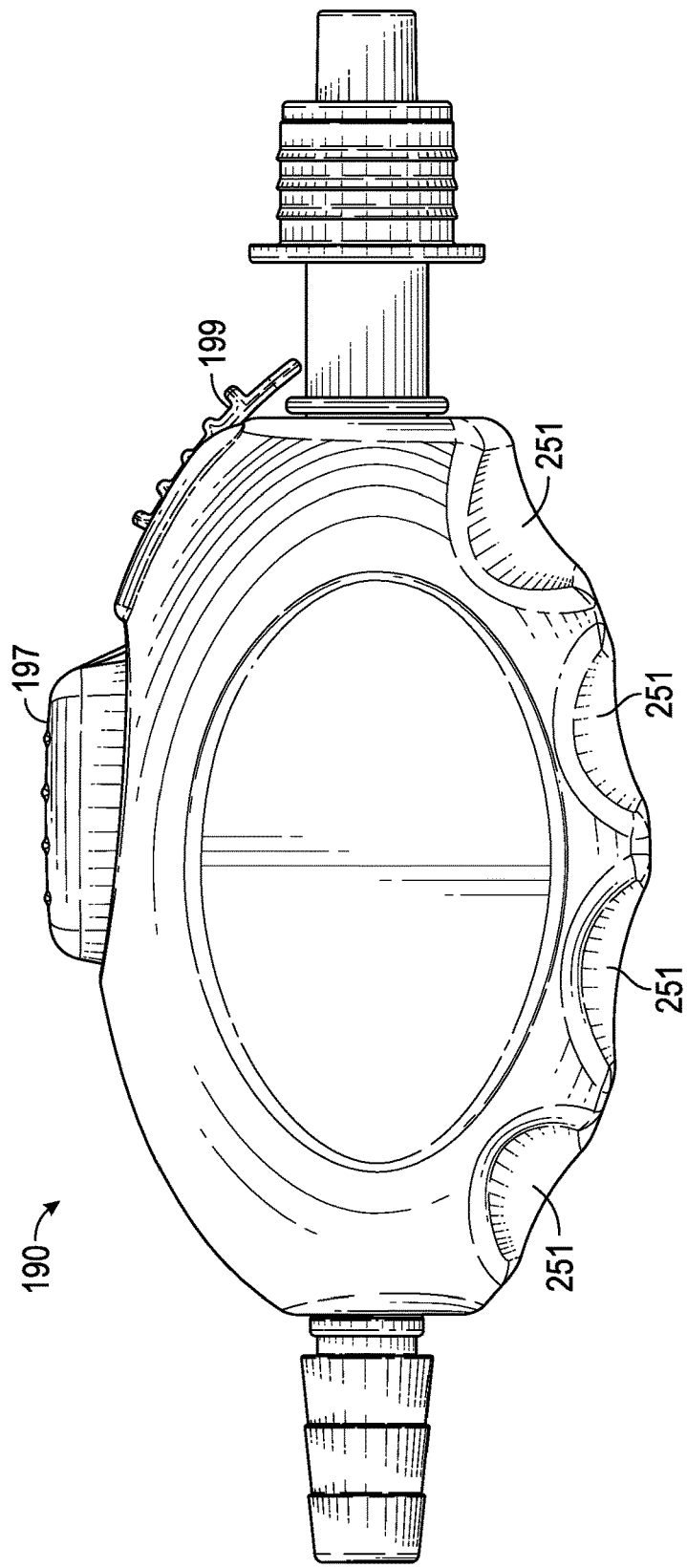

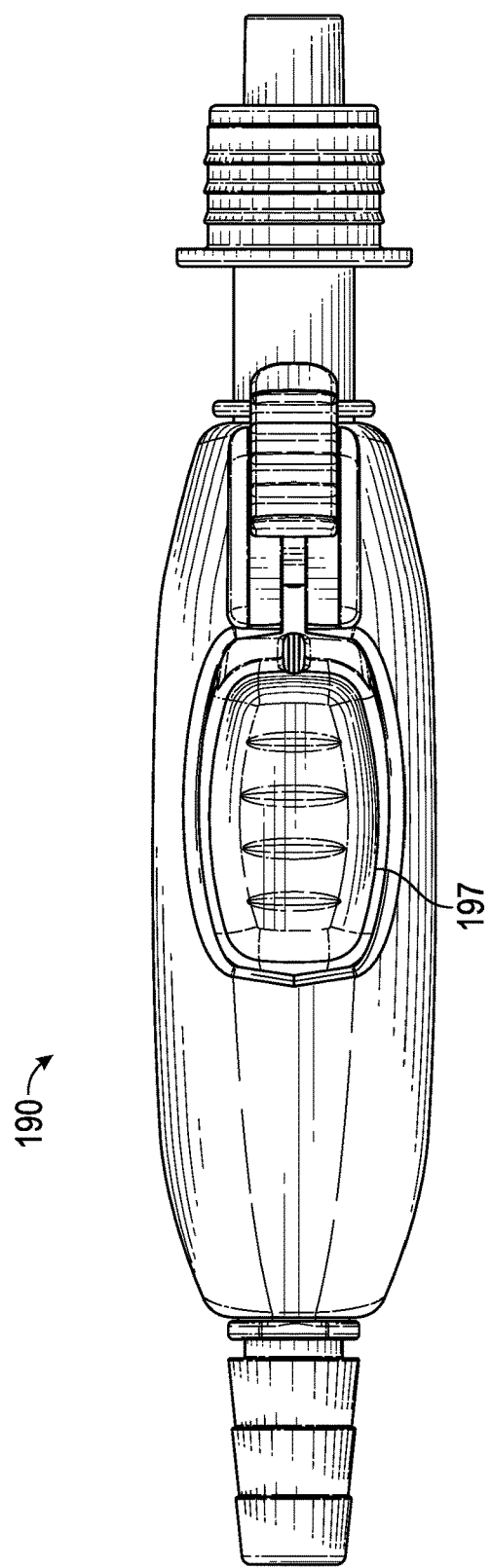

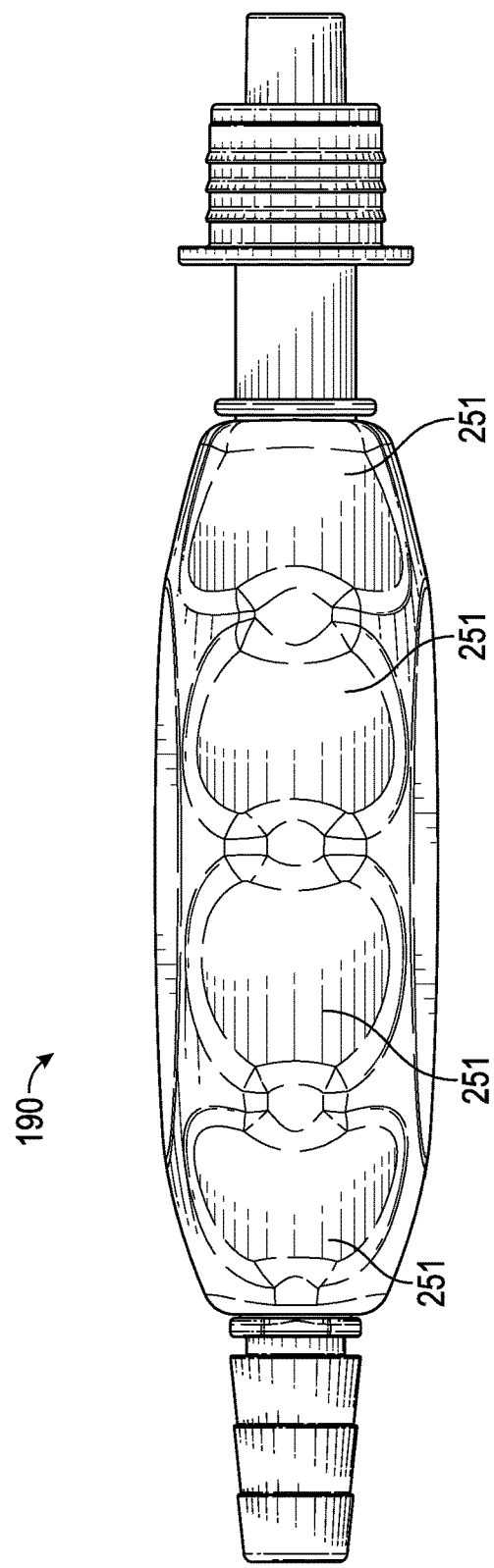

AIRWAY ADAPTERS AND SUCTION CATHETER SYSTEMS

CROSS-REFERENCE TO RELATED APPLICATIONS

The present application claims priority to U.S. Provisional Patent Application No. 62/035,366, filed on Aug. 8, 2014, entitled, "ELONGATION LIMITING SUCTION CATHETER SHEATH," U.S. Provisional Patent Application No. 62/035,367, filed on Aug. 8, 2014, entitled, "MULTIPLE ACCESS PORT AIRWAY ADAPTOR," U.S. Provisional Patent Application No. 62/035,379, entitled, "AIRWAY ADAPTER VALVES AND METHODS OF USE," U.S. Provisional Patent Application No. 62/035,380, filed Aug. 8, 2014, entitled, "SUCTION CONTROL VALVES AND METHODS OF USE," and U.S. Provisional Patent Application No. 62/035,364, entitled, "AIRWAY ADAPTERS AND SUCTION CATHETER SYSTEMS." The entirety of these priority applications are incorporated by reference herein.

TECHNICAL FIELD

The present disclosure generally relates to airway adapters, suction catheter systems, and more particularly to airway adapter assemblies, suction catheters, closed suction catheter sheaths, suction control valves, and methods of using the same.

BACKGROUND

Ventilators and related breathing circuits may be used to assist in patient breathing. For example, during surgery and other medical procedures, a patient may be connected to a ventilator to provide respiratory gases to the patient. The ventilation source may be connected into the patient's respiratory tract via an artificial airway, such as a tracheostomy tube, endotracheal tube, etc. While some breathing circuit can establish a single, direct fluid connection between the ventilator and the artificial airway, in many instances, caregivers desire the ability to introduce instruments and/or materials into the breathing circuit, for example, to insert instruments for visualization or related procedures, or to aspirate fluid or secretions from the patient's airway. Accordingly, suction catheters and suction valves may be used by caregivers in closed and open suction catheter systems to aspirate fluid or secretions (e.g., mucus, secretions, blood, foreign particles, etc.) from the patient's airway.

SUMMARY

Aspects of the subject technology relate to airway adapters and suction catheter systems, and methods of using the same. In accordance with certain aspects, an airway adapter assembly may comprise a connector body portion having a first end and a second end, the connector body portion defining an elongate cavity having an axial center between the first and the second end; a valve coupled to the second end of the connector body, the valve comprising an outer rim section configured to engage with a valve retention structure and an inner resiliently flexible diaphragm section integrally connected to the outer rim section, the inner resiliently flexible diaphragm section comprising a plurality of valve segments defined by one or more slits, wherein one or more of the valve segments include one or more first regions and one or more second regions, wherein a primary seal is formed by the plurality of valve segments, and a secondary seal is formed by an arrangement of the one or more first regions of the plurality of the valve segments, and wherein the secondary seal has a first cracking pressure, and the primary seal has a second cracking pressure different from the first cracking pressure; and a ventilation base member comprising a tubular portion coupled to the second end of the connector body portion and ventilator port, wherein the ventilator port comprises a conduit having a first conduit end and a second conduit end, wherein the first conduit end is coupled to the tubular portion through an articulable connection such that the ventilator port is articulable about the tubular portion in at least two axes.

In accordance with certain aspects, a closed suction catheter system may comprise a suction control valve assembly comprising a housing having an interior cavity of the housing, a rigid tubular section coupled to the housing and having at least a portion of the rigid tubular section disposed within the interior cavity of the housing, the rigid tubular section having a first end, a second end, a pathway extending between the first end and the second end, and a pathway access opening arranged between the first end and the second end, an elastomeric valve member being coupled to and enclosing the pathway access opening of the rigid tubular section, and a pivotable actuator structure having a lever portion coupled to the elastomeric valve member; and a closed suction catheter sheath comprising a catheter and a flexible sleeve for enveloping the catheter, wherein the catheter is fixedly attached to the suction control valve assembly.

In accordance with certain aspects, a method of using a closed suction catheter system may comprise securing an airway adapter; advancing a suction catheter into an artificial airway of a patient through the airway adapter; and providing a depth indicator of the suction catheter via a lens disposed on the airway adapter.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIG. 2B is a front view of the example of the multiple-port airway adapter depicted in FIG. 2A.

FIG. 2M is a front view of the example of the suction control valve depicted in FIG. 2L.

FIG. 2R is a top view of the example of the suction control valve depicted in FIG. 2L.

FIG. 2S is a bottom view of the example of the suction control valve depicted in FIG. 2L.

FIG. 3J' illustrates a cross-sectional plan view of an example of a multiple-port airway adapter, in accordance with aspects of the present disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Figure 1A:
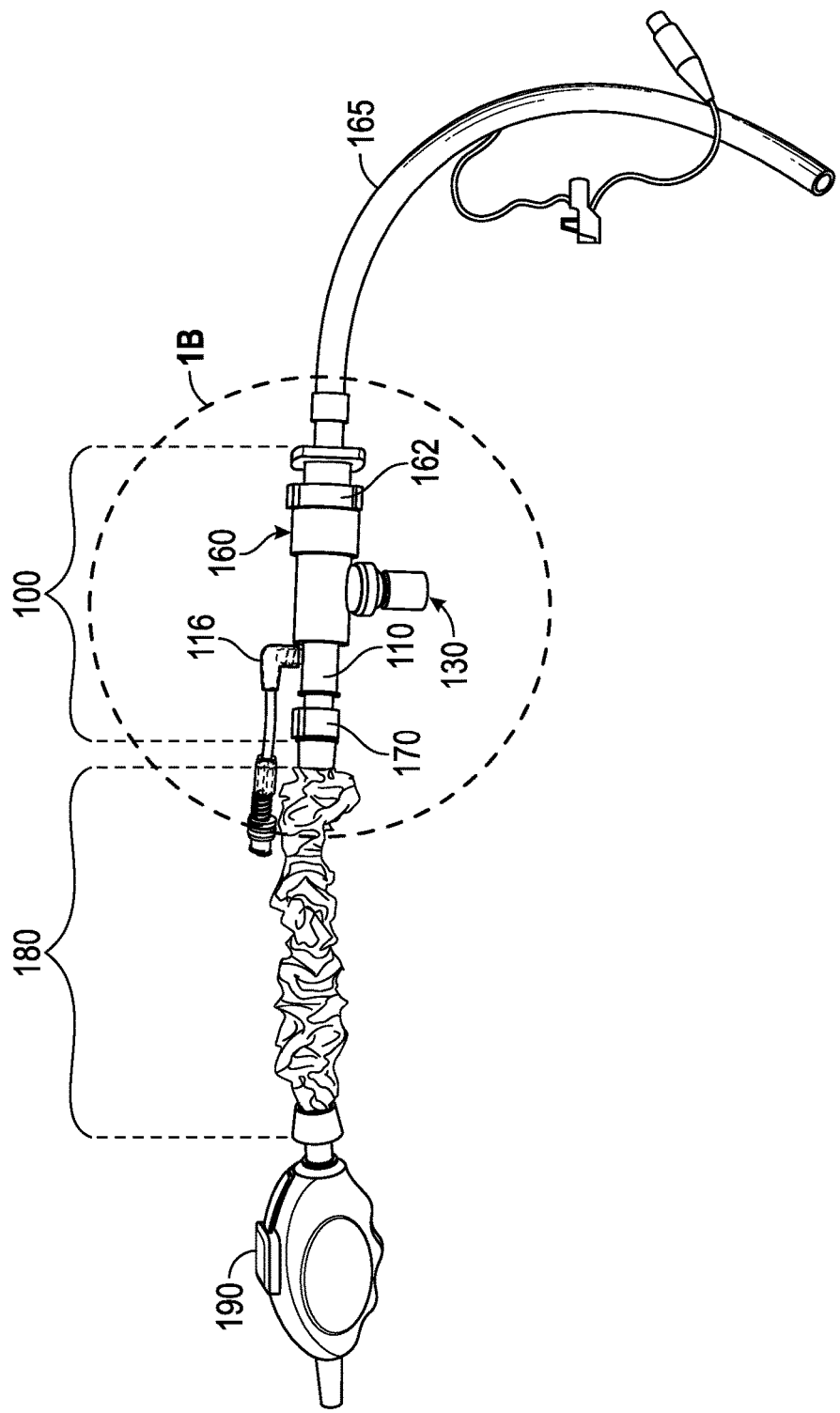
FIG. 1A illustrates an example of a closed suction catheter system, in accordance with aspects of the present disclosure.
Figure 1B:
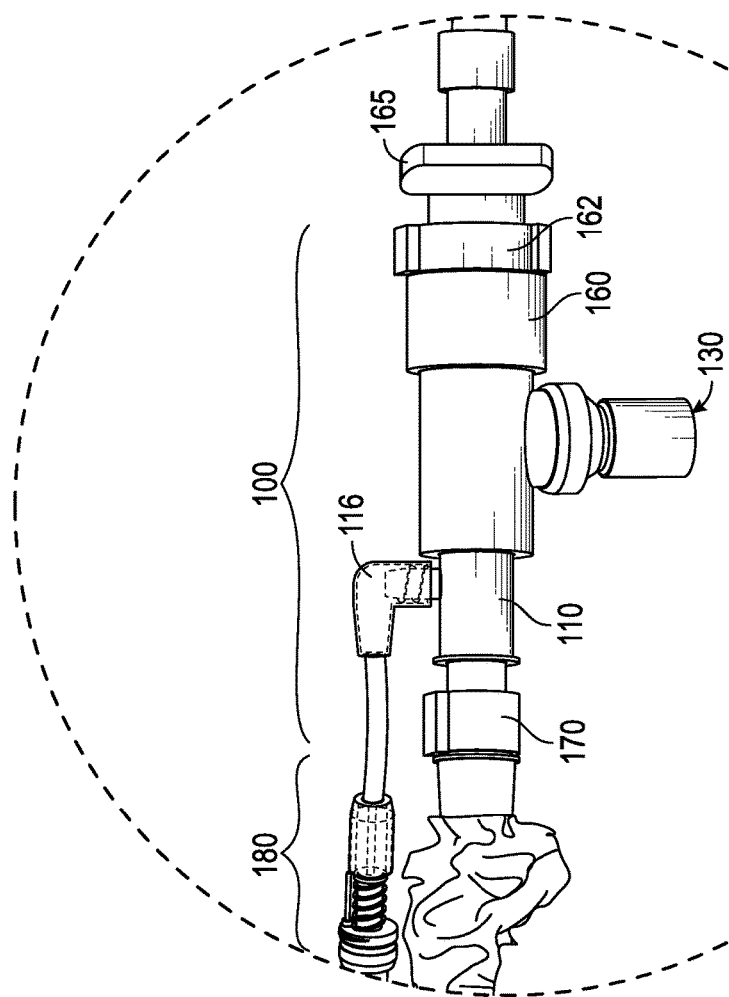
FIG. 1B illustrates a detail view of an example of a closed suction catheter system, in accordance with aspects of the present disclosure.
Figure 1C:
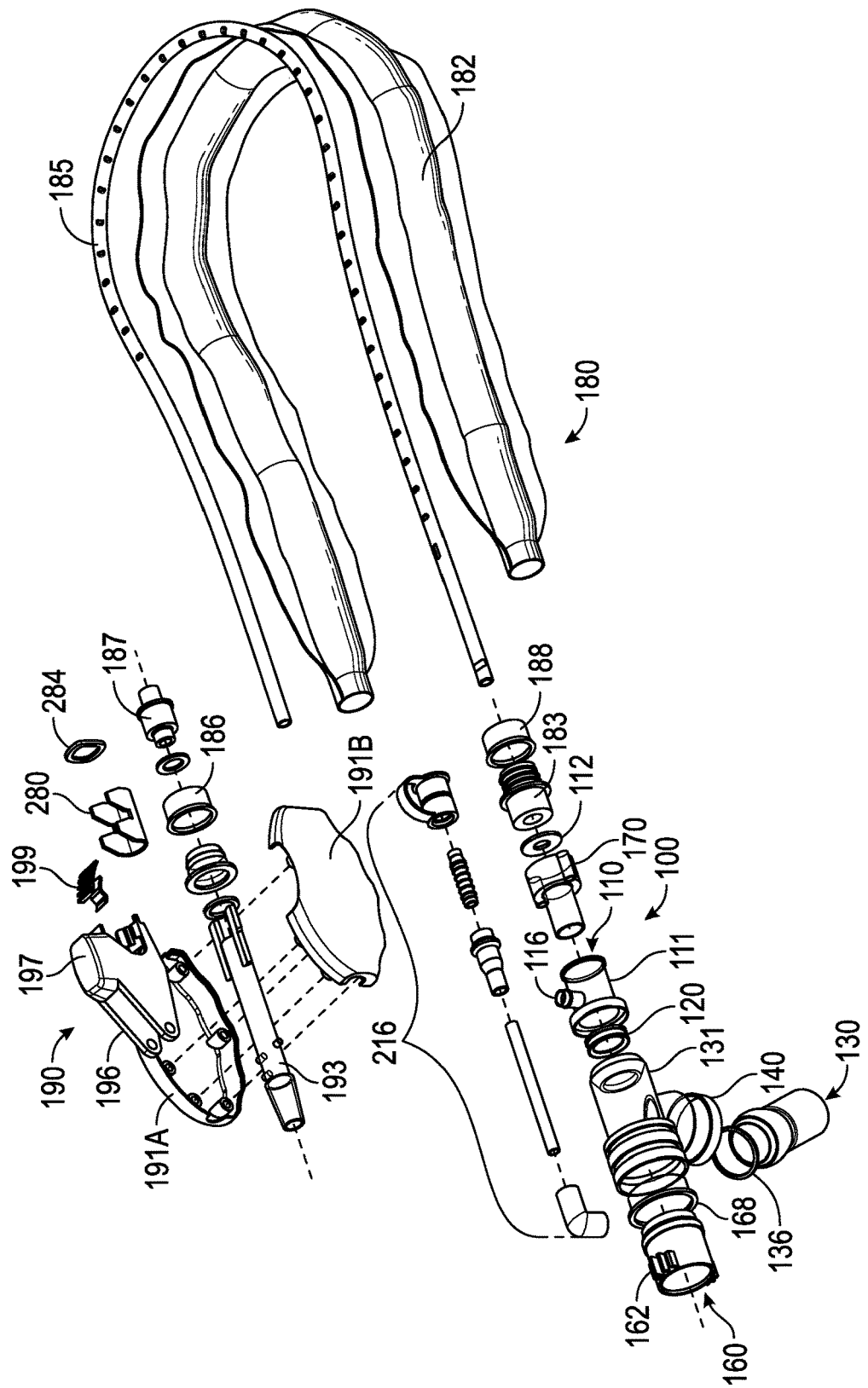
FIG. 1C illustrates an exploded view of an example of a closed suction catheter system, in accordance with aspects of the present disclosure.

FIGS. 1A-1C illustrate examples of a closed suction catheter system. In certain embodiments, closed catheter suction system 10 may comprise an airway adapter 100 having a multi-purpose valve (e.g., a peak inspiratory pressure valve having multiple seals and associated cracking pressures). For example, airway adapter 100 may have a manifold-type body providing three or more fluidly connectable ports including, but not limited to, a ventilator port, a respiratory port, and an access port. However, it is understood that airway adapters and like adapters in accordance with the present disclosure are not limited to manifold-type bodies. Airway adapter 100 may be coupled to artificial airway 165, for example, at a respiratory port 160 of the airway adapter 100. The respiratory port 160 may include an annular swivel connector 162, allowing the multiple-port airway adapter 100 to rotate, with respect to the swivel connector 162, about a fluid pathway axis.

Airway adapter 100 may be further coupled to airway adapter coupler 170, for example, at an access port of the airway adapter 100. A suction catheter, tubing, or other medical implement may be inserted through airway adapter coupler 170 and into the access port 110 of the airway adapter 100. In this regard, airway adapter coupler 170 can be configured to receiver various medical implements, such as but not limited to, a suction catheter included in closed suction catheter sheath 180. For example, closed suction catheter sheath 180 may be coupled to airway adapter coupler 170 via capture ring 188 using, for example, an interference fitting, threaded surfaces, and/or a compression coupling. Closed suction catheter sheath 180 may be further coupled to suction control valve 190 via capture ring 186, for example. In operation, suction control valve 190 may be coupled to a suction source 195.

Various components of an example of a closed suction catheter system are illustrated in the exploded view of FIG. 1C. These components will be discussed in further detail herein, however, are illustrated in FIG. 1C to provide an example assembly of a closed suction catheter system. For example, closed suction catheter system may include suction control valve 190, suction catheter sheath 180, airway adapter coupler 170, and airway adapter 100. It is to be understood that the certain components may be omitted, included and/or combined with other components in various embodiments and implementations.

For example, in some embodiments, airway adapter coupler 170 may be integrated with suction catheter sheath 180, and in some embodiments, adapter coupler 170 may be integrated with connector body 111 of airway adapter 100. Additionally, flush port 116 (or wash port) may be disposed on adapter coupler 170 instead of airway adapter 100, in accordance with some embodiments. In certain embodiments, wash port coupling assembly 216 may be configured to be removably coupled to flush port 116. In some embodiments, suction catheter sheath 180 may be fixably coupled to suction control valve 190. In some embodiments, suction catheter 185 may be configured without sleeve 182 for use with airway adapter 100 and/or suction control valve 190 (e.g., an open suction catheter system).

Figure 1D:
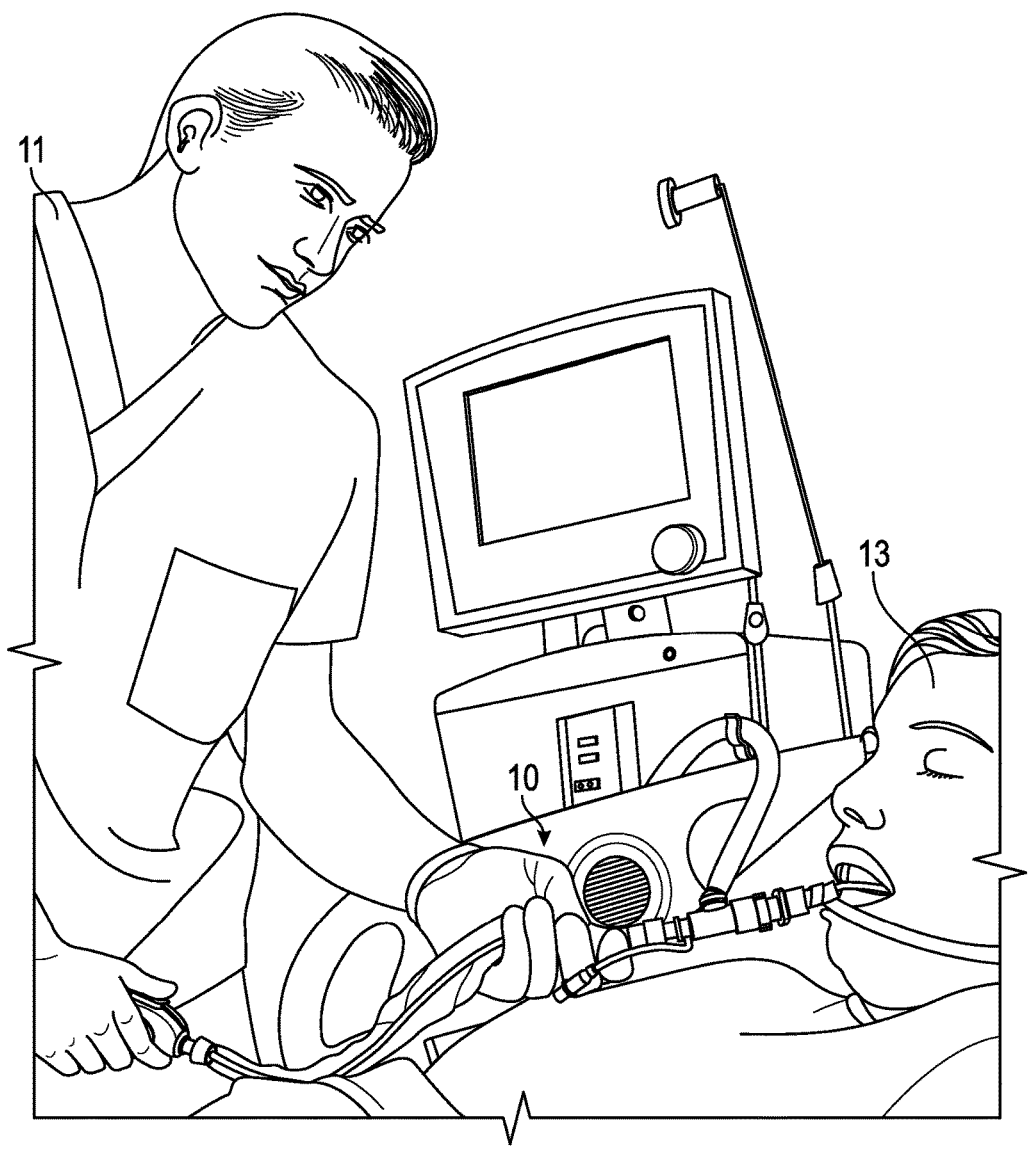
FIG. 1D illustrates an example of a closed suction catheter system connected to a patient, in accordance with aspects of the present disclosure.
Figure 2A:
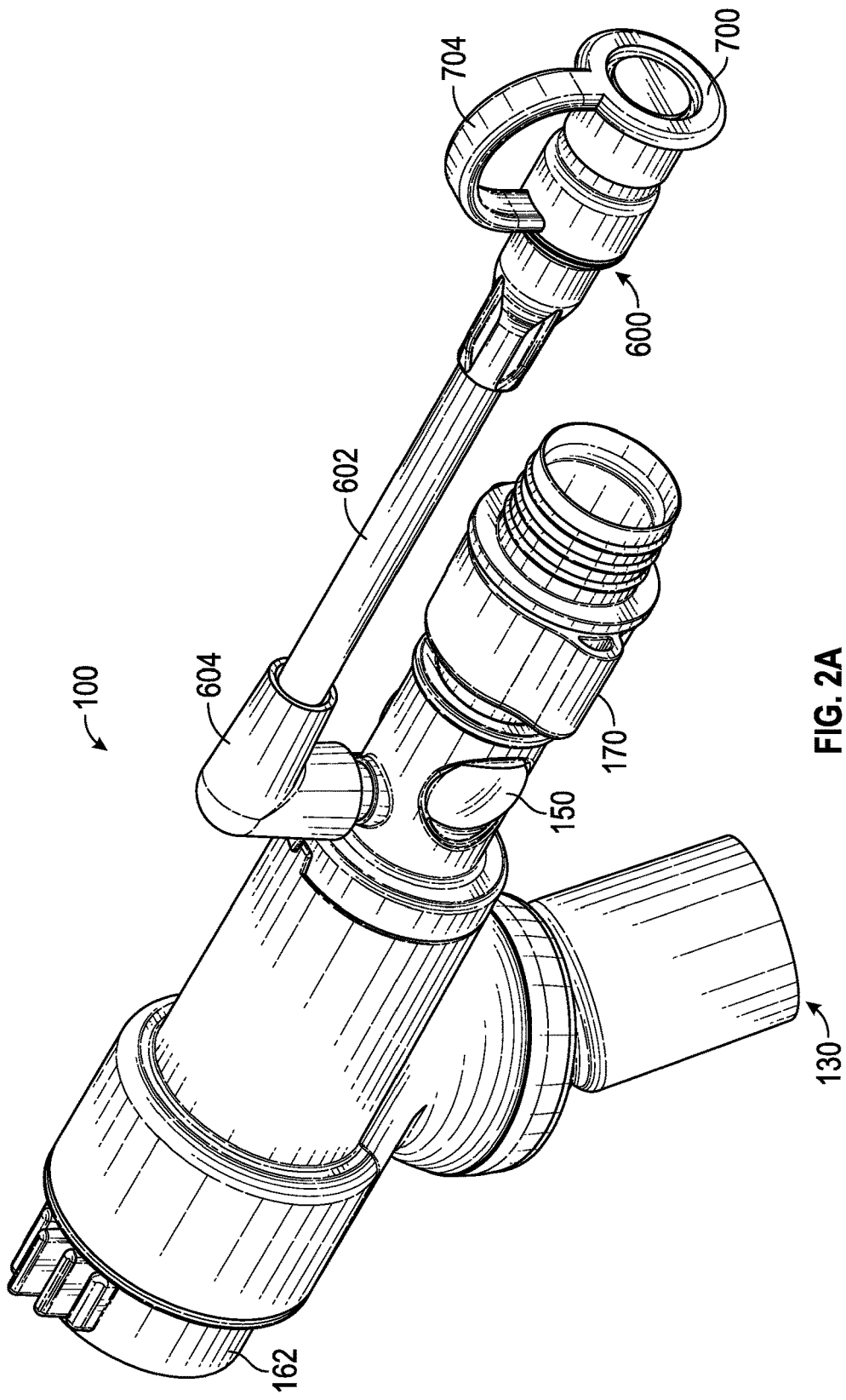
FIG. 2A is a perspective view of an example of a multiple-port airway adapter, in accordance with aspects of the present disclosure.
Figure 2C:
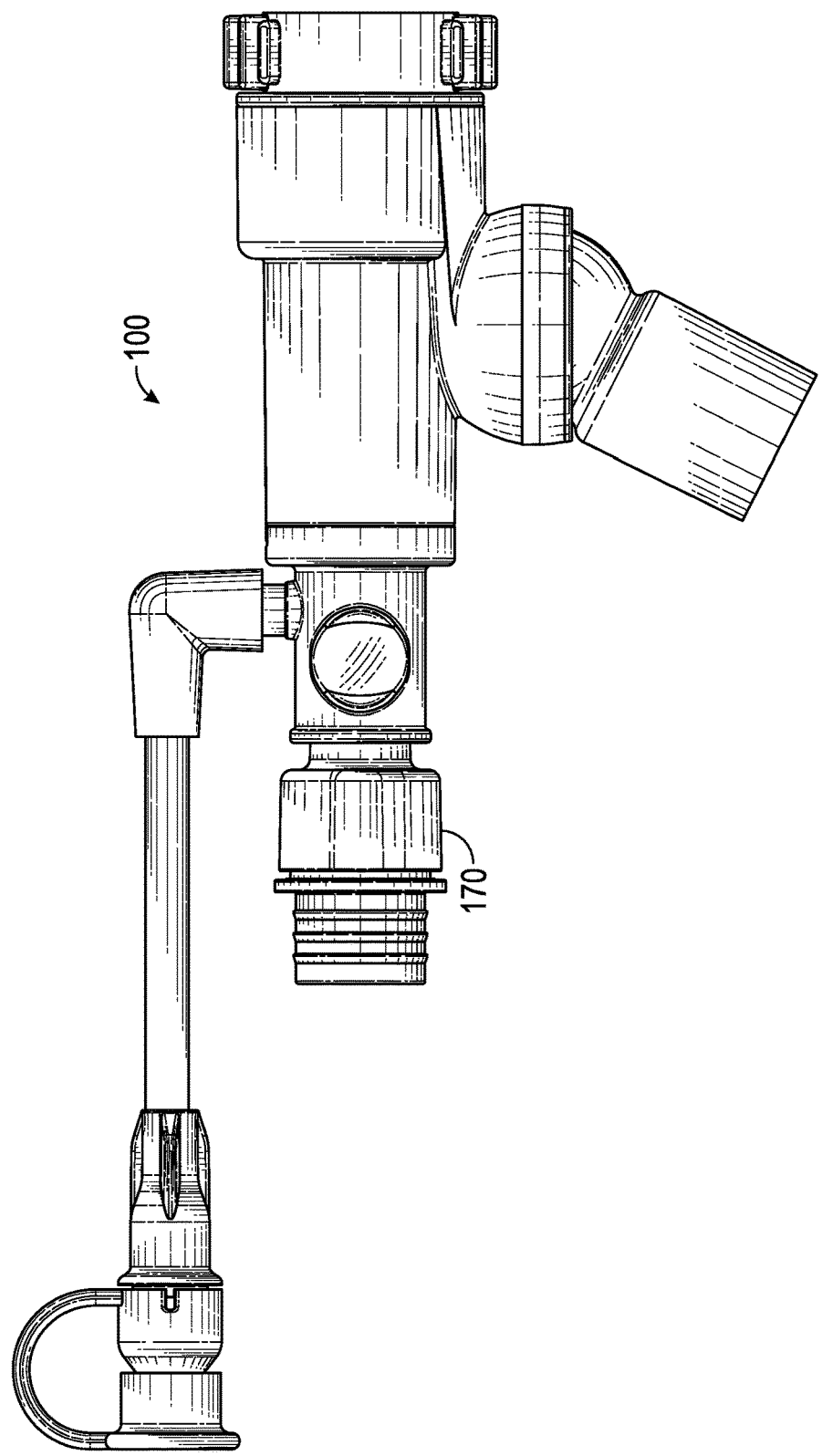
FIG. 2C is a rear view of the example of the multiple-port airway adapter depicted in FIG. 2A.
Figure 2D:
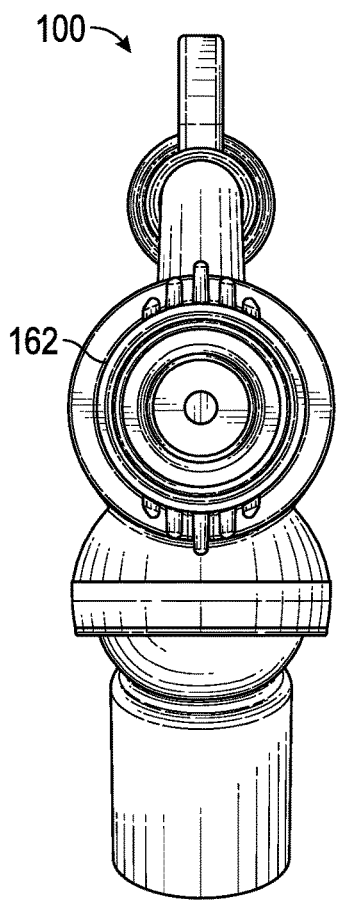
FIG. 2D is a left side view of the example of the multiple-port airway adapter depicted in FIG. 2A.
Figure 2E:
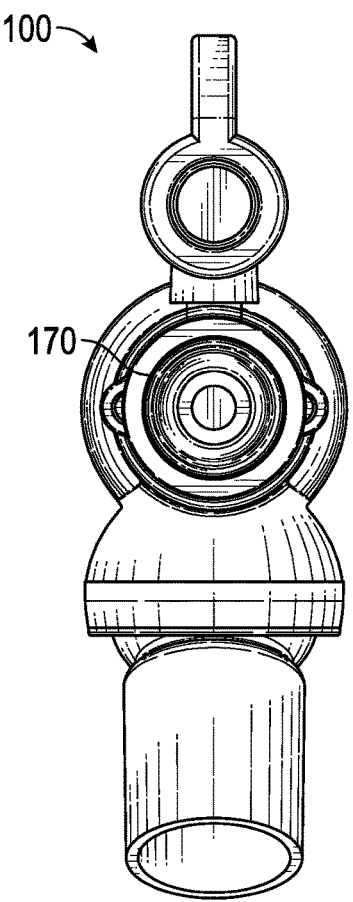
FIG. 2E is a right side view of the example of the multiple-port airway adapter depicted in FIG. 2A.
Figure 2F:
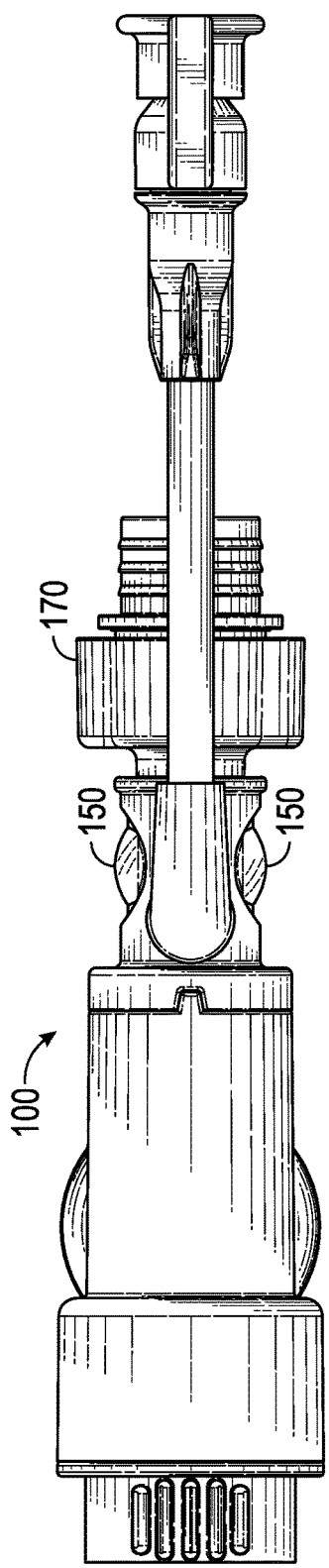
FIG. 2F is a top view of the example of the multiple-port airway adapter depicted in FIG. 2A.
Figure 2G:
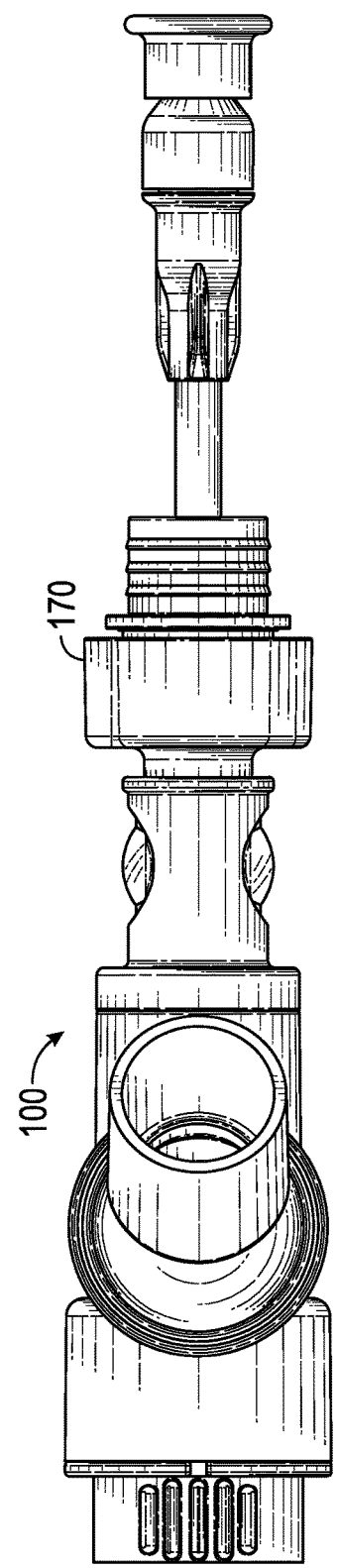
FIG. 2G is a bottom view of the example of the multiple-port airway adapter depicted in FIG. 2A.
Figure 2H:
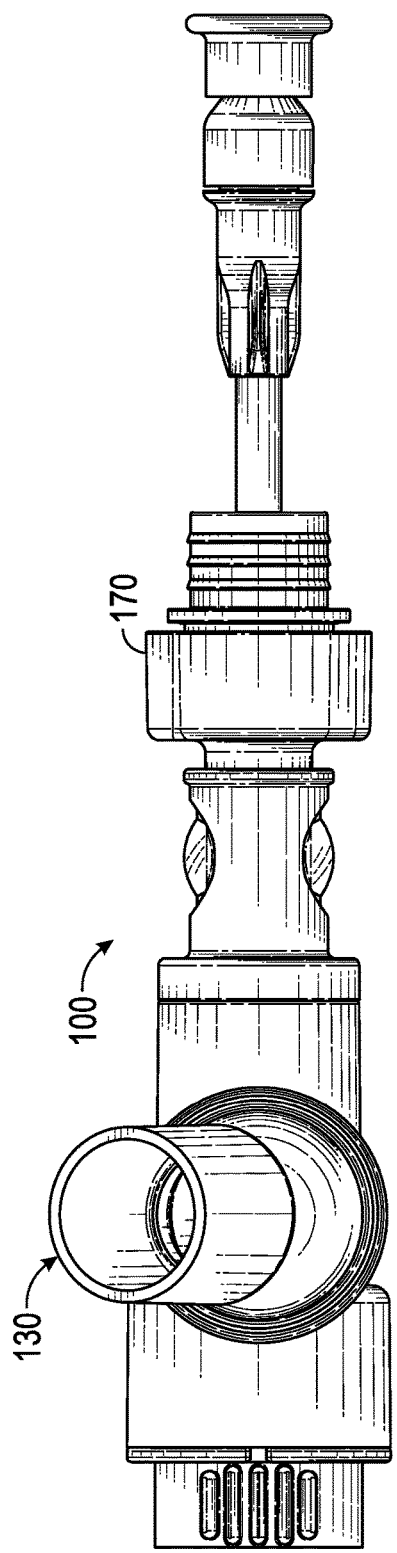
FIG. 2H is an additional bottom view of the example of the multiple-port airway adapter depicted in FIG. 2A.
Figure 2J:
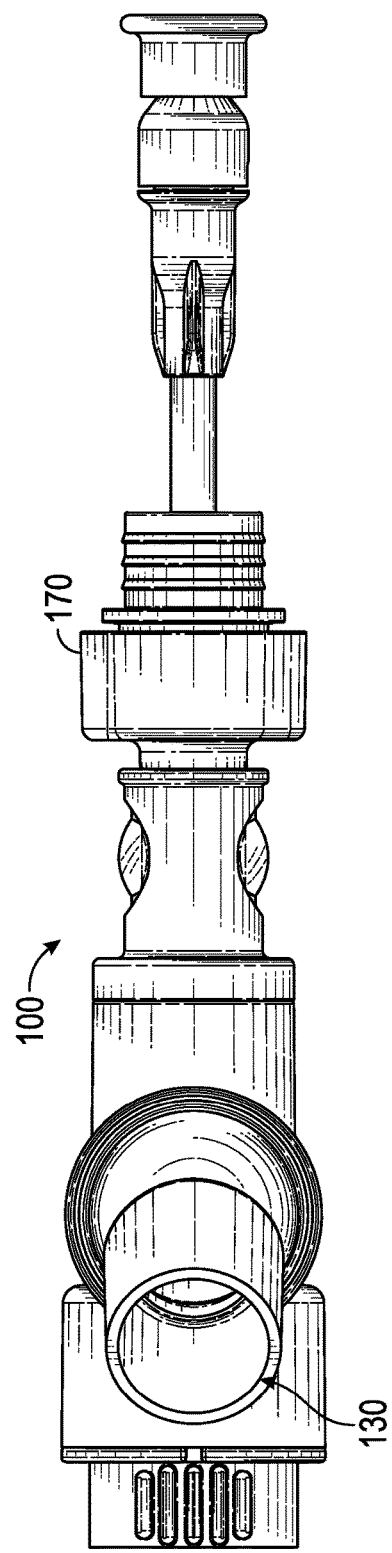
FIG. 2J is an additional bottom view of the example of the multiple-port airway adapter depicted in FIG. 2A.
Figure 2K:
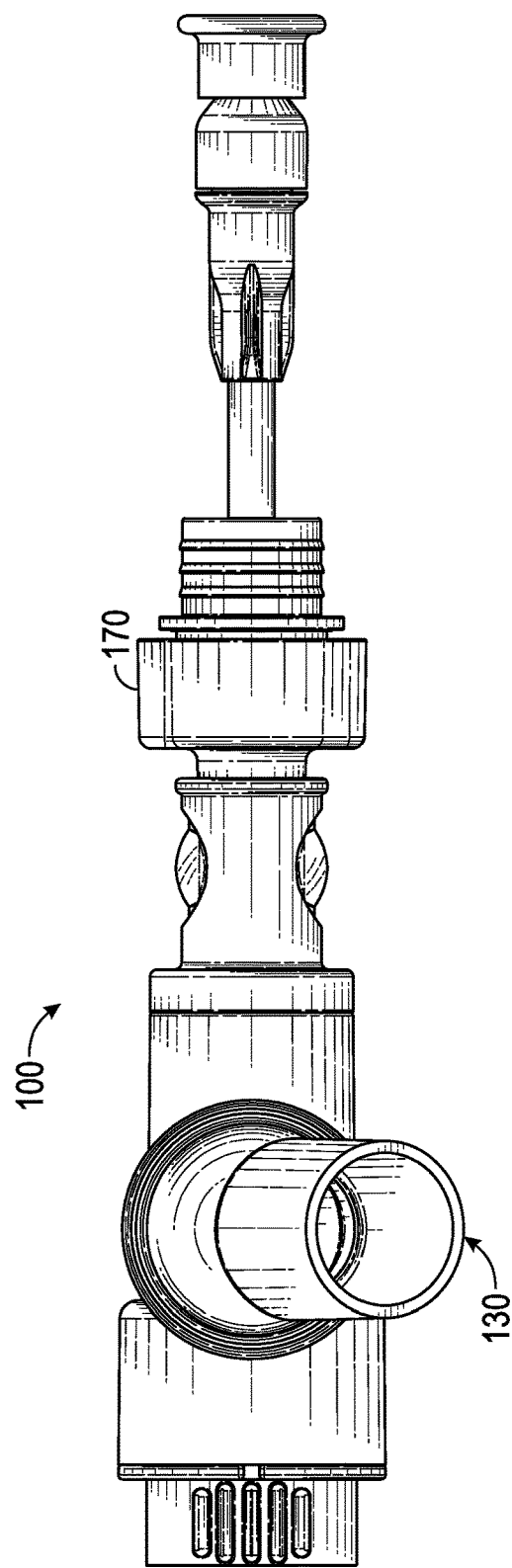
FIG. 2K is an additional bottom view of the example of the multiple-port airway adapter depicted in FIG. 2A
Figure 2L:
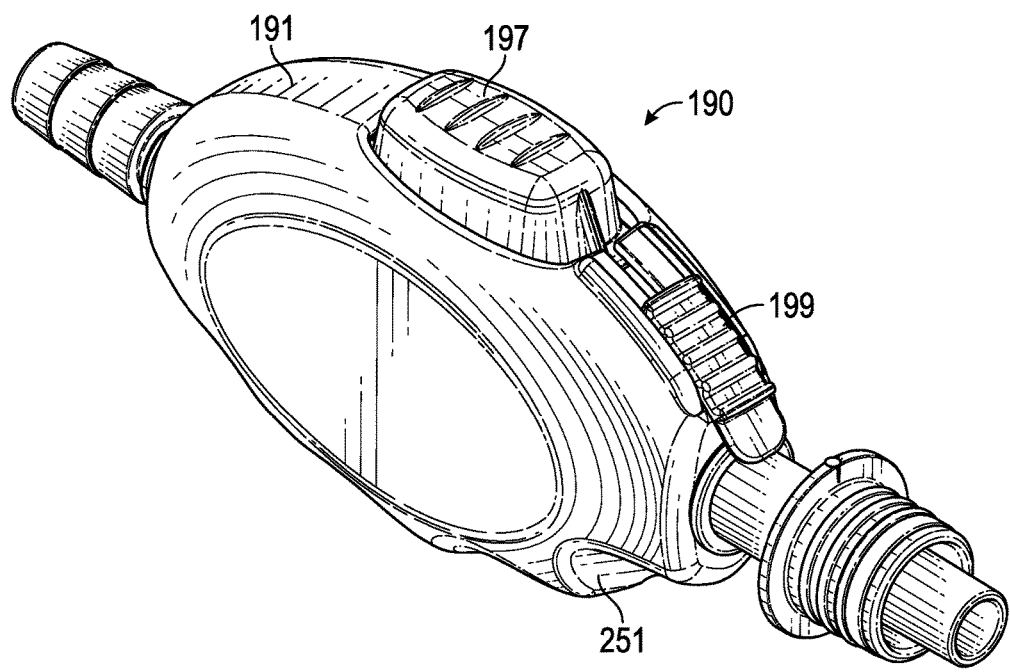
FIG. 2L is a perspective view of an example of a suction control valve, in accordance with aspects of the present disclosure.
Figure 2N:
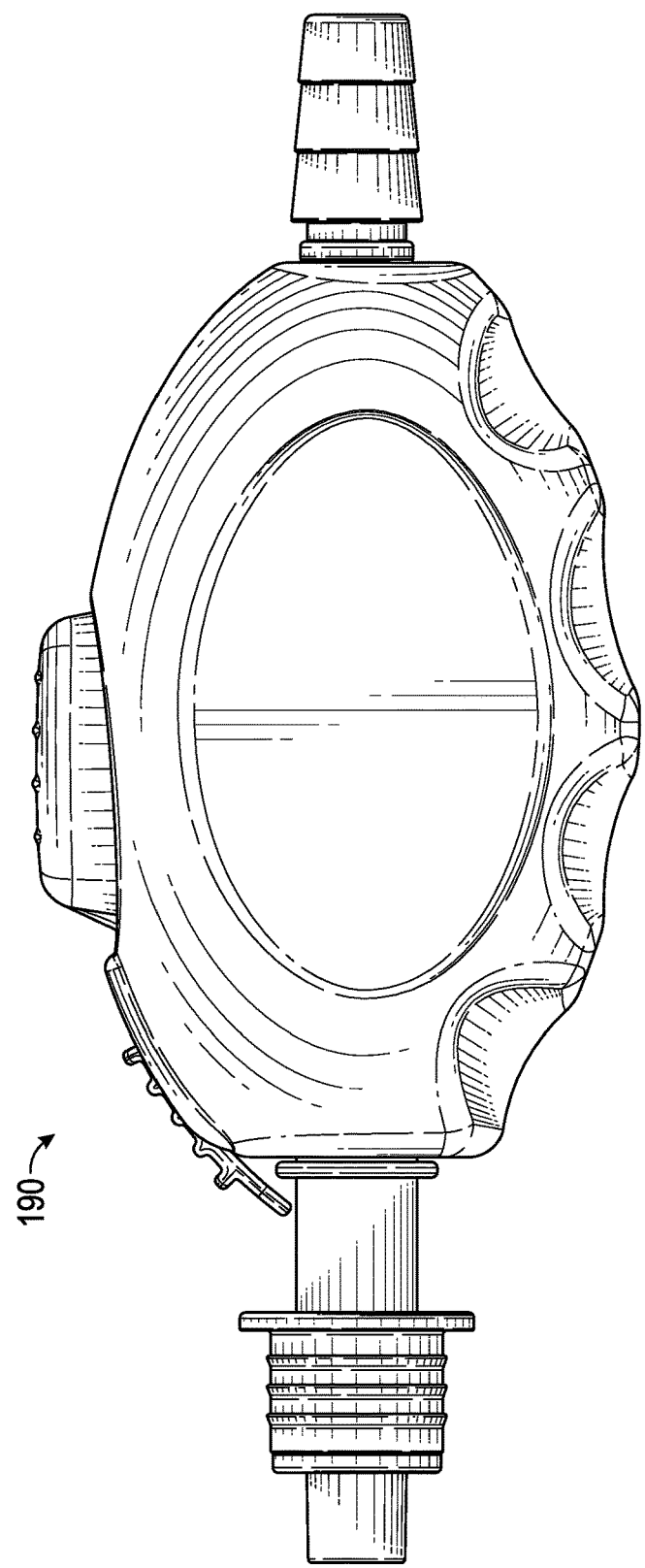
FIG. 2N is a rear view of the example of the suction control valve depicted in FIG. 2L.
Figure 2P:
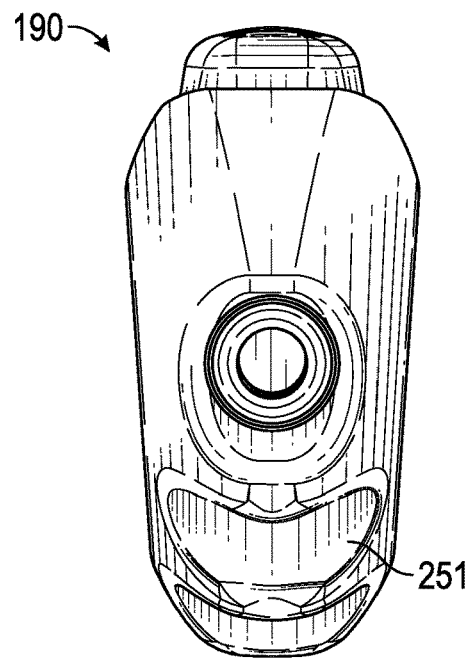
FIG. 2P is a left side view of the example of the suction control valve depicted in FIG. 2L.
Figure 2Q:
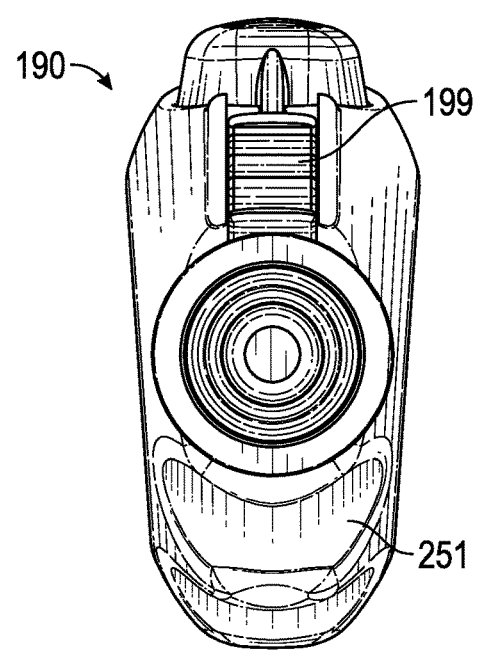
FIG. 2Q is a right side view of the example of the suction control valve depicted in FIG. 2L.

FIG. 1D illustrates an example of a closed suction catheter system in use. Reference to the example closed catheter system described and illustrated in FIGS. 1A-1C is made to provide context for FIGS. 1A-1C as well as the other figures and the various aspects of the present disclosure. Closed suction catheter system 10 enables caregiver 11 to perform respiratory-related procedure on a patient 13. For example, caregiver 11 may insert instruments for visualization or related procedures, or to aspirate fluid or secretions from the patient's airway. In this regard, airway adapter 100 can be assembled to a breathing circuit with a ventilator fluidly connected to the ventilator port and the artificial airway 165 fluidly connected to the respiratory port of the airway adapter 100 and inserted into the airway of the patient 13. With use of airway adapter 100, the patient 13 may be protected from loss of airway pressure during various procedures performed by the caregiver 11, such as changing-out of a contaminated or malfunctioning suction catheter sheath or to insert another airway instrument or medical implement into the artificial airway 165.

Accordingly, airway adapter 100 provides a breachable seal between the access port of the airway adapter 100 and the ventilation and respiratory ports so that fluid pressures required to maintain ventilation of the patient 13 are not lost via the access port during normal operation. It is to be appreciated that airway adapter 100 can be beneficial with patients requiring long-term mechanical ventilation and multiple respiratory-related procedures, for example, by enabling repeated connections of the suction catheter simultaneously with the breathing circuit.

FIGS. 2A-2K provide perspective and plan views of an example of a multiple-port airway adapter. In this regard, various aspects of airway adapter 100 are illustrated herein. For example, aspects of airway adapter 100 including, but not limited to, an airway adapter coupler 170, lens 150, ventilator port 130, and swivel connector 162 are illustrated in FIGS. 2A-2K.

For example, airway adapter 100 may include a wash port coupling assembly (e.g., wash port coupling assembly 216 in the example of FIG. 1C) comprising a wash port valve assembly 600, tubular connector, and elbow connector. In certain embodiments, wash port valve assembly may comprise a multi-part valve housing and an elastomeric valve disposed within the multi-part valve housing. Multi-part valve housing may be formed from a valve body cap portion and a valve body base portion. In accordance with certain embodiments of the wash port valve assembly, each of the valve body cap portion, valve body base portion, and elastomeric valve may be formed from different material and/or similar materials having different characteristics and properties. In some embodiments, one or both of the valve body cap portion and valve body base portion may be substantially rigid and generally cylindrically shaped.

Additionally, articulation of ventilator port 130 can be seen in the illustrations of FIGS. 2G-2K, for example.

FIGS. 2L-2S provide perspective and plan views of an example of a suction control valve. In this regard, various aspects of suction control valve 190 are illustrated herein. For example, aspects of suction control valve 190 including, but not limited to, housing 191, button 197, lock 199, and arcuate detents 251 are illustrated in FIGS. 2L-2S.

Figure 3A:
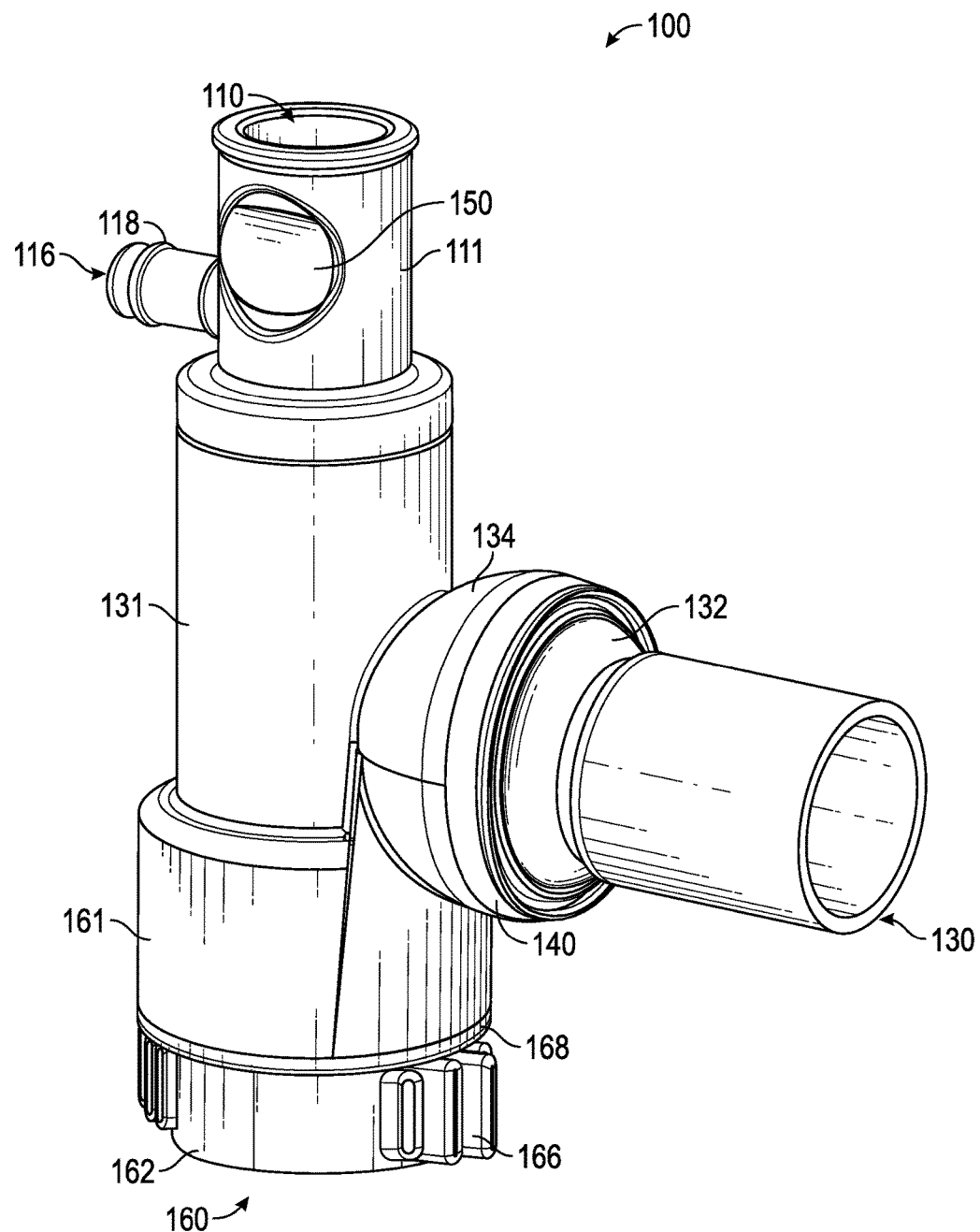
FIG. 3A illustrates a perspective view of an example of a multiple-port airway adapter, in accordance with aspects of the present disclosure.
Figure 3B:
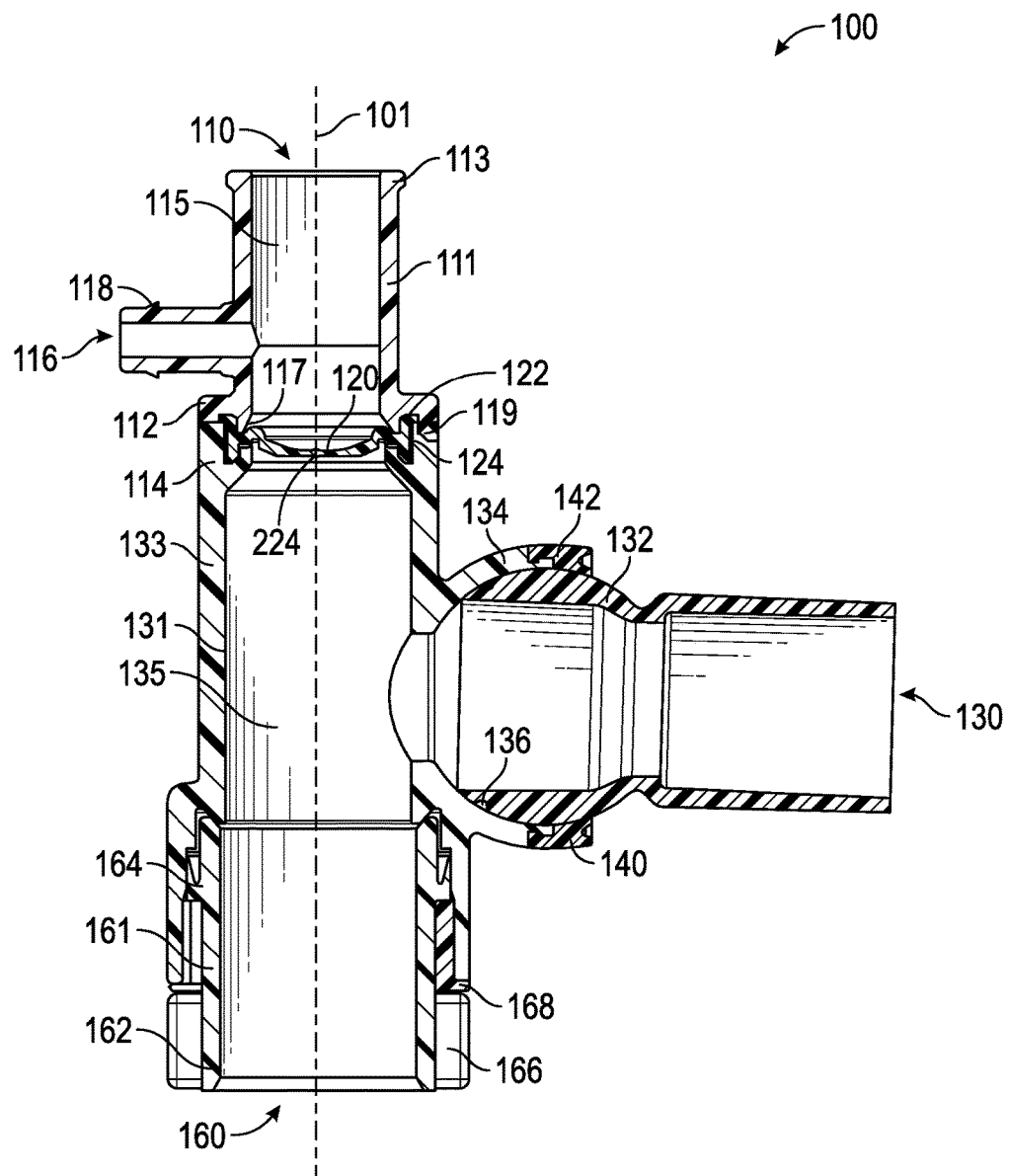
FIG. 3B illustrates a plan view of the example multiple-port airway adapter of FIG. 3A, in accordance with aspects of the present disclosure.
Figure 3C:
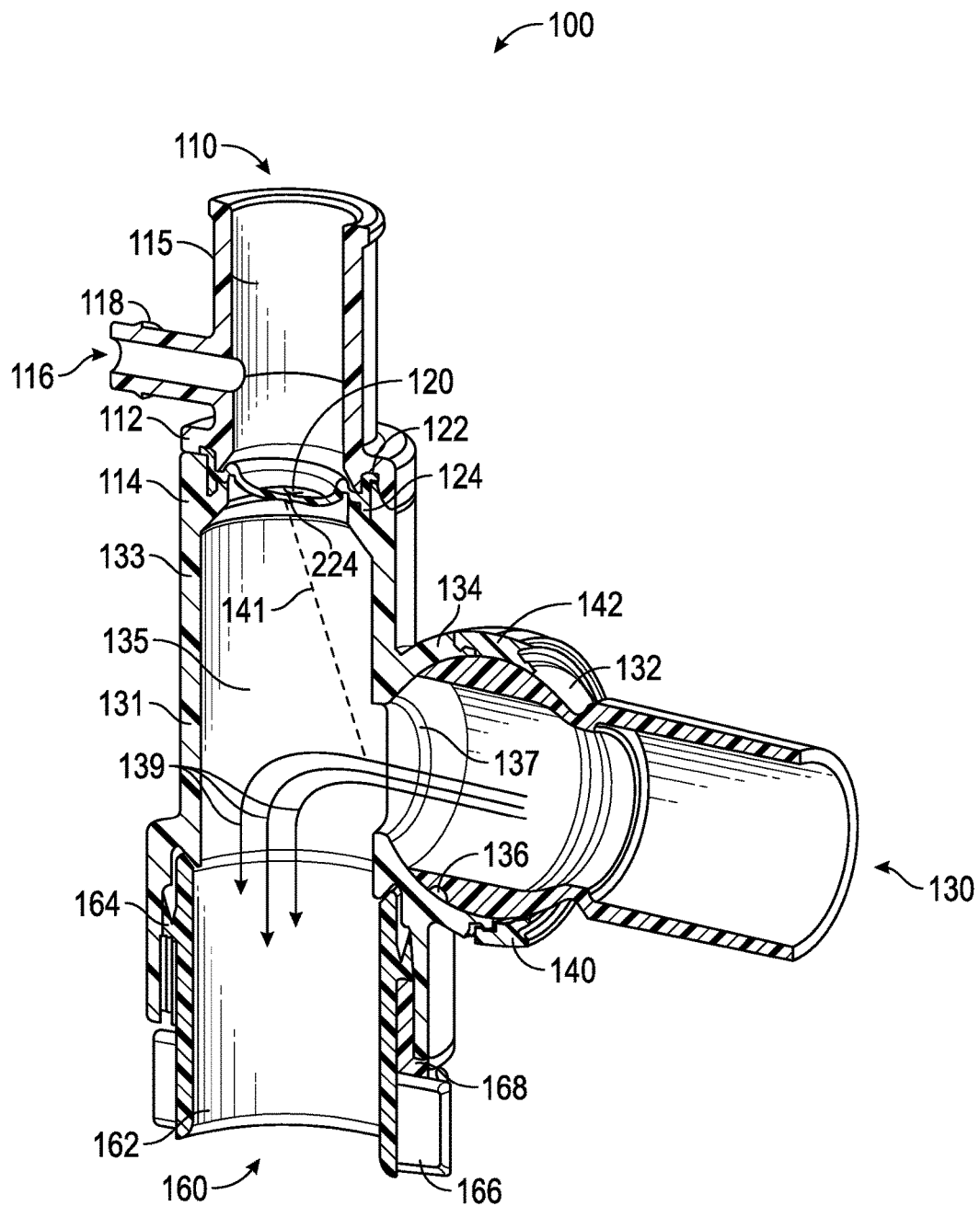
FIG. 3C illustrates a cross-sectional perspective view of the example multiple-port airway adapter of FIG. 3A, in accordance with aspects of the present disclosure.

FIGS. 3A-3C illustrate an example of a multiple-port airway adapter. In certain embodiments, airway adapter 100 may comprise connector body 111 having first end 113 configured to provide an access port 110 and second end 119. Connector body 111 may also include flush port 116 having a barbed surface 118 for engagement with certain implements such as caps, tubes, solution nozzles and the like (e.g., wash port coupling assembly 216). An elongate cavity 115 may be defined within the connector body 111 between the first end 113 and the second end 119. The flush port 116 is in fluid communication with the connector body to provide cleaning operations to be described in detail herein.

In some aspects, the elongate cavity 115 has an axial center 101 that extends throughout the interior of the connector body 111 between the first end 113 and the second end 119. In certain examples, the axial center 101 may extend through other portions of the airway adapter 100, such as a tubular portion 133 of ventilator base 131 and respiratory conduit 161.

In accordance with some aspects, connector body 111 may include lens 150 thereby providing magnified views into the elongate cavity 115 of the connector body 111. These magnified views may be beneficial, for example, so that a caregiver can read measurement indicators or other information provided on a suction catheter, tubing, or other medical implement that may be inserted through the access port 110. For example, a measurement reading on a 6 French tracheostomy-length catheter in a dimly lit neonatal-care room may be performed with ease and precision with airway adapter 100 comprising lens 150.

Valve 120 is positioned in airway adapter 100 to perform various function associated with the operation thereof. Valve 120 comprises a rim 123 having a first or leading edge 122 proximal to the first end 113 of connector body 111 and a second or trailing edge 124 distal from the first end 113. In this regard, valve 120 may be retained within the airway adapter 100 by a valve seat structure. In certain embodiments, the valve seat structure may be formed by a fused junction between connector body 111 and a tubular portion 133 of ventilation base 131. For example, the valve seat structure may comprise an upper circumferential surface 112 and a lower circumferential surface 114. Valve 120 may be positioned in the valve seat such that the upper circumferential surface 112 engages the leading edge 122 of the valve 120 and the lower circumferential surface 114 engages the trailing edge 124 of the valve 120. However, other valve seat structures are contemplated, for example, a rim receiving member within the connector body 111 proximal to the second end 119.

Airway adapter 100 may further comprise an articulable ventilator port 130 projecting from ventilation base 131. In certain embodiments, the ventilator port 130 is coupled to the ventilation chamber 135 and fluid pathway through a ball 132 and socket 134 connection. The first end of the ventilator port 130 may comprise the ball 132 portion of the articulable connection, while the socket 134 portion of the articulable connection may be disposed on the airway adapter 100 between the respiratory port 160 and the access port 110. In accordance with certain aspects, the ball 132 and socket 134 connection causes the ventilator port 130 to be articulable. In some embodiments, the ventilator port 130 can articulate (e.g., move, pivot, rotate, swivel, tilt, etc.) about a pivot point or one or more axes. In some embodiments, the ventilator port 130 can articulate about a joint or a joining portion.

The ventilator port 130 may be retained in the socket 134 by a capture ring 140. In certain embodiments, the capture ring 140 is disposed around the ventilator port 130 such that the ball 132 is retained in the socket 134 with the ventilator port 130 distally projecting from a fluid pathway. Because the capture ring 140 comprises at least a portion of an inner diameter that is less than the outer diameter of the ball 132, the ball 132 is firmly retained within the socket 134. Referring to FIGS. 3B-3C, the capture ring 140 may be coupled to the socket 134 by a barbed flange 142 and groove. The barbed flange 142 extends distally from the socket 134, while the capture ring 140 comprises a radial groove on an inner surface configured to receive the flange 142. In other embodiments, the capture ring 140 may be coupled using an interference fitting, threaded surfaces, adhesive, welding, combinations of these, or any other method typically used in the art.

Figure 3D:
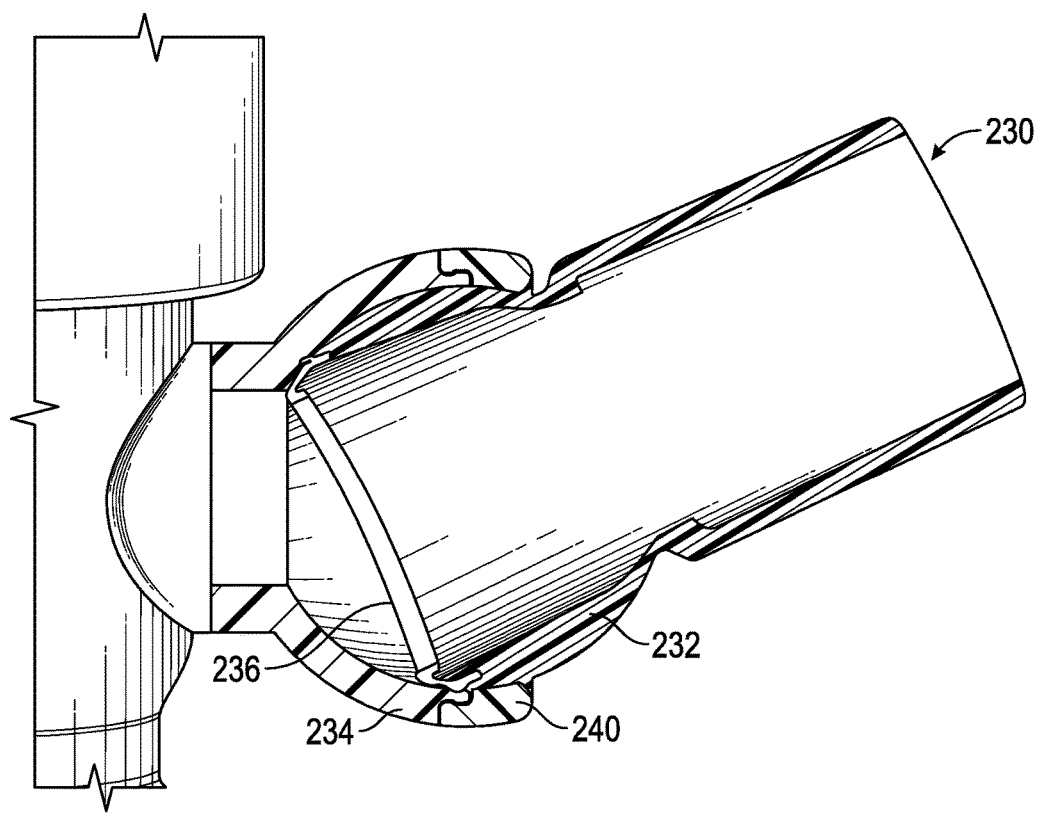
FIG. 3D illustrates a sectional view of an example of an articulable port, in accordance with aspects of the present disclosure.

The articulable connection may comprise a circumferential seal 136 disposed between the ball 132 and socket 134. The seal 136 may be retained within a circumferential groove on the exterior surface of the ball 132. The seal 136 limits fluid leakage from between the ball 132 and socket 134, and may contribute to the degree force or torque required to articulate the ventilator port 130. The force or torque to articulate the ventilator port 130 may be specified by selecting a seal 136 having particular characteristics, such as diameter, cross-sectional thickness, surface treatment, and hardness. For example, a seal having a large cross-sectional thickness will require an increase in force to articulate the ventilator port 130. In some embodiments, an interference fit between the capture ring 140 and the ball 132 may also contribute to the degree, force, or torque required to articulate the ventilator port 130. For example, a greater interference between the capture ring 140 and the ball 132 will produce a greater resistance to articulation, and a lesser interference would produce a lesser resistance. Referring to FIG. 3D, in some embodiments, the seal 236 may be incorporated into the exterior surface of the ball 232, or over-molded on the circumferential rim of the ball 232. In a further embodiment, the seal 136 may be disposed on an inner surface of the socket 234 and/or capture ring 240.

Figure 3E:
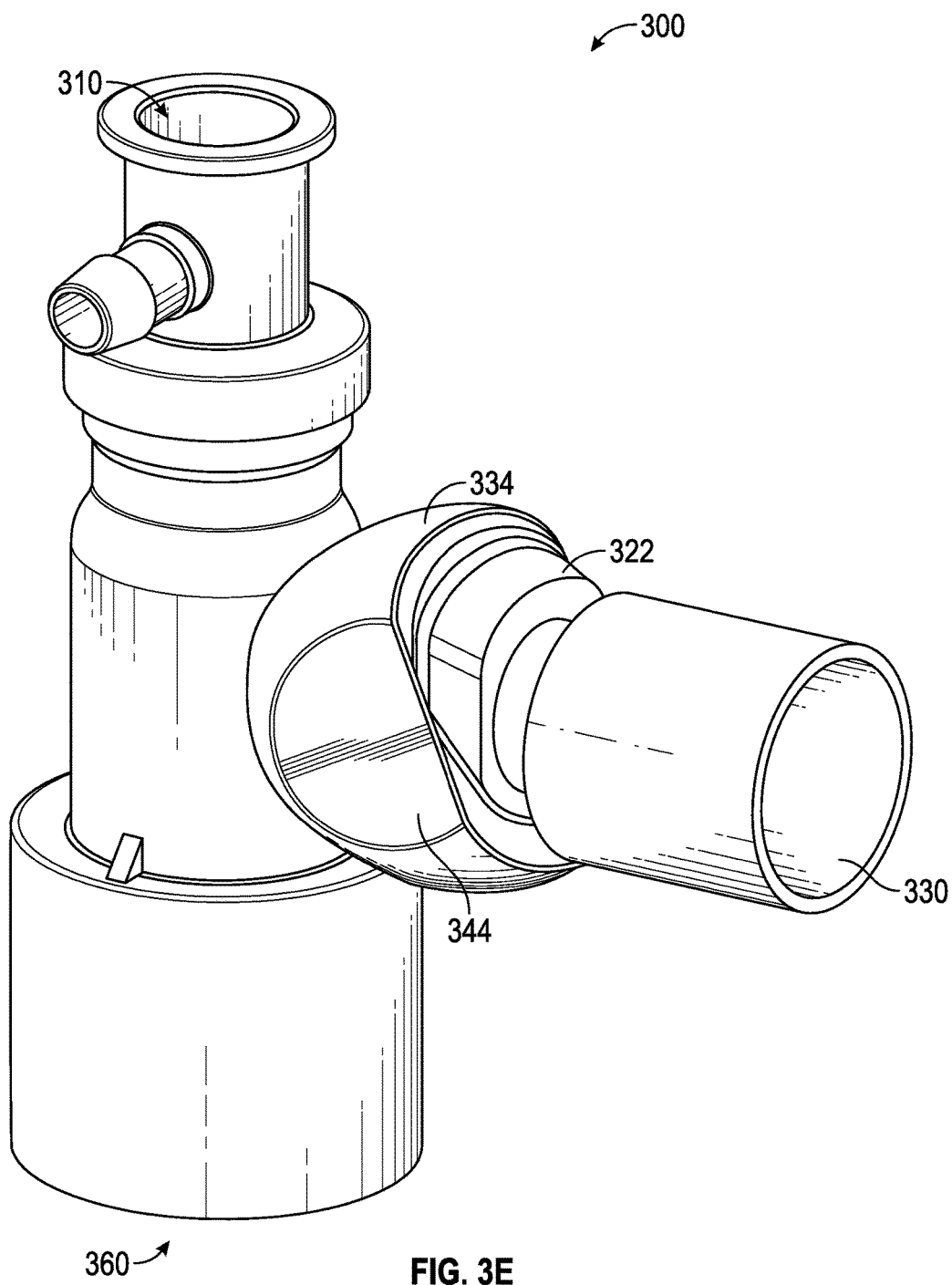
FIG. 3E illustrates a perspective view of an example of a multiple-port airway adapter, in accordance with aspects of the present disclosure.

Referring to FIG. 3E, in some embodiments, the ball 332 and socket 334 connection may comprise opposing flat sides 344 whereby excessive air space within the multiple-port airway adaptor 300 may be reduced or minimized. In applications such as neonatal respiratory care, it is important to reduce or minimize excessive air space within a breathing circuit. Where a ball 332 and socket 334 connection comprising flat sides 344 is utilized, a second ball and socket connection (not shown), axially rotatable port, or other articulable connection, may be incorporated adjacent to the first ball 332 and socket 334 connection to extend the range of articulation. By including more than one degree of freedom at the third port (e.g., by providing multiple ball 332 and socket 334 connections), the ventilator port 330 range of articulation may be increased compared with devices that are movable in only a single degree of freedom.

Figure 3F:
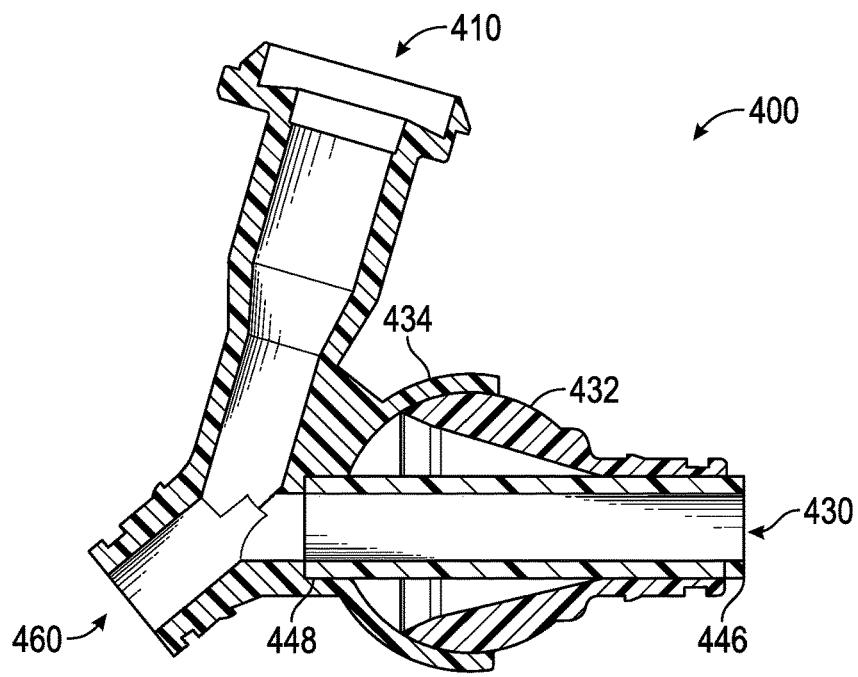
FIGS. 3F and 3G illustrate plan views of an example of a multiple-port airway adapter, in accordance with aspects of the present disclosure.
Figure 3G:
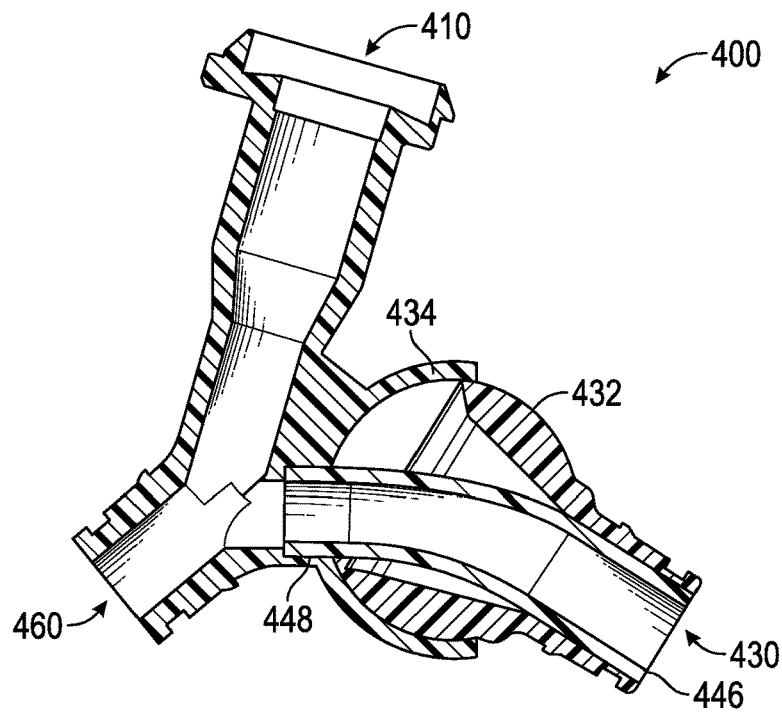

Referring to FIGS. 3F and 3G, in some embodiments, excessive air space within the multiple-port airway adaptor 400 may be minimized by disposing a flexible tube 446 having a lumen through the ventilator port 430 into the fluid pathway between the respiratory port 460 and the access port 410. By incorporating the flexible tube 446 through the ball 432 and socket 434 connection, the excessive air space created by the ball 432 and socket 434 connection is bypassed. A first end of the flexible tube 446 may be joined to the fluid pathway and a second end of the flexible tube 446 joined to the ventilator port 430. The flexible tube 446 may be joined to the multiple-port airway adaptor 400 using an adhesive, welding, friction fitting, or any other method typically used in the art. In some embodiments, each end of the flexible tube 446 is hermetically sealed to the multiple-port airway adaptor 400. Where the flexible tube 446 is joined at the fluid pathway, a ridge may be incorporated into the multiple-port airway adaptor 400 to create a seat 448. The seat 448 may improve the mechanical stability of the tube 446 during articulation. For example, an end of the flexible tube 446 may engage the seat 448 such that during articulation of the ventilator port 430, the end of the flexible tube 446 is pressed against the seat 448 to limit movement of the flexible tube 446 relative to the ventilator port 430. In some embodiments, the interior cross-section of the flexible tube 446 is selected to prevent undesired additional airflow resistance through the ventilator port 430. For example, the flexible tube 446 may have an interior lumen size that is equivalent to a lumen size of the fluid pathway between the respiratory port 460 and the access port 410, thereby limiting airflow resistance caused by discontinuities along the fluid pathway. Referring to FIG. 3G, with each end of the flexible tube 446 joined to the multiple-port airway adaptor 400, the flexible tube 446 may yield as the ventilator port 430 is articulated without becoming dislodged.

Figure 3H:
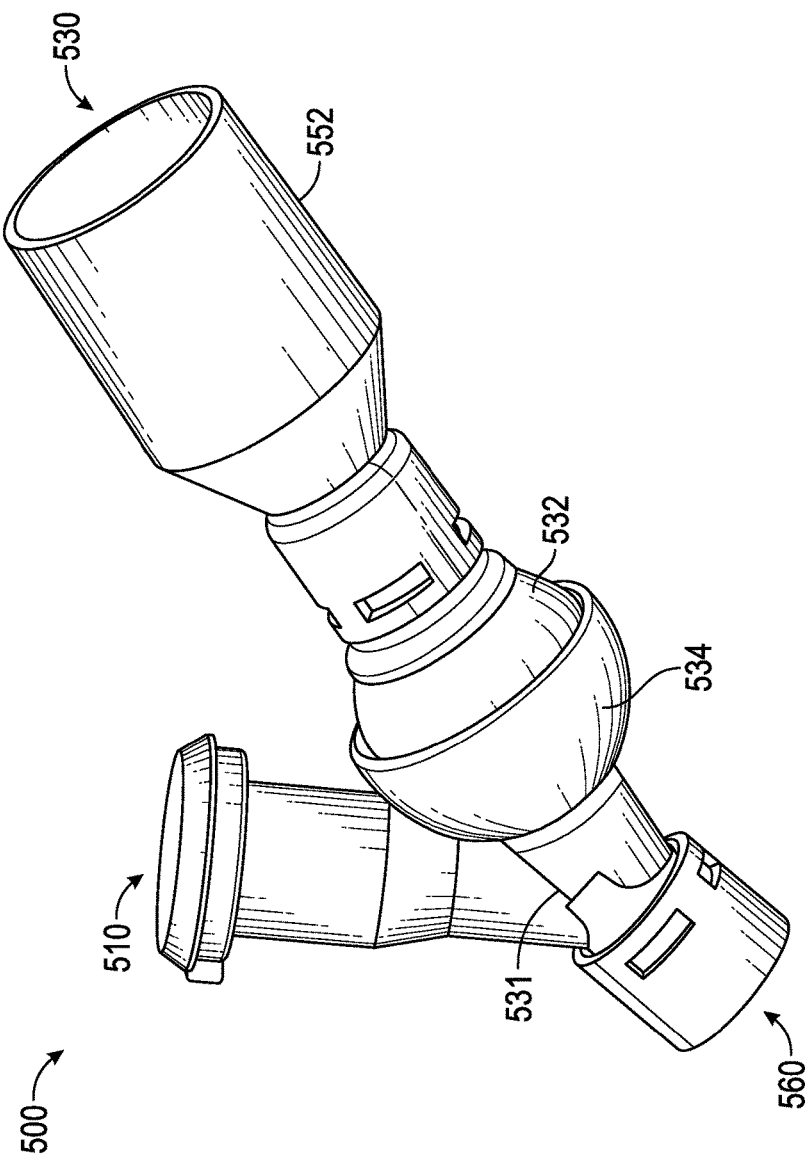
FIG. 3H illustrates a perspective view of an example of a multiple-port airway adapter, in accordance with aspects of the present disclosure.
Figure 3I:
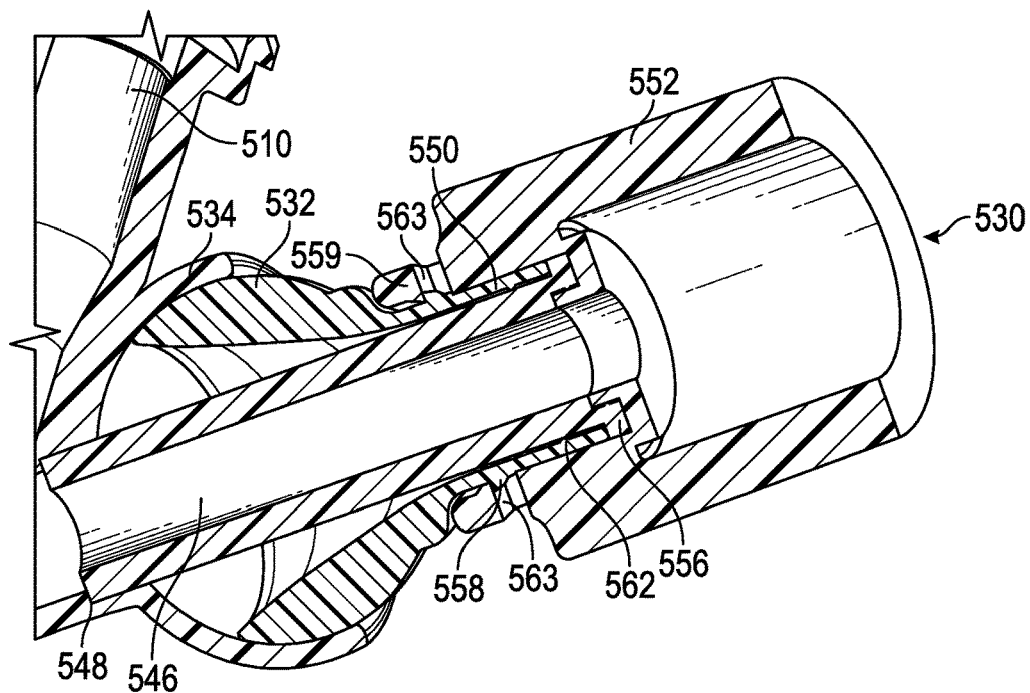
FIGS. 3I-3J illustrate detail views of the multiple-port airway adapter of FIG. 3H, in accordance with aspects of the present disclosure.
Figure 3J:
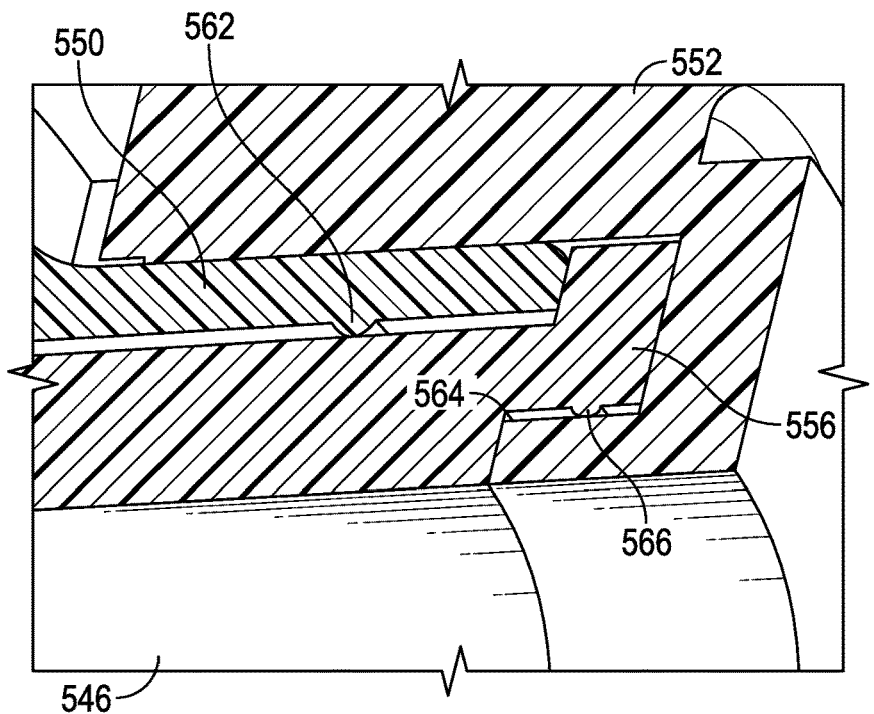
Figure 3J:
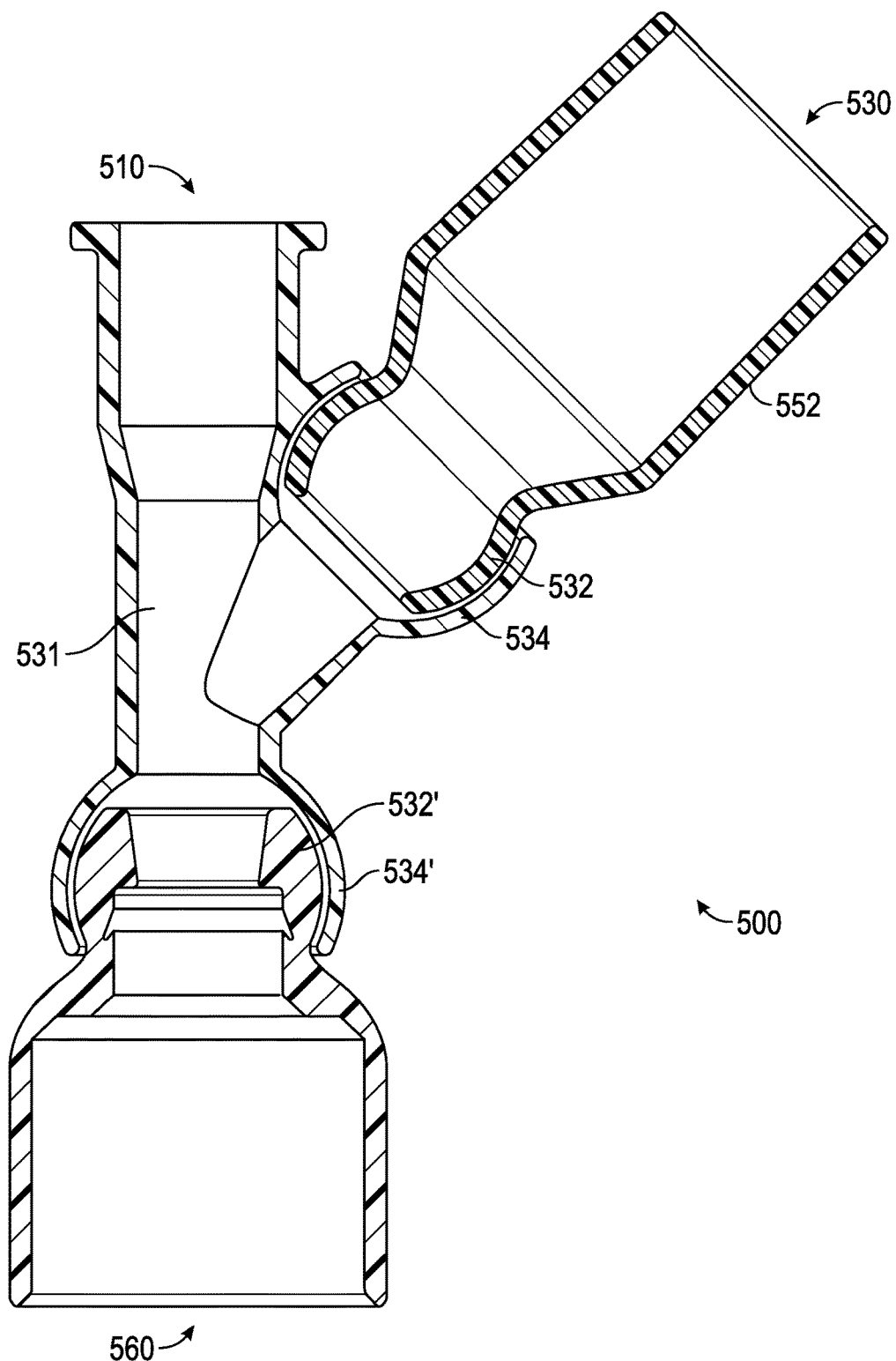

FIGS. 3H-3J illustrate an example of a multiple-port airway adapter 500. Aspects of the airway adapter 500 include, but are not limited to, a ventilator base 531 having an articulable ventilator port 530 projecting from ventilation base 531, an access port 510, and a respiratory port 560. A ball 532 and socket 534 connection permits articulation, including rotation, of the ventilator port 530.

Referring to FIG. 3I, the ventilator port 530 is formed on a first end by the ball 532 socket 534, and a second end by a cylindrical extension 550 protruding from the ball 532. A ventilator conduit coupler 552 is coupled to the ventilation base 531 through the ball 532 and socket 534 connection.

The socket 534 portion of the articulable connection is disposed on the airway adapter 500 between the respiratory port 560 and the access port 510. The socket 534 further includes a circumferential ridge forming a seat 548. The ball 532 of the ventilator port 530 is seated within the socket 534 with the cylindrical extension 550 protruding away from the socket 534. A lumen extends through the ball 532 and the cylindrical extension 550. The lumen tapers as it extends from the ball 532 toward the cylindrical extension 550. In some embodiments, the outer surface of the cylindrical extension 550 includes an undercut, groove, or radially extending circumferential ridge 558. In some embodiments, the inner surface of the cylindrical extension 550 includes a circumferential ridge 562 extending radially inward.

In an embodiment, the multiple-port airway adaptor 500 includes a flexible tube 546 having a lumen between a first end and an opposing second end. By incorporating the flexible tube 546 through the ball 532 and socket 534 connection, extra air space created by the ball 532 and socket 534 connection is separated from the flowpath of air through the adaptor 500 thereby reducing the amount of dead space in the adaptor 500. The flexible tube 546 provides a fluid pathway through the ventilator port 530 into the fluid pathway between the respiratory port 560 and the access port 510. The first end of the flexible tube 546 is disposed in the seat 548 of the socket 534, thereby improving the mechanical stability of the tube 446 during articulation of the ventilator port 530. The second end of the flexible tube 546 extends through the cylindrical extension 550. In some embodiments, a portion of the second end of the flexible tube protrudes beyond the cylindrical extension 550. In some embodiments, a flange 556 extends radially outward from the portion of the second end of the flexible tube 546 that protrudes beyond the cylindrical extension 550. Referring to FIG. 3J, in some aspects, the second end of the flange 556 includes a circumferential groove 564 extending radially outward from an inner surface of the flange 556. In yet other aspects, a circumferential ridge 566 extends radially inward from an inner surface of the circumferential groove 564.

In some aspects, the first end of the flexible tube 546 is bonded or glued to the seat 548, while the second end permits articulation, including rotation, of the ventilator port 530. For example, in some embodiments, the second end is not bonded to the seat. In some embodiments, a seal is provided by an interference fit between the circumferential ridge 562 of the cylindrical extension 550 and the outer surface of the flexible tube 546. In some embodiments, a seal is provided by the radially extending flange 556 of the flexible tube 546 as it engages the coupler. Where the ventilator port 530 comprises a ventilator conduit coupler 552, the flange 556 is retained between the end of the cylindrical extension 550 and the ventilator conduit coupler 552. In some aspects, the flange 556 is compressed between cylindrical extension 550 and the ventilator conduit coupler 552. However, the frictional force induced against the flange 556 is less than the force required to twist the flexible tube 546. Compression of the flange 556, in some instances, may be in the range of 5% to 33%. In some aspects, the flexible tube 546 is comprised of an elastomeric material having a hardness in the range of 60-90 Shore A. In some embodiments, a seal is provided by an interference fit between the circumferential ridge 566 of the flange and the ventilator conduit coupler 552.

The ventilator conduit coupler 552 is coupled to the ventilator port 530 by advancing the ventilator conduit coupler 552 onto the cylindrical extension 550. The ventilator conduit coupler 552 includes an inner surface having an inwardly extending ridge 559 that extends, in some embodiments, circumferentially along the inner surface of the coupler 552 adjacent a circumferentially extending channel. One or more window 563 inwardly extending ridge 559 extends through a wall of the coupler 552. The window 563 permits deflection of the ridge 559. As the ventilator conduit coupler 552 is advanced onto the cylindrical extension 550, the ridge 559 engages the circumferential ridge 558, such that one or both of the ridge 558 and the ridge 559 deflect to accommodate an interference fit. Upon further advancement, the ridge 559 bypasses the circumferential ridge 558, permitting the open end of the ventilator conduit coupler 552 to return to an undeflected position as the ridge 558 extends into the circumferentially extending channel. Because the ridge 559 extends radially inward from the inner surface of the coupler 552, the ventilator conduit coupler 552 may rotate independent of the cylindrical extension 550. In some embodiments, the ventilator conduit coupler 552 is coupled with the cylindrical extension 550 in such a way that rotation of one of either the airway adapter 500 or ventilator conduit coupler 552 causes rotation of cylindrical extension 550.

In some embodiments, the second end of the flexible tube 546 is not bonded to the cylindrical extension 550, and rotation of one of either the airway adapter 500, cylindrical extension 550, or ventilator conduit coupler 552 does not cause rotation of the flexible tube 546, thereby preventing twist or collapse of the flexible tube 546. A lubricant, such as a viscous silicone, may be applied to the flange 556 to further prevent twist or collapse of the flexible tube 546. In some embodiments, the flexible tube 546 is press-fit into or coupled with an interference fit with the inner surface of the ball 532 and cylindrical extension 500.

Referring to FIG. 3J', a multiple-port airway adapter 500 is illustrated. Aspects of the airway adapter 500 include, but are not limited to, a ventilator base 531 having an access port 510, an articulable ventilator port 530, and an articulable respiratory port 560. Each of the ventilator port 530 and respiratory port 560 include a ball 532 and socket 534 like that described in FIGS. 3H-3J. Specifically, a ball 532 and socket 534 connection permits articulation (e.g., move, pivot, rotate, swivel, tilt, etc.) of the ventilator port 530, and a ball 532' and socket 534' connection permits articulation of the respiratory port 560.

Figure 3K:
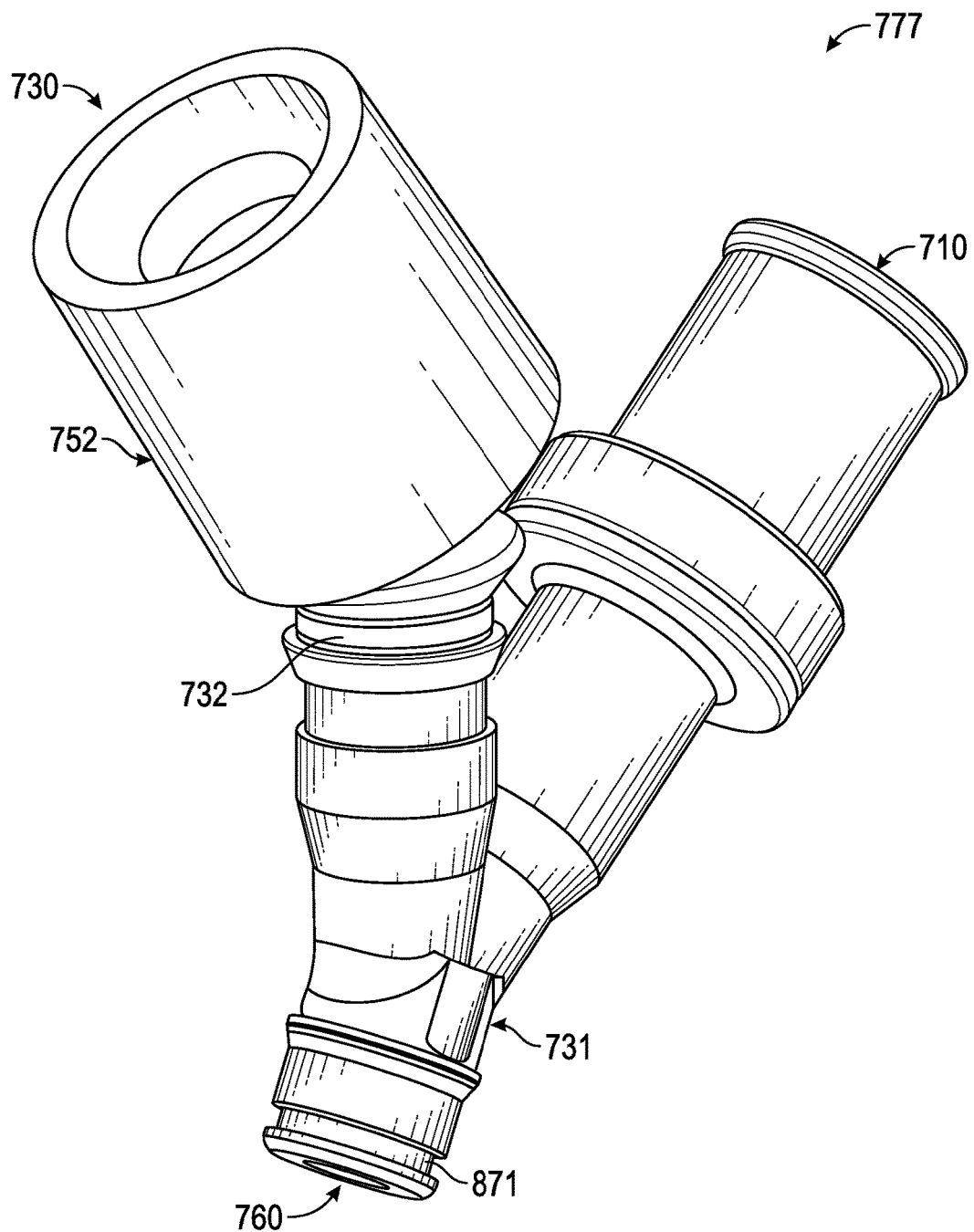
FIGS. 3K-3M illustrate a perspective views of examples of a multiple-port airway adapter, in accordance with aspects of the present disclosure.
Figure 3L:
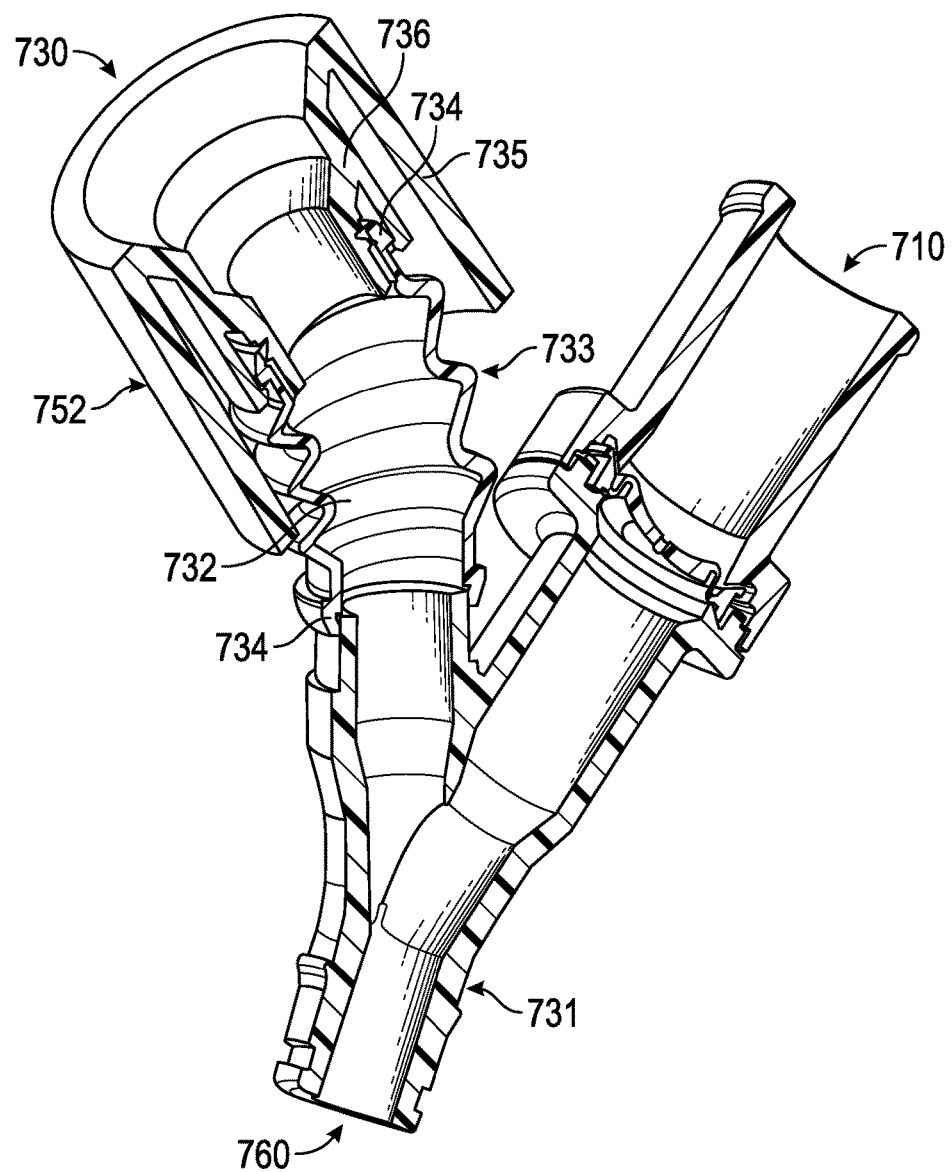
Figure 3M:
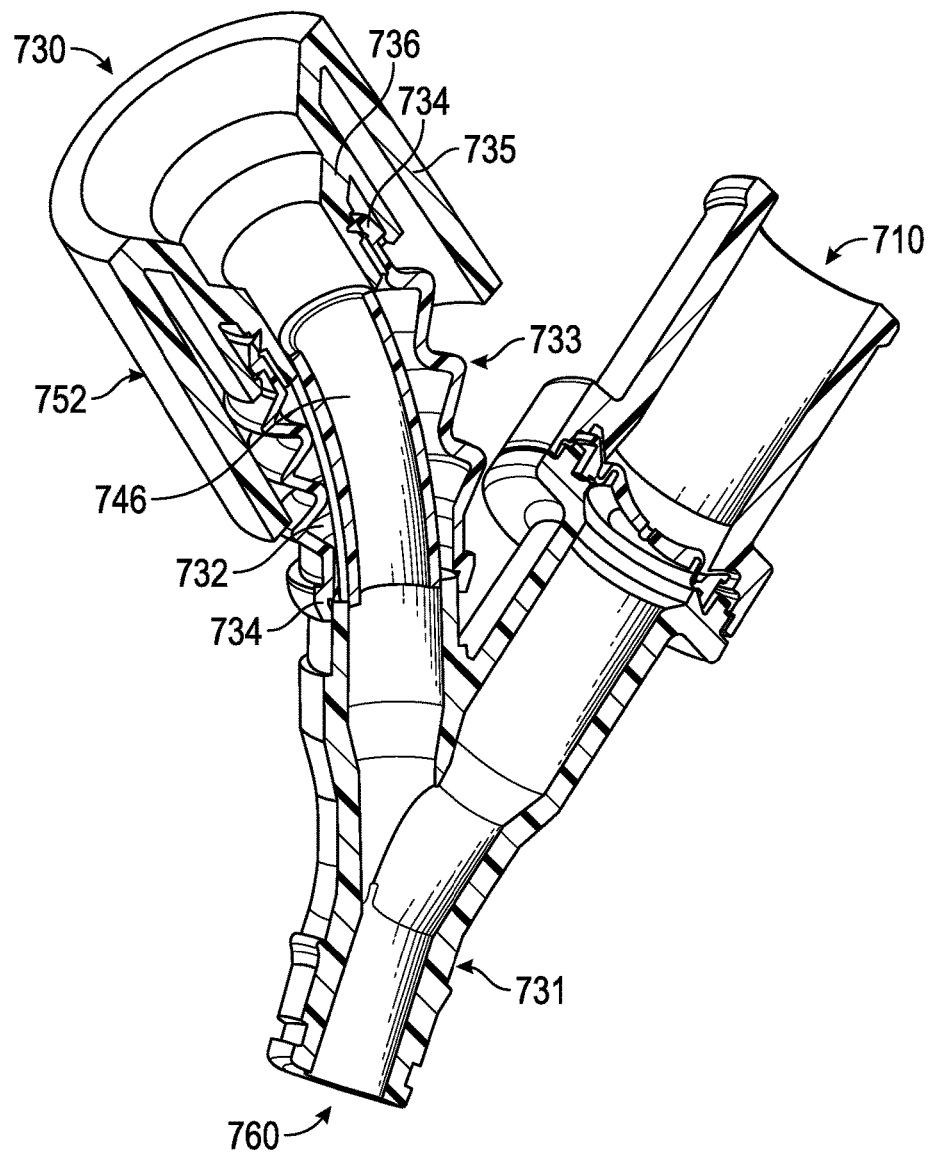

FIGS. 3K-3M illustrate an example of a multiple-port airway adapter 777. Aspects of the airway adapter 777 include, but are not limited to, a ventilator base 731 having an articulable ventilator port 730 projecting from the ventilation base 731, an access port 710, and a respiratory port 760. The ventilator port 730 includes a flexible conduit 732 coupled between a ventilator conduit coupler 752 and the ventilation base 731.

Referring to FIG. 3L, the flexible conduit 732 forms a lumen having a first end coupled to the ventilator base 731 and an opposing second end coupled to the ventilator conduit coupler 752. A portion of the lumen wall 733 between the first and second end includes alternating ridges and/or grooves, permitting the flexible conduit 732 to be articulated (e.g., move, pivot, rotate, swivel, tilt, etc.). For example, the lumen wall 733 may have a corrugated or popple shape, such as with popple tubing.

Figure 3N:
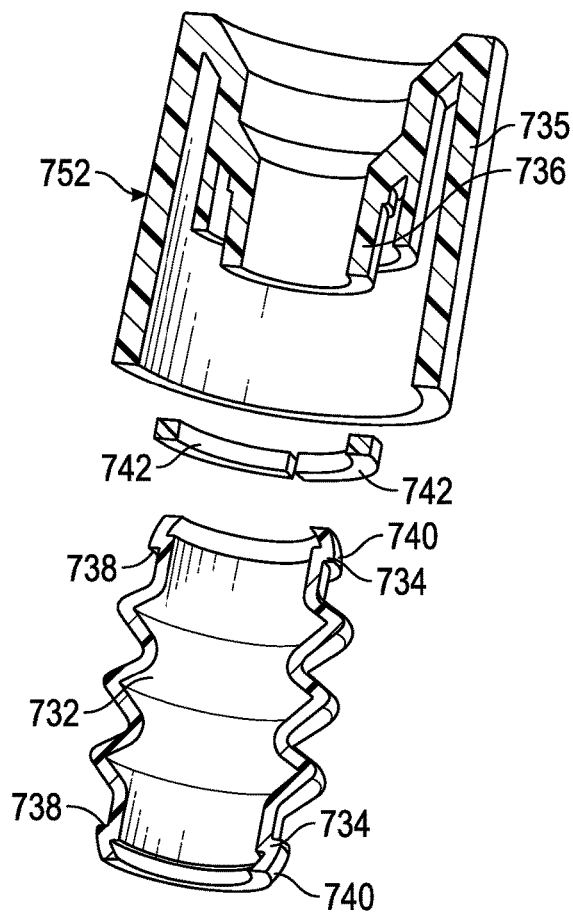
FIGS. 3N-3O illustrates a detail view of an example of an articulable port, in accordance with aspects of the present disclosure.
Figure 3O:
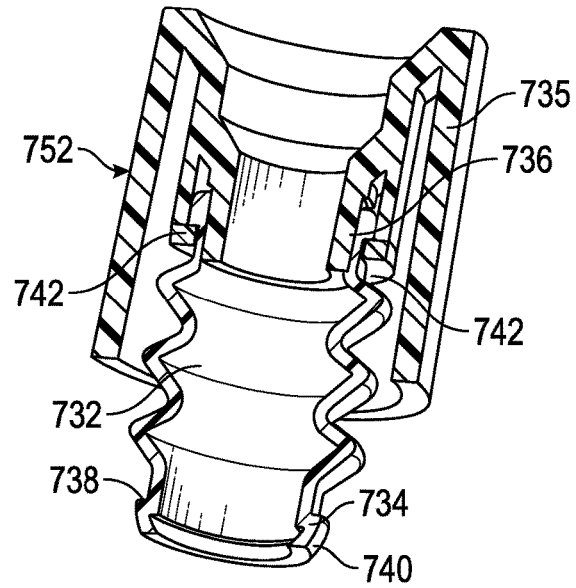

As illustrated in FIGS. 3N-3O, the first and second ends of the flexible conduit 732 form a compression flange 734. The compression flange 734 provides a seal between the flexible conduit 732 and the ventilator conduit coupler 752 while permitting the ventilator conduit coupler 752 to rotate with respect to the flexible conduit 732. In some aspects, only one end, for example, the second end comprises the compression flange 734. The flange 734 includes a ledge 738 that extends radially outward from the flexible conduit 732 and a ramped wall 740 that extends transversely from the ledge 738. In some embodiments, the compression flange 734 extends from an end, or inner surface, of the lumen wall 733 (FIGS. 3L-3M). In an embodiment, the ledge 738 extends radially outward with the ramped wall 740 biased radially inward toward an end of the flexible conduit 732.

The first end of the ventilator conduit coupler 752 is configured to couple with the second end of the flexible conduit 732, and the second end of the ventilator conduit coupler 752 is configured to couple with a ventilator conduit. The ventilator conduit coupler 752 forms a lumen having an outer wall 735 extending between a first end and a second end. An inner wall 736 extends from the second end toward the first end. In some aspects, the inner wall 736 tapers radially inward from the second end so that a portion of the inner wall 736 is radially spaced from the outer wall 735. In an example, the inner wall 736 extends a portion of the distance from the second end to the first end.

The ventilator conduit coupler 752 includes a circumferential channel configured to receive the second end of the flexible conduit 732. In some embodiments, the circumferential channel is formed between an inner surface of the outer wall 735 and an outer surface of the inner wall 736. In an embodiment, the circumferential channel is formed by the inner wall 736 and an intermediate wall between the inner wall 736 and the outer wall 735.

In some embodiments, such as the one illustrated in FIGS. 3L-3M, the circumferential channel includes opposing circumferential surfaces, each surface having a ridge. A first ridge extends radially inward toward the inner wall 736, and a second ridge on the opposing surface extends radially outward toward the outer wall 735. The first and second opposing ridges are axially spaced from each other. In other embodiments, such as the one illustrated in FIGS. 3N-3O, the circumferential channel comprises a ridge that extends radially outward toward the outer wall 735. In this embodiment, the compressible flange 734 is advanced into the circumferential channel and a retaining ring 742 is affixed around the flexible conduit 732. The retaining ring 742 abuts against the ledge 738 to compress the flange 734 between the retaining ring 742 and the ridge, thereby retaining the compressible flange 734 in the circumferential channel and creating a seal between the flexible conduit 732 and the ventilator conduit coupler 752. The retaining ring 742 may comprise one or more pieces, and may be coupled to or bonded to the ventilator conduit coupler 752.

Referring back to the embodiments of FIGS. 3L-3M, the second end of the flexible conduit 732 is coupled to the ventilator conduit coupler 752 by inserting the compression flange 734 into the circumferential channel. The compression flange 734 is advanced into the circumferential channel until the ramped wall 740 at the second end of the flexible conduit 732 engages the second ridge. Further advancement causes the ramped wall 740 to compress or bias so that the ledge 738 engages the first ridge. In some aspects, the distance between the first and the second ridges is less than the distance between the ramped wall 740 and ledge 738, thereby causing the compression flange 734 to remain biased within the circumferential channel.

In some aspects, the first end of the flexible conduit 732 is coupled to the ventilator port 730 portion of the ventilator base 731 by inserting the ventilator base 731 into the first end of the flexible conduit 732. The inner surface of the first end has a diameter that is equal to or slightly less than the outer surface of the ventilator base 731 to provide coupling by interference fit. In some aspects, the first end is bonded to the ventilator base 731 using an adhesive or mechanical attachment to prevent axial or rotational movement of the first end with respect to the ventilator base 731. In some embodiments, the ventilator base 731 can include a circumferential channel that receives the first end of the conduit.

Referring to FIG. 3M, the airway adapter 777 may include a flexible tube 746 having a lumen between a first end and an opposing second end. By incorporating the flexible tube 746 through the flexible conduit 732, extra air space created by the corrugated or popple shape flexible conduit 732 wall is bypassed, thereby reducing the amount of dead space in the adapter 777. The flexible tube 746 provides a fluid pathway through flexible conduit 732. The first end of the flexible tube 746 is inserted into the ventilator port 730 passage of the ventilator base 731, and the second end is inserted into the passage formed by inner wall 736 of the ventilator conduit coupler 752. Each respective end of the flexible tube 746 has an outer surface diameter that is equal to or slightly larger than the inside diameter of the ventilator base 731 and the ventilator conduit coupler 752. In some embodiments, an end of the flexible tube 746 is retained in the seat like that illustrated in FIG. 3I. To permit the ventilator conduit coupler 752 to rotate with respect to the flexible conduit 732, and to prevent the flexible tube 746 from twisting or collapsing, the first end of the flexible tube may be bonded or glued to the ventilator base 731 while the second end is permitted to rotate within the ventilator conduit coupler 752.

Figure 3P:
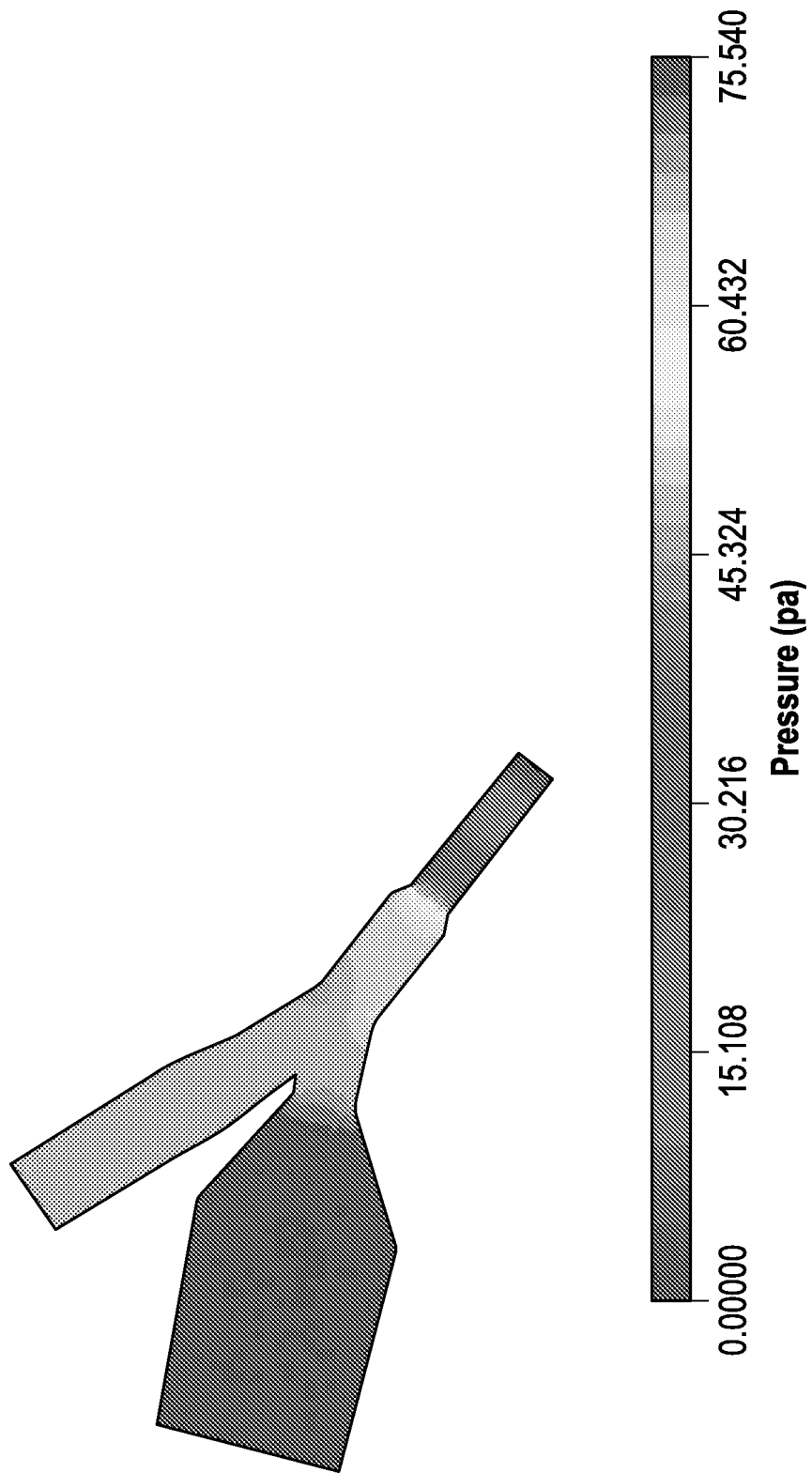
FIG. 3P illustrates a simulation of an example of a multiple-port airway adapter, in accordance with aspects of the present disclosure.

FIG. 3P illustrates a simulation indicating the pressure drop of flow through the airway adapter 777 of FIGS. 3K-3M. The features disclosed herein to reduce excessive air space and to provide minimal resistance to flow through the airway adapter 777 results in a pressure drop of less than 100 Pa.

Figure 3Q:
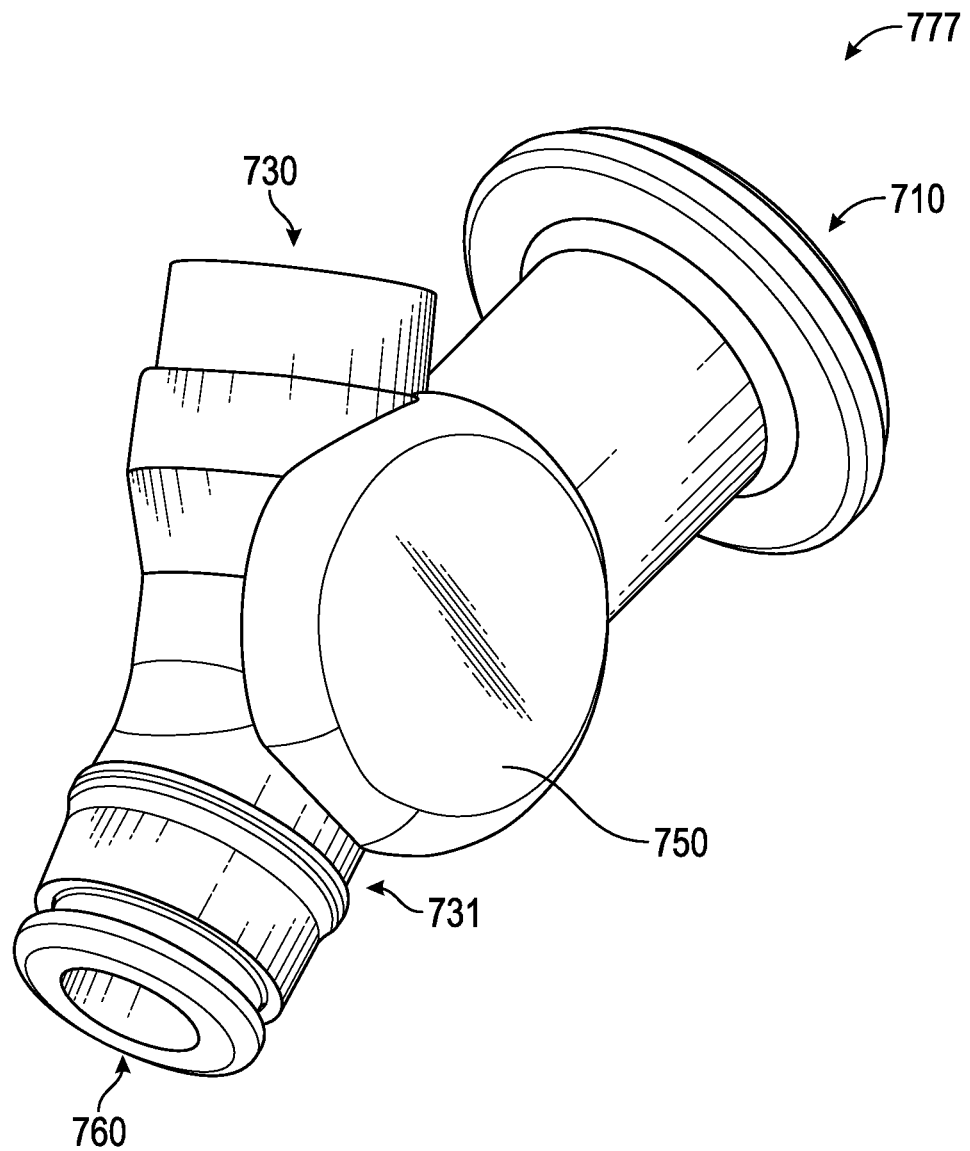
FIG. 3Q illustrates a perspective view of an example of a multiple-port airway adapter, in accordance with aspects of the present disclosure.

Referring to FIG. 3Q, aspects of the airway adapter 777 includes a lens 750 to permit visibility into the airway adapter 777. For example, a caregiver may read measurement indicators or other information provided on a suction catheter, tubing, or other medical implement inserted through the airway adapter 777. In some embodiments, the lens 750 is disposed through an outer surface of the ventilator base 731, between the respiratory port 760, ventilator port 730 and access port 110. In some embodiments, the lens 750 is convex to produce a magnified view into the ventilator base 731.

Figure 3R:
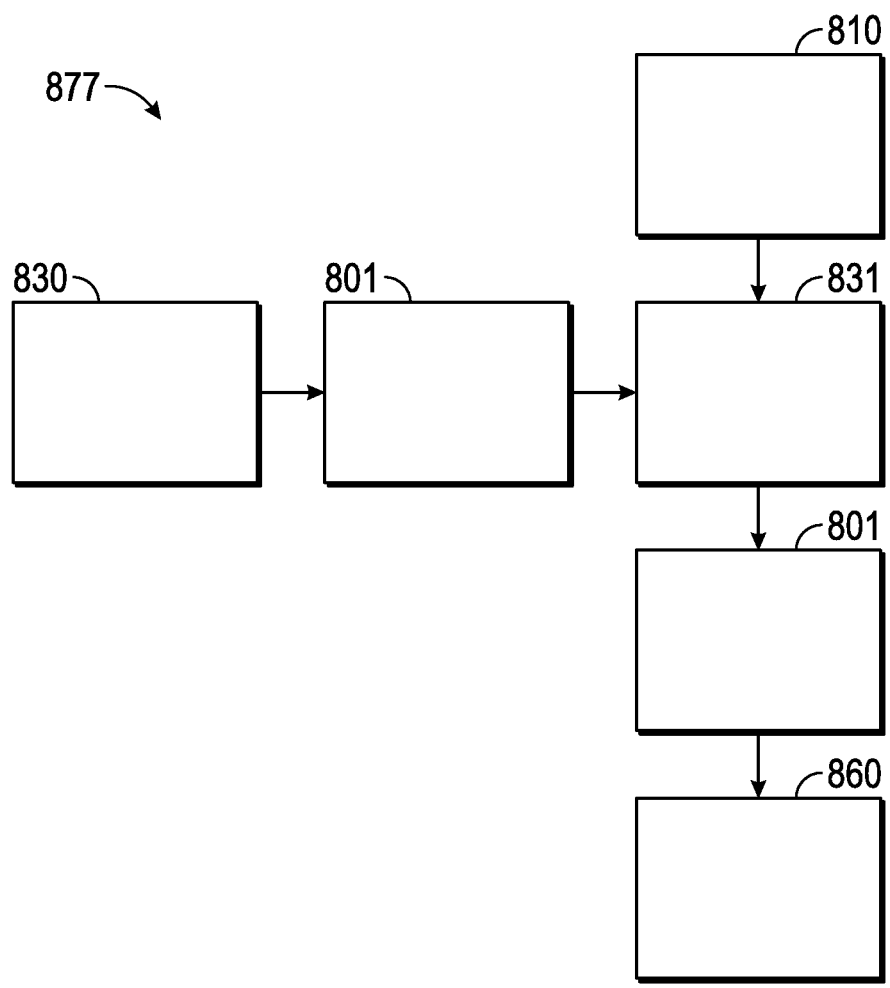
FIG. 3R illustrates a schematic diagram of an example of a multiple-port airway adapter, in accordance with aspects of the present disclosure.

FIG. 3R illustrates a schematic diagram of an airway adapter 877 including, but not limited to, a ventilator base 831, an access port 810, a ventilator port 830, and a respiratory port 860. The ventilator port 830 and respiratory port 860 each include a flexible connector 801 to permit articulation (e.g., move, pivot, rotate, swivel, tilt, etc.) with respect to the ventilator base 831.

Figure 3T:
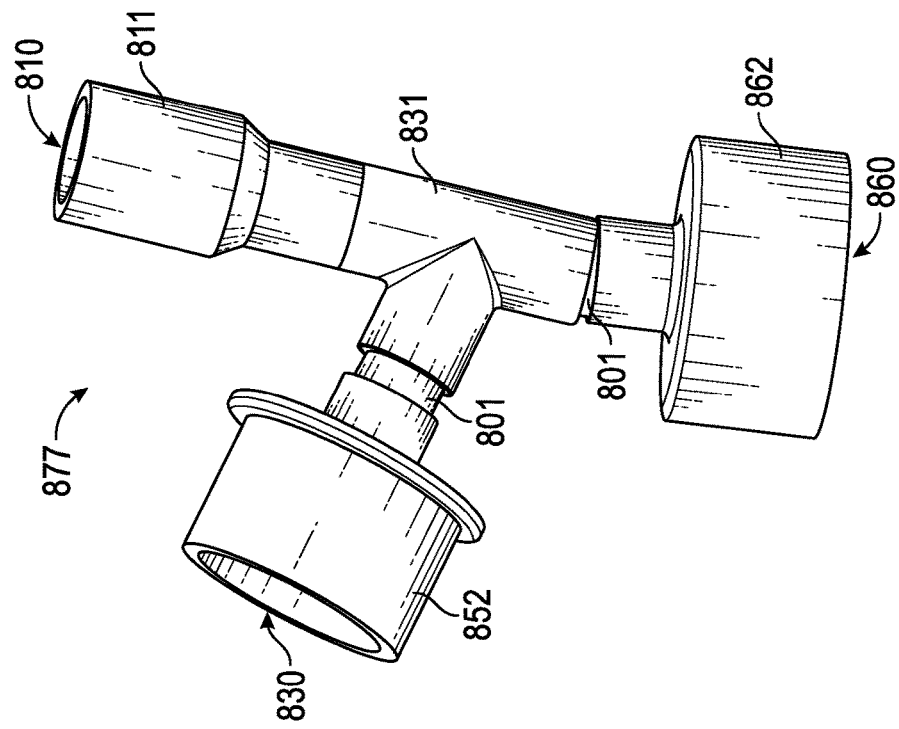
FIGS. 3S-3U illustrate a perspective views of examples of a multiple-port airway adapter, in accordance with aspects of the present disclosure.
Figure 3S:
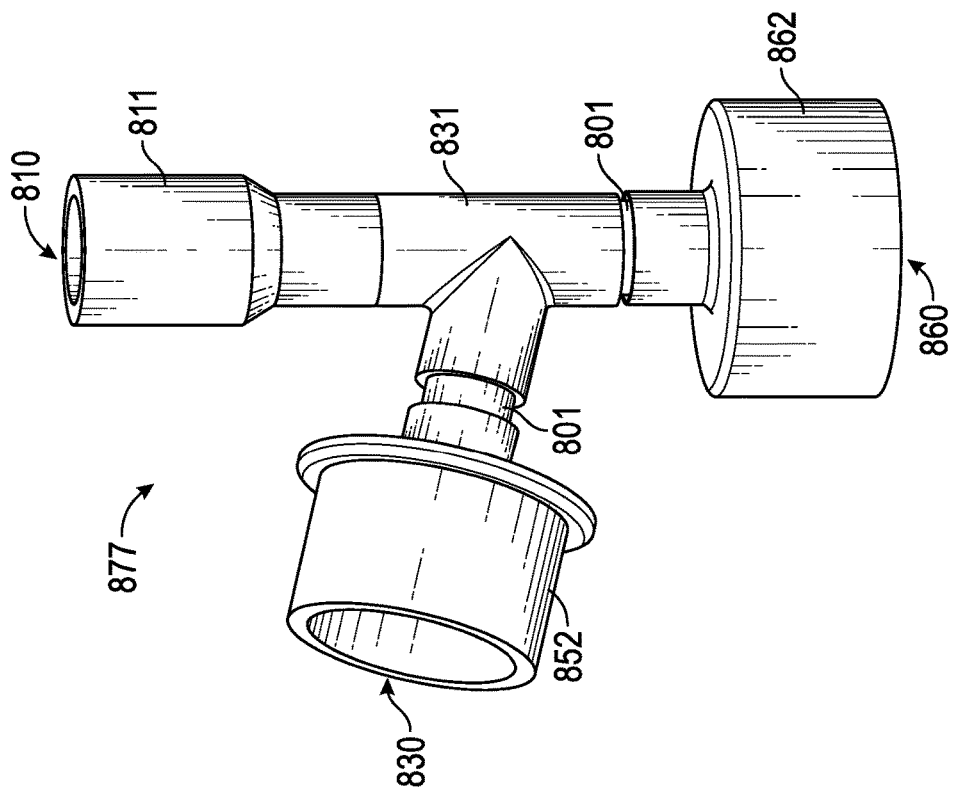

FIGS. 3S-3T illustrate an embodiment of an airway adapter 877 with a ventilator base 831 having an access port 810 comprising a connector body 811. The adapter 877 also includes a ventilator port 830, comprising a ventilator conduit coupler 852, and a respiratory port 860, comprising a respiratory conduit coupler 862. In some embodiments, one or more of the ventilator conduit coupler 852 and the respiratory conduit coupler 862 comprises a flexible connector 801 that connects the one or more couplers 852, 862 to the ventilator base 831. In some embodiments, both the ventilator conduit coupler 852 and the respiratory conduit coupler 862 comprise a flexible connector 801 that connects the respective coupler with the base 831. The flexible connectors 801 permit the ventilator conduit coupler 852, and/or the respiratory conduit coupler 862 to articulate with respect to the ventilator base 831.

The flexible connector 801 may comprise a resilient material such as an elastomer forming a lumen between a first end and an opposing second end. The first end of the flexible connector 801 is coupled to the ventilator base 831 and the second end of the flexible connector 801 is coupled to an adapter or device, for example, the ventilator conduit coupler 852 or the respiratory conduit coupler 862. In some embodiments, a portion of the first end of the flexible connector 801 is inserted into the ventilator base 831 and a portion of the second end of the flexible connector 801 is inserted into an adapter or device so that an exposed length of flexible connector 801 remains. The distance between the ventilator base 831 and the adapter or device is determinative of the degree or range of articulation. The range of articulation increases as the exposed length of flexible connector 801 increases, and the range of articulation decreases as the exposed length of the flexible connector 801 decreases. In some aspects, the range of articulation is limited by contact between the ventilator base 831 and the adapter or device. For example, if airway adapter 877 is disturbed while the respiratory port 860 is coupled to a patient's artificial airway 165 (FIG. 1A), the ventilator base 831 will articulate, thereby limiting translation of the disturbance to the patient. Articulation of the airway adapter 877 will be limited when the ventilator base 831 and the respiratory conduit coupler 862 engage each other as best illustrated in FIG. 3T.

Figure 3U:
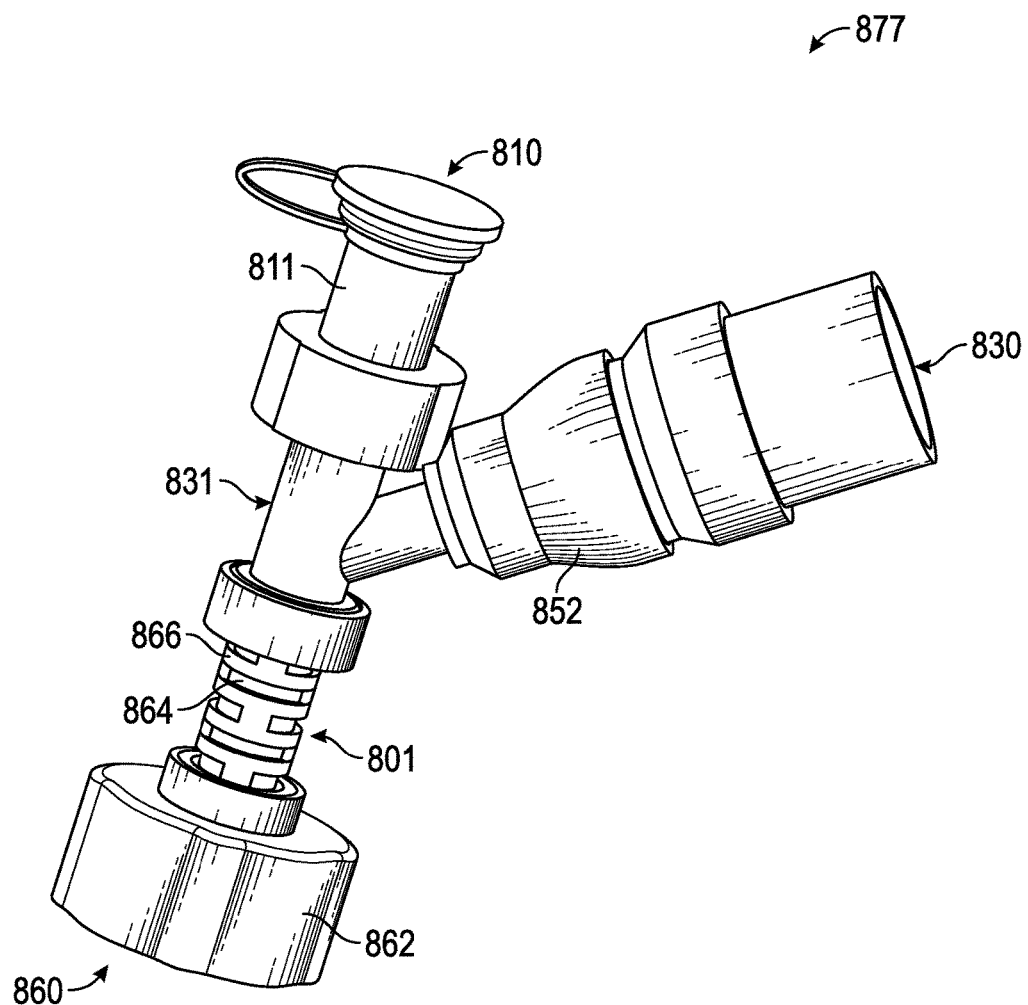

FIG. 3U illustrates embodiments of an airway adapter 877 like those depicted in FIGS. 3S-3T. The airway adapter 877 includes ventilator base 831 having an access port 810 comprising a connector body 811, a ventilator port 830 comprising a ventilator conduit coupler 852, and a respiratory port 860 comprising a respiratory conduit coupler 862. In some embodiments, a port of the airway adapter 877 includes a flexible connector 801. In some aspects, the respiratory conduit coupler 862 is connected to the base 831 by the flexible connector 801. The flexible connector 801 comprises a first layer 864 surrounded by a second layer 866. The first layer 864 forms a lumen between a first end and an opposing second end. The second layer 866 surrounds the outer surface of the first layer 864 between the first and second ends.

In some embodiments, the first layer 864 and the second layer 866 comprise different characteristics. In some aspects, the first layer 864 comprises a resilient material that permits elastic deformation, and the second layer 866 comprises a ductile material that permits plastic deformation. In some for example, the first layer 864 may include resilient elastomer such as rubber, while the second layer may include a ductile metal such as copper.

Because the second layer 866 may be less resilient or flexible than the first layer 864, the second layer 866 includes features to accommodate articulation of the flexible connector 801. The features of the second layer 866 include, but are not limited to, grooves, notches, channels, or interspaced channels passages through the wall of the second layer 866. In some embodiments, the flexible connector 801 permits the airway adapter 877 to remain in the articulated position, while in other embodiments the combined materials permit temporary articulation before causing the flexible connector 801 to return to a neutral state.

Figure 3V:
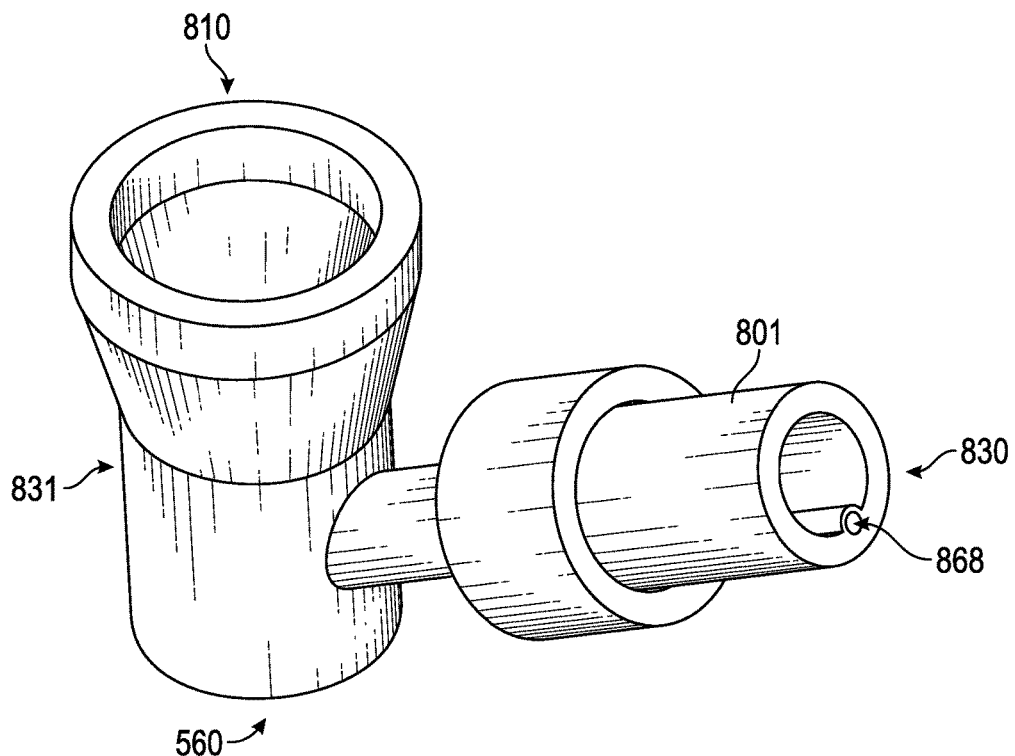
FIGS. 3V-3X illustrates detail views of an example of an articulable port, in accordance with aspects of the present disclosure.
Figure 3W:
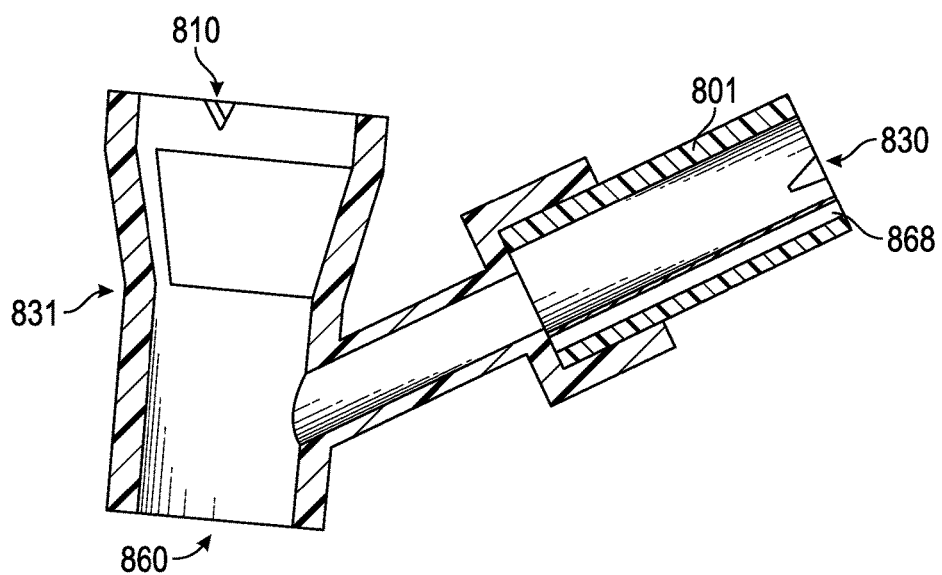
Figure 3X:
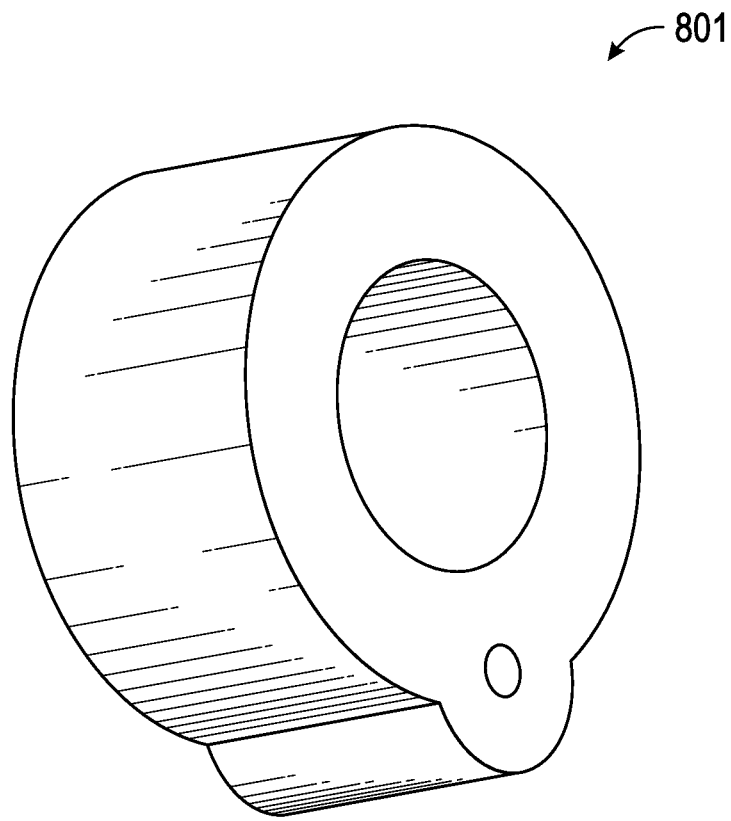

The embodiment of FIGS. 3V-3X illustrate an embodiment of a flexible connector 801 coupled to the ventilator port 830 of an airway adapter 877. The flexible connector 801 permits the ventilator port 830 to be articulated and remain in the articulated position. Although illustrated as coupled to the ventilator port 830, the flexible connector 801 may be coupled to any port on the airway adapter 877.

The flexible connector 801 includes a lumen between a first end and an opposing second end. The flexible connector 801 includes a first, resilient material, and a second, ductile, material. In some embodiments, the second material is distributed with the first material between the first and second ends. For example, the second material may be disposed along and inner or outer surface of the lumen, or may be embedded in a wall of the lumen. In another example, the second material is embedded into the wall as the lumen is extruded. In the illustrated embodiment, the wall of the lumen includes a passage between the first and second ends wherein the second material is a wire disposed within the passage. Referring to FIGS. 3V-3W, a portion of the inner surface of the wall is raised to accommodate the passage and wire the first and second end. Referring to FIG. 3X, a portion of the outer surface of the wall is raised to accommodate the passage and wire the first and second end.

Referring back to the embodiments of FIGS. 3A-3C, the respiratory port 160 is configured for fluid connection to an artificial airway 165 (FIG. 1A) otherwise establishing a direct connection to the patient's respiratory tract. For example, the respiratory port 160 can be fluidly connected to an endotracheal tube or a tracheostomy tube. The respiratory port 160 includes an annular swivel connector 162, allowing the multiple-port airway adapter 100 to rotate, with respect to the swivel connector 162, about the fluid pathway axis. The swivel connector 162 comprises a circumferential flange 164 that extends radially from the outer surface. When the swivel connector 162 is coupled to the multiple-port airway adapter 100, the flange engages the inner surface of the fluid pathway.

Referring to FIG. 1A, the swivel connector 162 may be coupled to a patient's artificial airway 165. The swivel connector 162 may be rotated in either direction to further assist with coupling the respiratory port 160 while minimizing or reducing disruption, discomfort, or trauma to the patient. The tubing of a ventilation device (not shown) may be coupled with the ventilator port 130. Because the ventilator port 130 is articulable, the ventilation device may be coupled or relocated without applying additional force on the multiple-port airway adapter 100 or artificial airway of the patient.

The multiple-port airway adapter 100 may further include an intermediate ring 168 disposed around the circumference of swivel connector 162. The intermediate ring 168 may abut against flange 164, preventing or limiting translational movement of the swivel connector 162 along the fluid pathway axis (e.g., axial center 101), yet allowing the swivel connector 162 to rotate about the fluid pathway axis. Moreover, respiratory conduit 161 may comprise transversely extending protrusions 166 on an exterior surface. In some aspects, the protrusions 166 provide additional rotational leverage when coupling or de-coupling the respiratory port 160 with an artificial airway (e.g., an intubated patient's ETT or tracheostomy tube). In some embodiments, the protrusions 166 may extend outward and parallel to each other, and in some embodiments, the protrusions 166 may extend radially outward. In some embodiments, the swivel connector 162 can provide one or more depressions (not shown) that permit additional gripping capacity by a user of the swivel connector 162. For example, a series of dimples may be disposed around the circumference of the swivel connector 162 outer surface. In some embodiments, the portion of the swivel connector 162 not inserted into the fluid pathway 146 is at least one-eighth inch in length. In accordance with certain aspects, valve 120 is configured such that it provides a substantial fluid barrier between the elongate cavity 115 of connector body 111 and the ventilation chamber 135 of ventilation base 131. Valve 120 may be positioned for biasing or spring action such that a generally concave side of the valve 120 is positioned facing the elongate cavity 115 side (e.g., catheter insertion or vacuum suction side), and a generally convex side of the valve 120 is positioned facing the ventilation chamber 135 side.

Ventilation base 131 may be configured as a manifold structure including a connection to the respiratory conduit 161 and a ventilation source opening 137. The ventilation source opening 137 is fluidly coupled to the tubular portion 133 of the ventilation base 131 and the respiratory conduit 161. To be discussed in more detail later in the disclosure, valve 120 comprises a primary seal and secondary seal that are designed to provide a substantial fluid barrier at low pressure differentials (e.g., below 68 cm $H_2O$).

As can be seen with reference to FIG. 3C, valve 120 is disposed adjacent to an end of the tubular portion 133 with respect to the longitudinal alignment of the tubular portion 133 in the ventilation base 131. In this regard, the valve 120 is disposed such that the valve is not located in a direct fluid pathway 139 from the ventilation source opening 137 and the respiratory conduit 161, for example, when a ventilator is operatively coupled to the ventilator port 130 of the airway adapter 100. Accordingly, the valve 120 may be positioned a distance 141 (e.g., between 6 mm and 12 mm) from the ventilation source opening 137. The positioning of the valve 120 with respect to the direct fluid pathway 139 is one of several factors that may be considered when configuring the valve 120 to operate at a low initial cracking pressure for the secondary valve.

Figure 4:
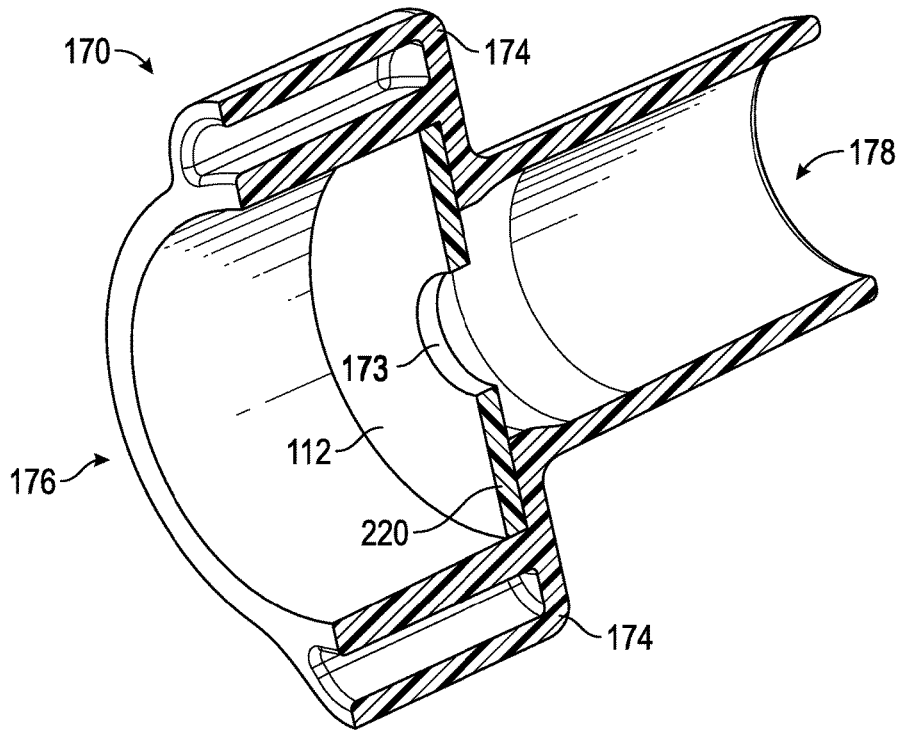
FIG. 4 illustrates a cross-sectional perspective view of an example an airway adapter coupler, in accordance with aspects of the present disclosure.

FIG. 4 illustrates an example of an airway adapter coupler 170. With reference to the example airway adapter 100 of FIG. 3B, airway adapter coupler 170 can be coupled to the first end 113 of connector body 111. In certain embodiments, airway adapter coupler 170 comprises a wiper seal 172 having an inward flange and an access aperture 173. In some aspects, the inward flange of the wiper seal 172 may comprise a transverse wall with respect to the axial center 101. However, in other embodiments, the inward flange can be angled with respect to the axial center 101. For example, the inward flange may be angled toward the second end 119 of the connector body 111 thereby forming a frustoconical wiper seal or frictional member when coupled to the access port 110 of the airway adapter 100. Moreover, the wiper seal 172 and associated aperture size can be configured to receive a suction catheter or other medical implement for accessing the elongate cavity 115 of the connector body 111. It is to be understood that in certain embodiments, airway adapter coupler 170 is connected to a suction catheter sheath and can removably coupled to the first end 113 of connector body 111 of the airway adapter 100.

Figure 5:
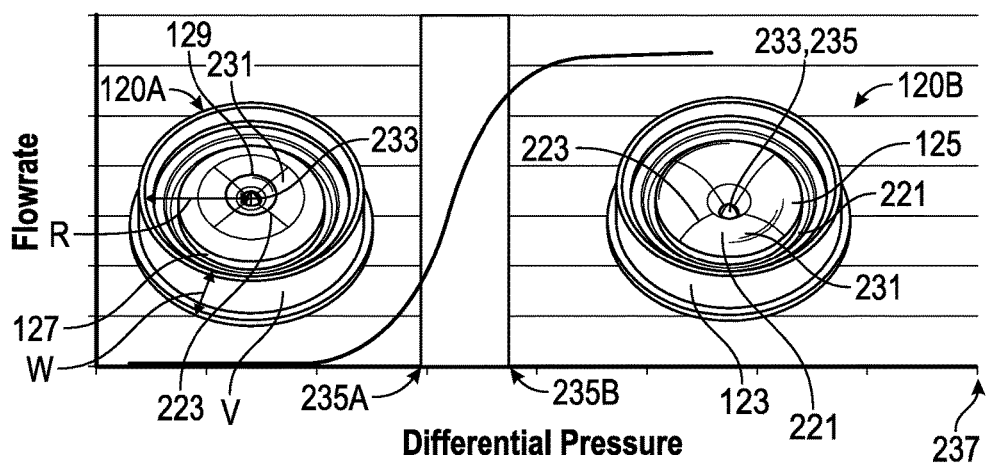
FIG. 5 illustrates perspective views of an example of a multiple-purpose valve, along with a chart of example seal cracking pressures, in accordance with aspects of the present disclosure.

FIG. 5 illustrates an example of a multiple-purpose valve. In accordance with certain embodiments, valve 120 comprises a rim 123 along an outer circumferential section. However, in other embodiments, the rim of a multiple-purpose valve can be various shapes (e.g., oval, square, hexagonal, pentagonal, etc.). Valve 120 also comprises a diaphragm section 125 that is resiliently flexible in accordance with certain embodiments. The diaphragm section 125 is integrally connected to the rim 123 and comprises a plurality of valve segments 221 defined by one or more slits 223 (see additional aspects related to the valve segments 221 and one or more slits 223 is illustrated in FIGS. 6A-6F and 6K-6N).

In certain embodiments, a valve segment 221 may include a first region 225 and a second region 227. A primary seal 231 of the valve 120 is formed by the plurality of valve segments 221 disposed on the diaphragm section 125. Valve 120 also includes a secondary seal 233. The secondary seal 233 is formed by an arrangement of one or more first regions 225 of the valve segments 221. In this regard, the primary seal 231 refers to a larger seal of the valve 120 for allowing a suction catheter (or other medical implement) to pass therethrough. After the suction catheter has been removed, the primary seal 231 to returns to its original unbiased configuration. The secondary seal 233 of the valve 120 refers to a small seal (e.g., a smaller seal than the primary seal 231) for allowing and regulating an amount of air (generally a small amount) from the ventilation chamber 135 to enter into the elongate cavity 115 so as to clean the suction catheter after it has been retrieved from the artificial airway 165 or the patient's airway. Accordingly, the secondary seal 233 of valve 120 acts as an air-entrainment valve in accordance with certain aspects.

As illustrated in the chart of FIG. 5, valve 120 is configured to withstand a certain amount of differential pressure and maintain a seal above atmospheric pressure. The secondary seal 233 has a first cracking pressure 235, and the primary seal 231 has a second cracking (or breaching) pressure different from the first cracking pressure 235. Valve 120 may be configured such that the first cracking pressure may be defined within a range between the lower threshold 235a and the upper threshold 235b as illustrated in the chart of FIG. 5 (for illustration purposes; not drawn to scale). In certain implementations, a lower threshold 235a may be established at approximately 68 cm $H_2O$, and an upper threshold 235b may be established at approximately 188 cm $H_2O$. Accordingly, valve 120 may be configured such that air-entrainment may be accomplished between the range of the lower threshold 235a and the upper threshold 235b, proximal to the lower threshold 235a in some implementations. For example, a suction catheter positioned in the elongate cavity 115 of the connector body 111 providing 120 cm $H_2O$ of vacuum pressure with the first cracking pressure 235 range may cause the secondary seal 233 to be breached in a controlled manner such that air-entrainment into the elongated cavity 115 may be performed while minimally affecting (if at all) the ventilation function occurring between the ventilator port 130 and the respiratory port 160. Moreover, it is to be understood that in certain embodiments, the second cracking/breaching pressure 237 of the primary seal 231 may be significantly larger than the first cracking pressure 235 range such that suctioning or vacuum pressure differentials will not have a meaningful effect on the primary seal 231. In this regard, the cracking or breaching associated with the entirety of the primary seal 231 of valve 120 may be caused by insertion of a medical implement therethrough and are associated with the cleaning and scraping functions of the valve 120, in accordance with certain embodiments.

Under normal operation of a mechanical ventilation breathing circuit (e.g., ventilation source applied at the ventilator port 130 directed to artificial airway 165 via respiratory port 160 by airway adapter 100), the differential pressure at valve 120 of airway adapter 100 remains below the first cracking pressure 235. At this low range of differential pressure, an effect of such differential pressure on valve 120 in operation will appear as valve 120a.

When a suction force is applied at the access port 110, when the valve 120 is not physically breached by a medical implement (e.g., suction from a suction catheter with the tip end of the suction catheter in the elongate cavity 115 of the connector body 111), the differential pressure at the valve 120 will be at or above the first cracking pressure 235, but below the second cracking pressure 237, in accordance with certain embodiments. At this differential pressure range, the effect of such differential pressure during operation of artificial airway 100 will cause valve 120 to appear as valve 120b having the secondary seal 233 breached.

Accordingly, effective air-entrainment may be accomplished. It is to be understood that a greater force (e.g., a frictional force of a medical implement being passed through valve 120) may be required to breach the primary seal 231, which can be viewed as extending a circumferential area on the diaphragm section 125 of valve 120 having a diameter of the one or more slits 223. However, it is pertinent to note that valve 120 is configured such that an expected suction force or range of suction forces does not cause a breach of the primary seal 231, as such a breach during air-entrainment would have an undesirably adverse effect on the patient's respiratory function by removing too much air from the ventilation source.

In accordance with certain aspects, the diaphragm section 125 of valve 120 may include a ramped area 127 and a segment area 129. The ramped area 127 (e.g., frustoconical, rounded, raised, etc.) may function as a biasing mechanism to aid in returning the valve 120 to the original sealed configuration after a suction catheter or other medical implement has been removed. Moreover, in some aspects, the one or more slits 223 arranged on the diaphragm section 125 to form the plurality of valve segments 221 may be entirely disposed on the segment area 129. The segment area 129 may be substantially flat or plateaued in relation to the ramped area 127; however it is understood that variations in thickness of the diaphragm section 125 within the segment area 129 exist from the first regions 225 and the second regions 227 of the valve segments 221 that form aspects of the primary seal 231 and the secondary seal 233.

As illustrated in the examples of FIG. 5, the rim 123 of valve 120 may be circumferential and have a width (W) that is less than a radius (R) of the rim 123. In this regard, the width (W) of the rim 123 can define a volume (V) of the valve 120 than can be viewed as drum-shaped. The width (W) of the rim 123 may be of sufficient width such that when the valve 120 is retained in a valve retention structure of the airway adapter 100, a sufficiently air tight seal can be achieve. However, one of many distinguishing features of valve 120 can be understood with respect to the drum-shaped volume described. For instance, although diaphragm section 125 may include ramped area 127 in certain embodiments, the ramped area 127 may not extend to a duck-bill type configuration at least with respect to some embodiments of the valve. Thus, in certain embodiments, the ramped area 127 and segment area 129 of the diaphragm section 125 may be disposed within the drum volume (V) by the width (W) of the rim 123 when the valve is in an unbiased configuration (e.g., when the no differential pressure is applied to the valve 120 and the rim 123 is not compressed in a valve retention structure). Accordingly, certain embodiments of valve 120 can be seen as substantially planar, and thereby the plurality of valve segments can be extendable into both sides or zones to which the valve 120 serves as a breachable barrier or seal.

Moreover, although various materials may be used in creating or forming valve 120 in accordance with aspects of the present disclosure, the rim 123 and diaphragm section 125 may comprise one of polysilicone, polyurethane, or polythermoplastic elastomer, in certain embodiments.

FIGS. 6A-6F and 6K-6N illustrate non-limiting examples of multiple-purpose valves. In accordance with various aspects, valve segments 221 of valve 120 may include one or more first regions 225 and one or more second regions 227. In accordance with certain aspects, the primary seal 231 of valve 120 may be formed by the plurality of valve segments 221, and the secondary seal of valve 120 may be formed by an arrangement of the one or more first regions 225 of the one or more valve segments 221. The one or more first regions 225 may comprise a gradient thickness on at least a portion of the one or more first regions 225. For example, with additional reference to the cross-section views in the examples of FIGS. 6G and 6H, a first thickness 125A of a first region 225 may be defined proximal to or at an intersection of the one or more slits 223, and a second thickness 125B may be defined proximal to or at a transition or border of the secondary seal 233 (e.g., FIGS. 6A, 6E, and 6F). The second thickness 125B is greater than the first thickness 125A in accordance with certain aspects. The variation in thickness permits the valve 120 to comprise a varying reaction to air pressure (e.g, cracking pressure) and interaction with a medical implement being passed through valve 120 (e.g, a suction catheter).

The valve segments 221 include a first surface proximal to the leading edge 122 of the valve 120, and a second surface distal from the leading edge 122 of the valve 120. The first surface comprises a first radius R2, and the second surface comprises second radius R4. In some embodiments, the first radius R2 and the second radius R4 are not equal. In an embodiment, for example, embodiment illustrated in FIGS. 6M-6N, the first radius R2 may be in the range of 0.1332 to 0.1628 inches, and the second radius R4 may be in the range of 0.3555 to 0.4345 inches. In an embodiment, the first radius R2 is 0.148 inches and the second radius R4 is 0.395 inches.

Figure 6A:
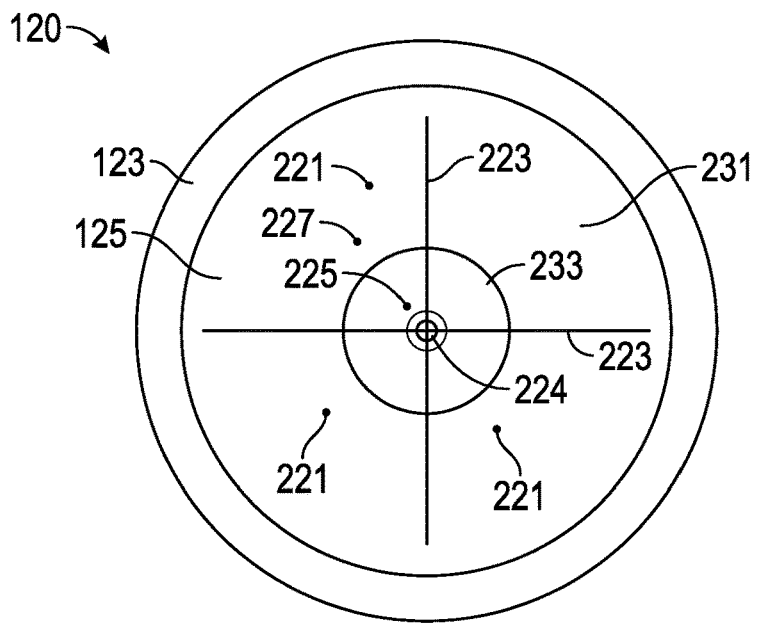
FIGS. 6A-6F illustrate plan views of examples of multiple-purpose valves, in accordance with aspects of the present disclosure.
Figure 6B:
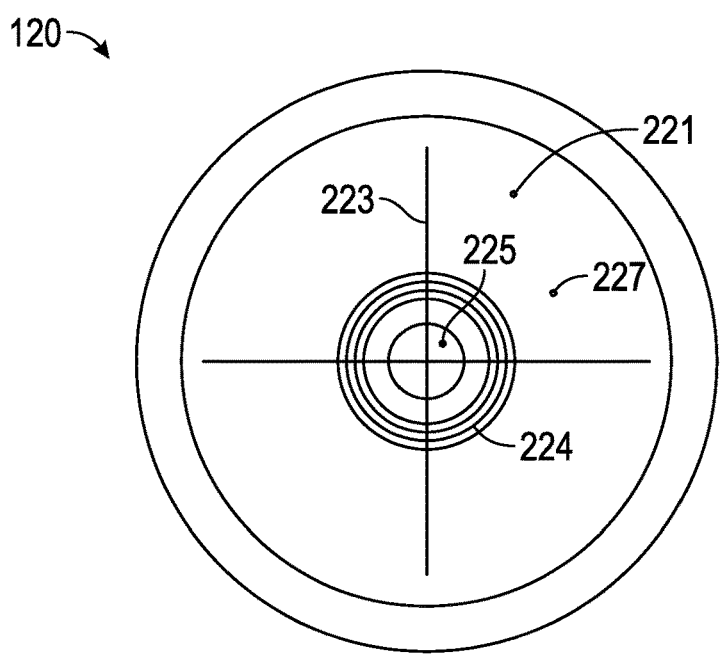
Figure 6C:
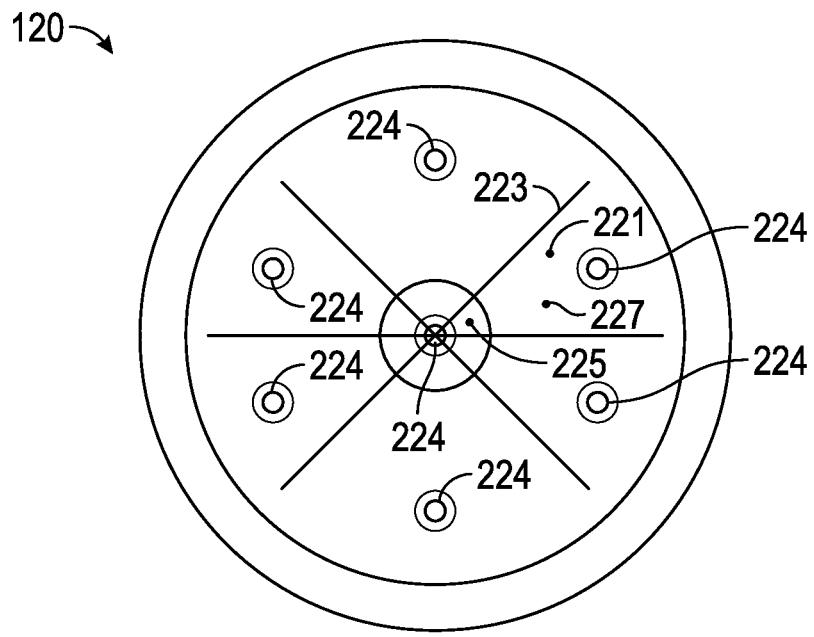
Figure 6D:
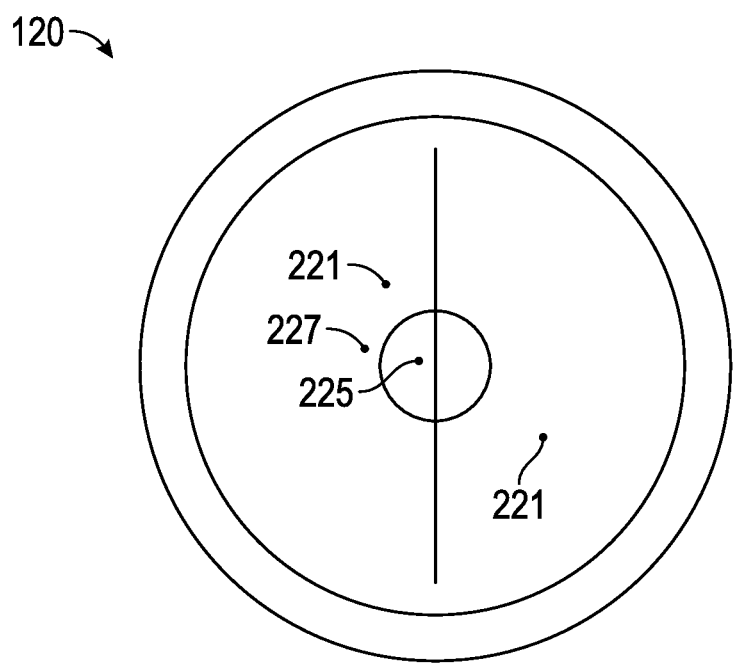
Figure 6E:
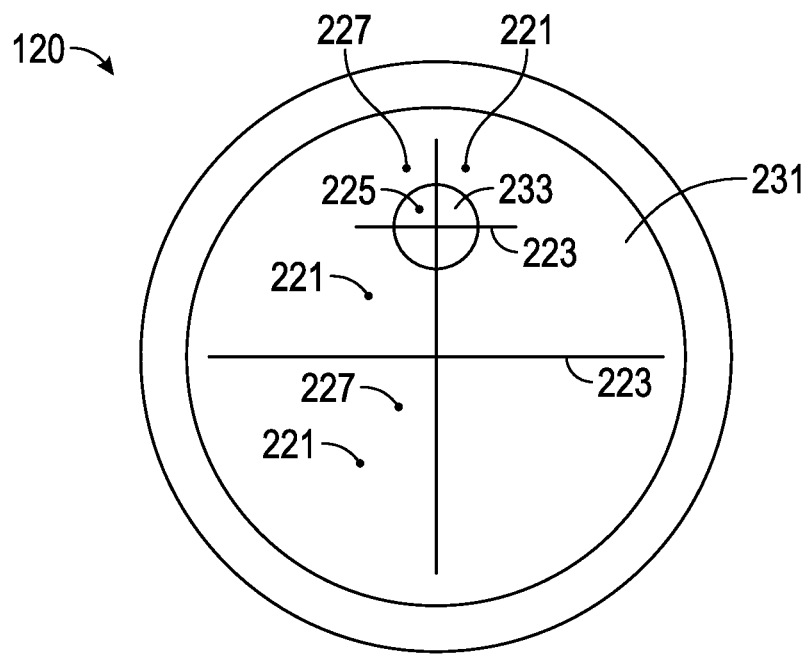
Figure 6F:
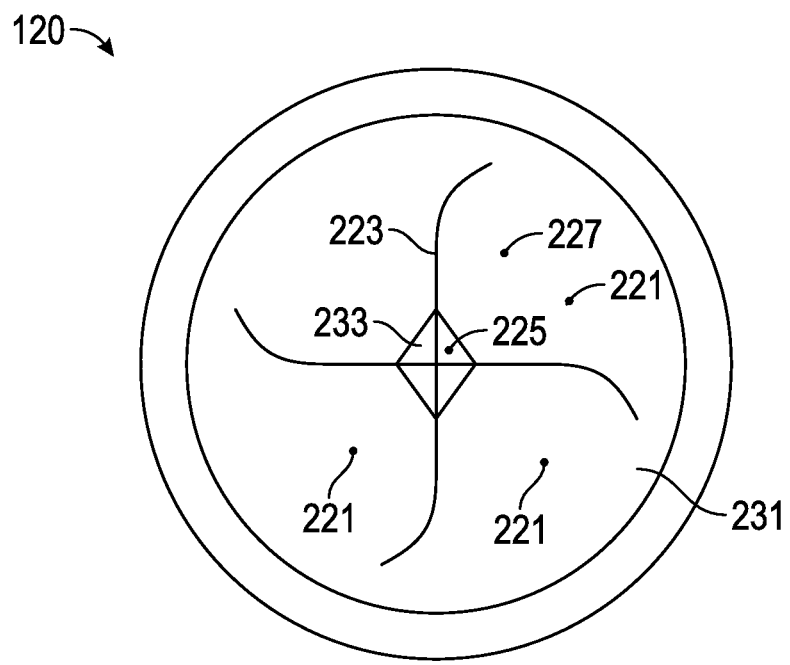
Figure 6G:
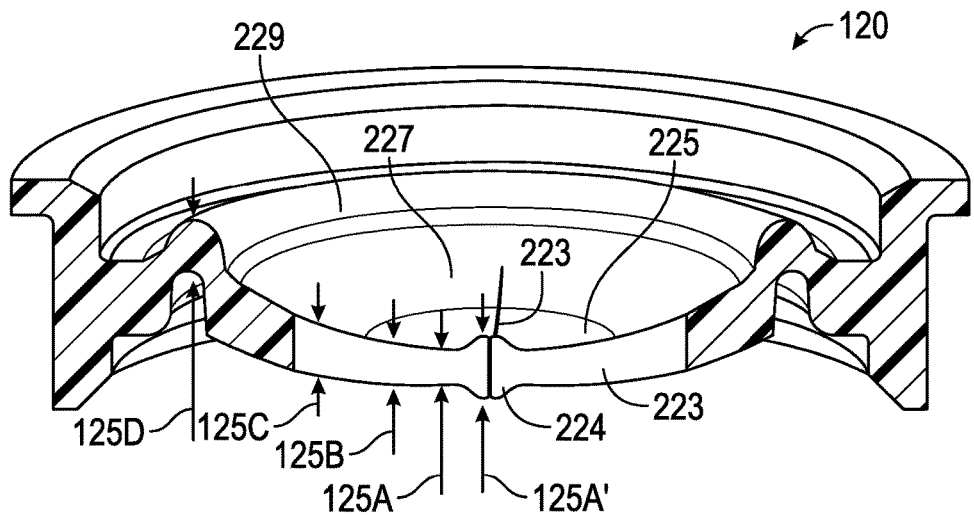
FIGS. 6G-6J illustrate cross-sectional perspective views of examples of multiple-purpose valves, in accordance with aspects of the present disclosure.

In some embodiments, for example, the example embodiment illustrated in FIG. 6G, one or more of the valve segments 221 may further include one or more raised areas 224 on one or more of the first regions 225 and/or second regions 227 (e.g., FIGS. 6A-6C). Accordingly, the one or more raised areas 224 may be formed as a bead or bump at an intersection of the one or more slits 223 (e.g., FIGS. 6A and 6G) such that the first thickness 125A is less than the raised thickness 125A of the one or more raised areas 224. The one or more raised areas 224 may be formed as a ring or annular bump structure disposed within the one or more second regions 227 of the valve segments 221 (e.g., FIG. 6B) proximal to the one or more first regions 225. In other embodiments, the one or more raised areas 224 may be disposed both within the one or more first regions 225 and the one or more second regions 227 of the valve segments 221 (e.g., FIG. 6C), whereby some of the one or more raised areas 224 may be disposed distal from the one or more first sections 225 so as to be positioned near a portion of the diaphragm section 125 having a greater frictional force or resiliency proximal to the ends of the one or more slits 223, for example, when a suction catheter (or other medical implement) is inserted through the valve 120.

In this regard, the protrusion portions of the one or more raised areas 224 (e.g., discontinuity in thickness with respect to adjacent portions) may be disposed on a top surface of the diaphragm section 125 of the valve 120 facing an access port for receiving the suction catheter (e.g., when assembled in airway adapter 100). During suction catheter insertion, valve 120 and the plurality of valve segments 221 thereof may open and conform in a direction of catheter movement. For example, when the suction catheter begins to retract from the artificial airway, frictional force by contact of the one or more raised areas 224 with the suction catheter will invert the valve segments 221 thereby pulling valve 120 towards the direction of retraction promptly and consistently, in accordance with certain aspects. Thus, one or more raised areas 224 of the one or more first regions 225 disposed at or near a tip of each valve segment 221 and/or other portions of one or more valve segments 221 can be configured to add an extra radial contact or force (e.g., providing better traction) when the suction catheter is to be retracted from the artificial airway.

Additionally as noted herein, one or more raised areas 224 may be positioned within or proximal to the one or more first regions 225 (e.g., at or proximal to an intersection of at least some of the one or more slits 223). The one or more raised areas 224 may similarly aid in keeping direct contact with the suction catheter (e.g., preventing the thinner portions 125A and 125B of the first regions 225 from bowing convexly or away from the outer surface of the suction catheter). Moreover, the additional thickness by one or more raised areas 224 positioned proximal to or at the intersection of the one or more slits 223 may also aid valve 120 to reseal or close faster and/or more securely when the suction catheter is fully retracted.

In certain implementations, the one or more raised areas 224 may be formed from the same material as the other portions of the diaphragm section 125. However, in other implementations, the one or more raised areas 224 may be formed to include other materials or compounds to increase the rigidity or frictional characteristics of the one or more raised areas 224.

In some aspects, the one or more second regions 227 may have a third thickness 125C. The third thickness 125C of the one or more second regions 227 is greater than the second thickness 125B of the one or more first regions 225, in accordance with certain aspects, and can provide sufficient rigidity for operation of valve 120 in airway adapter 100. In this regard, the thickness and rigidity of the one or more second regions 227 can aid in securing and scraping a suction catheter during retrieval from the artificial airway 165.

Moreover, as shown in the example embodiment of FIG. 6G, valve 120 may have a third region 229 encircling both the one or more first regions 225 and the one or more second regions 227. The third region 229 may comprise an arcuate cross-sectional biasing feature disposed proximal to the outer rim section. In some aspects, the arcuate cross-sectional biasing feature includes an apex thickness greater than the first thickness of the one or more first regions. For example, the third region 229 may have a fourth thickness 125D (e.g., an apex thickness) that is greater than the first thickness 125A, and in some implementations, thicker than the second thickness 125B, and/or the third thickness 125C. Accordingly, the third region 229 may provide a biasing function of valve 120 with the inner angled wall portion 117 of the airway adapter 100 (FIG. 3B) such that the valve 120 may return to an unbiased position after removal of the suction catheter as well providing additional support for the scraping function of the plurality of valve segments 221. For example, in an initial relaxed or unbiased position, the diaphragm section 125, and particularly the third region 229 (e.g. radial bump portion) of the diaphragm section 125 may not have any contact with the valve housing interior (e.g., inner angled wall portion 117 of the airway adapter 100 (FIG. 3B)). After insertion of the suction catheter, when the suction catheter starts to retract and pull back the valve 120 in a direction of the retracting motion, the third region 229 (e.g. radial bump portion) may move into and contact the inner angled wall portion 117.

Accordingly, this contact force can provide support for scraping the suction catheter as the suction catheter retracts and a "push off" resilient force when the suction catheter is fully retracted and the valve 120 begins to reseal. During retraction, the arcuate cross-sectional biasing feature of the third region 229 permits inversion of the valve segments 221, thereby pulling valve 120 towards the direction of retraction. In this regard, the arcuate cross-sectional biasing feature of the third region 229 may function to support prompt (e.g., no or minimal delay) and proper (e.g., no leaking) self-resealing of valve 120. In other aspects, the third region 229 may also provide friction control and biasing functions of valve 120 such that the valve 120 may be more receptive to movements of the suction catheter (e.g., lateral or transverse movements with respect to the axial center 101 of airway adapter 100 (FIG. 3B)) while inserted therethrough, and may return to an unbiased position after the suction catheter has been removed, for example.

Figure 6H:
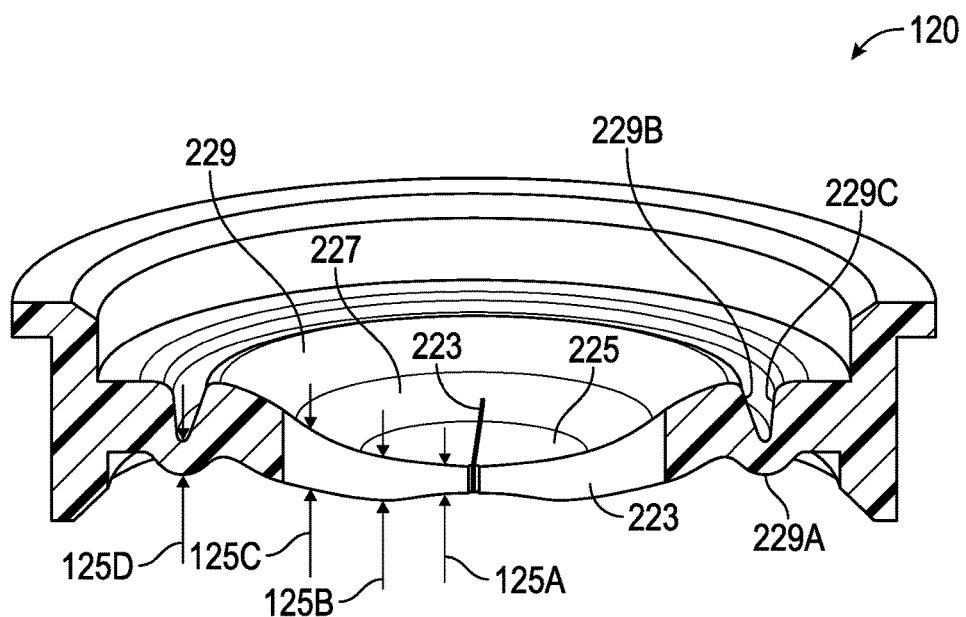

In other embodiments, for example, the example embodiment illustrated in FIG. 6H, the third region 229 of valve 120 may comprise an arcuate cross-sectional biasing feature disposed proximal to the outer rim section that includes a bend portion 229A and two opposing wall portions 229B, 229C. Thus, the third region 229 may comprise a circumferential accordion bellow with a generally "V"-shaped cross-section in accordance with certain embodiments thereby providing improved shape and flexibility. In some aspects, the arcuate cross-sectional biasing feature may include an apex thickness greater than the first thickness of the one or more first regions. For example, the third region 229 may have a fourth thickness 125D (e.g., an apex thickness at bend portion 229A) that is greater than the first thickness 125A. In some implementations, the fourth thickness 125D may be thicker than the first region, but thinner than the third thickness 125C. Thus, the third region 229 can provide a consistent radial and friction force with respect to a suction catheter (or other medical implement) inserted through the valve 120.

The third region 229 in the example embodiment of FIG. 6H, for example, may provide a biasing function of valve 120 whereby the two opposing wall portions 229B, 229C may approach one another at sections distal of the bend portion 229A (e.g., closing or narrowing of the "V"-shaped cross-section) as a suction catheter (or other medical implement) is being retracted from the artificial airway and return to an unbiased position (e.g., revert back to the "V"-shaped cross-section aiding the valve segments 221 to fully close) when a tip of the suction catheter has been removed through the valve 120 and into the access zone or cleaning chamber of the airway adapter 100. Accordingly, the third region 229 may retain its shape and flexibility during suction catheter insertion/retraction operations and thereby aid in stabilizing valve 120 and returning the valve 120 to an unbiased position (e.g., close valve segments 221 and reseal the valve 120). Additionally, the third region 229 may promote inversion of the valve segments 221, for example, when the suction catheter (having either a wet or dry outer surface) starts to retract and pull back the valve 120 in a direction of the retracting motion during operation of the airway adapter 100.

Figure 6I:
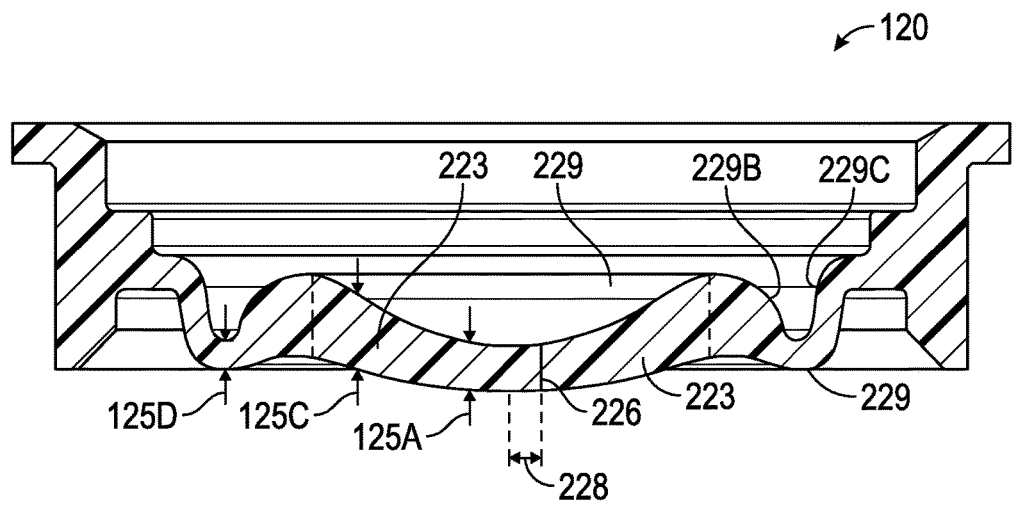

In other embodiments, for example, the embodiment illustrated in FIG. 6I, the arcuate cross-sectional biasing feature may include an apex thickness less than the first thickness of the one or more first regions. For example, the third region 229 may have a fourth thickness 125D (e.g., an apex thickness at bend portion 229A) that is less than the first thickness 125A. In some implementations, the fourth thickness 125D may also be thinner than a third thickness 125C, located radially between the first thickness 125A and the fourth thickness 125D. Thus, the third region 229 can provide a consistent radial and friction force with respect to a suction catheter (or other medical implement) inserted through the valve 120. In some aspects, the intersection 226 of the slits is offset from the center of the valve 120 by a radial distance 228.

Figure 6J:
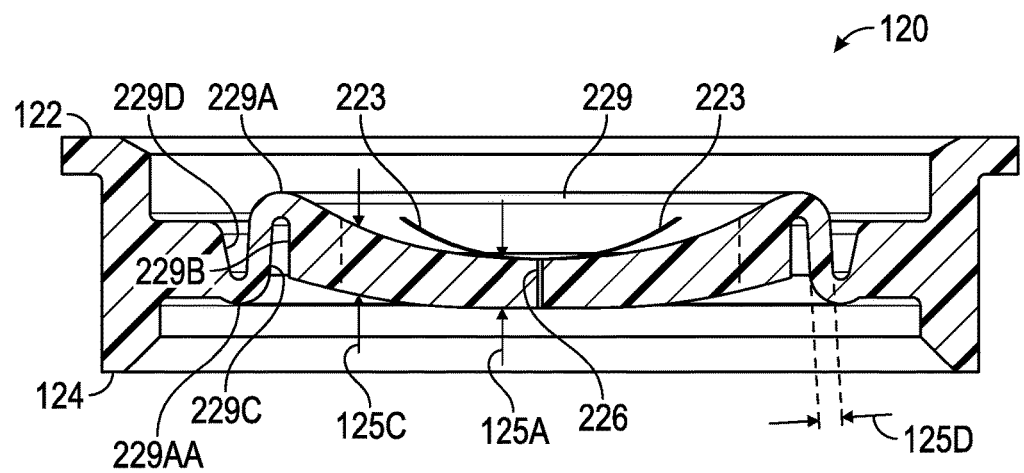
Figure 6K:
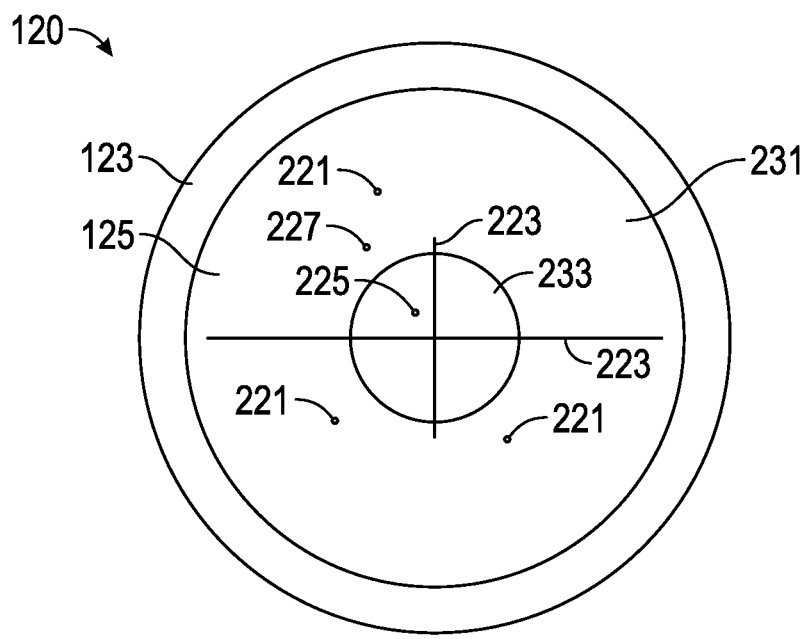
FIGS. 6K-6M illustrate plan views of examples of multiple-purpose valves, in accordance with aspects of the present disclosure.
Figure 6L:
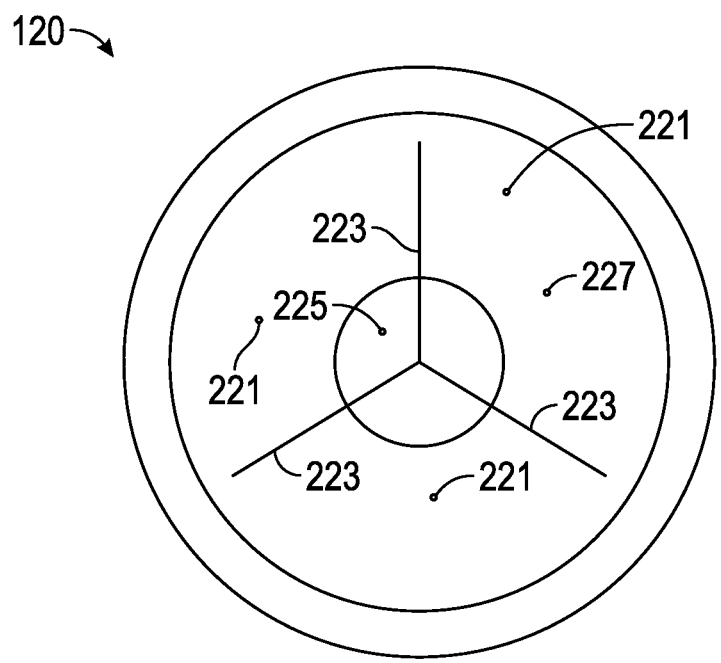

In other embodiments, for example, the embodiment illustrated in FIG. 6J, the third region 229 may comprise an arcuate cross-sectional biasing feature disposed proximal to the outer rim section that includes bend portions 229A and 229AA, and three opposing wall portions 229B, 229C, and 229D. Thus, the third region 229 may comprise a circumferential accordion bellow with a generally "S"-shaped cross-section in accordance with certain embodiments thereby providing improved shape and flexibility. In some aspects, bend portion 229AA is coupled to wall portion 229D, and bend portion 229A is coupled to wall portion 229B, such that wall portion 229C extends between bend portions 229A and 229AA. In some aspects, bend portion 229AA is distal from the leading edge 122 of the valve 120 while bend portion 229A is proximal to the leading edge 122 of the valve 120.

The third region 229 may provide a biasing function of valve 120 whereby the three opposing wall portions 229B, 229C, and 229D may approach one another at sections distal of the bend portions 229A and 229AA (e.g., closing or narrowing of the "S"-shaped cross-section) as a suction catheter (or other medical implement) is being retracted from the artificial airway and return to an unbiased position (e.g., revert back to the "S"-shaped cross-section aiding the valve segments 221 to fully close) when a tip of the suction catheter has been removed through the valve 120 and into the access zone or cleaning chamber of the airway adapter 100. In other aspects, the third region 229, particularly the bend portion 229A may also provide radial and friction force control of valve 120 such that the valve 120 may be more flexible and receptive to the movement of a suction catheter or other medical instruments (e.g., valve being pulled towards the direction of catheter movement) during insertion and retraction and may help return to an unbiased position after the suction catheter has been removed from extending through the valve 120.

In some aspects, the arcuate cross-sectional biasing feature may include an apex thickness less than the first thickness of the one or more first regions. For example, the third region 229 may have a fourth thickness 125D (e.g., an apex thickness at bend portion 229A) that is less than the first thickness 125A. In some implementations, the fourth thickness 125D may also be thinner than a third thickness 125C, located radially between the first thickness 125A and the fourth thickness 125D. In some implementations, the bend portion 229A and wall portion 229C have a consistent thickness. In some implementations, the fourth thickness 125D may be in the range of 0.0135 to 0.0165 inches. In an implementation, the fourth thickness 125D is 0.015 inches. Thus, the third region 229 can provide a consistent radial and friction force with respect to a suction catheter (or other medical implement) inserted through the valve 120. In some aspects, the intersection of the slits 223 is offset from the center of the valve 120 by a distance 228.

Figure 6M:
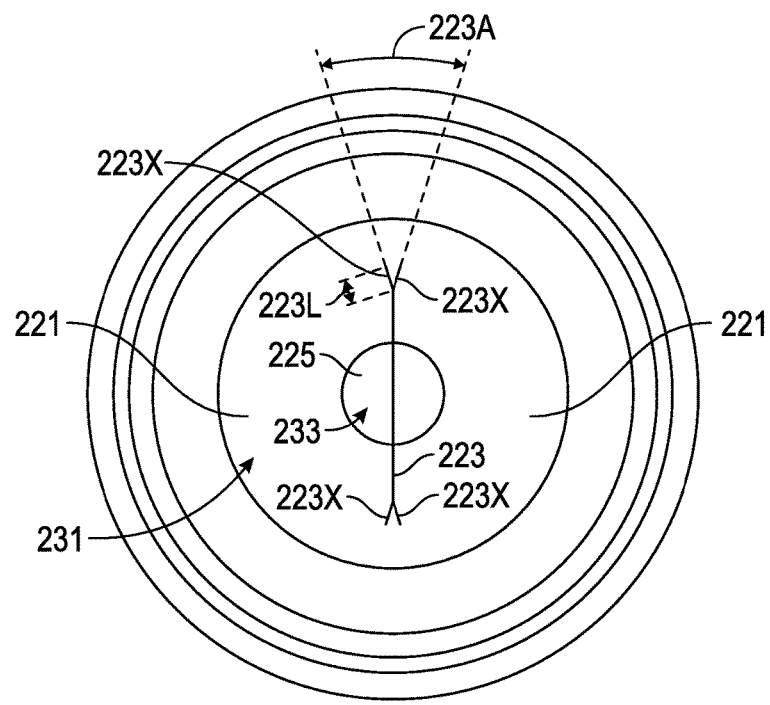
Figure 6N:
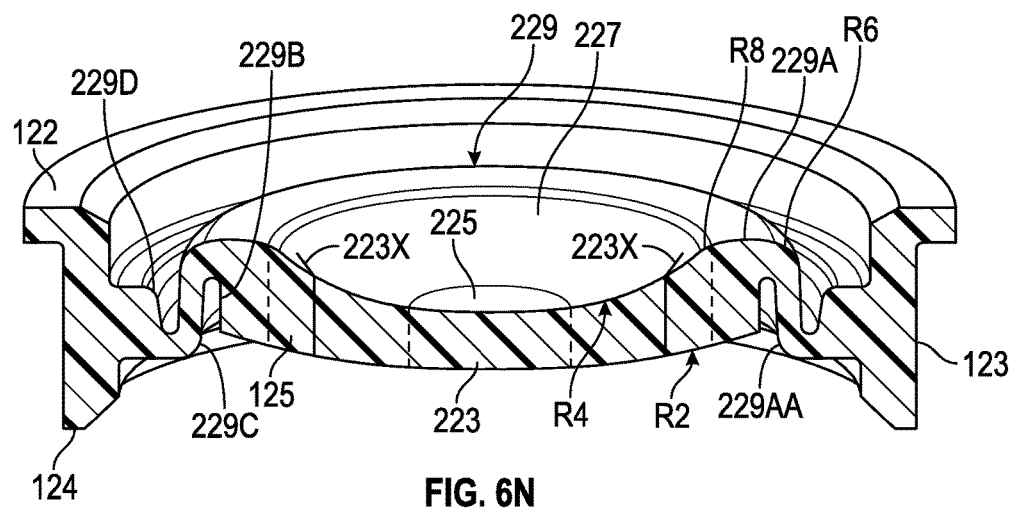
FIG. 6N illustrates a cross-sectional perspective view of the multiple-purpose valve of FIG. 6M.

In other embodiments, for example, the embodiment illustrated in FIG. 6N, the third region 229 may comprise an arcuate cross-sectional biasing feature disposed proximal to the outer rim section that includes bend portions 229A and 229AA, and three opposing wall portions 229B, 229C, and 229D. In an embodiment, a flat surface of the inner resiliently flexible diaphragm section extends orthogonally from an inner surface of the outer rim 123 to bend portion 229AA. In some embodiments, a surface of bend portion 229A proximal to the leading edge 122 may form a plateau and have a radius R6 between bend portion 229A and wall portion 229C, and a radius R8 between bend portion 229A and the valve segments 221. In some embodiments, the radius R6 may be in the range of 0.018 to 0.022 inches, and the radius R8 may be in the range of 0.063 to 0.077 inches. In an embodiment, the radius R6 is 0.020 inches and the radius R8 is 0.070 inches.

Other aspects of valve 120 are illustrated in the examples of FIGS. 6A-6F and 6K-6N. For example, the one or more slits 223 may have different lengths (e.g., valves designed for a 6 Fr. catheter versus a 16 Fr. catheter), the number and shape of slits 223 and corresponding valve segments 221 may vary, and/or the area of the secondary seal 233 may be different in various implementations. In some embodiments, the slits 223 and/or 223X may form a cross-shaped pattern through the diaphragm section 125 (e.g., FIGS. 6A-6C and 6K). In some embodiments, the slits 223 and/or 223X may form a symmetric pattern through the diaphragm section 125. In other embodiments, the slits 223 and/or 223X may form an asymmetric pattern through the diaphragm section 125 (e.g., FIGS. 6E, 6F, and 6L). For example, the slits 223 illustrated in FIG. 6L form a star pattern. Additionally, in some implementations, the one or more second regions 227 may comprise a greater surface area of the diaphragm section 125 than the one or more first regions 225.

Referring to FIGS. 6M-6N, in some embodiments, the valve 120 comprises one or more minor slit 223X that may intersect or extend from and end of the slit 223. In some embodiments, the length 223L of a minor slit 223X may be in the range of 0.0123 to 0.0187 inches. In an embodiment, the length 223L of a minor slit 223X is 0.017 inches. In some embodiments, an angle of a minor slit 223X relative to the slit 223 may be in the range of 10 to 30 degrees. In an embodiment, two minor slits 223X extend from an end of the slit 223 to form a "Y"-shaped pattern with the slit 223. In some embodiments, an angle 223A of the minor slits 223X relative to each other is in the range of 15 to 60 degrees. In an embodiment, the angle 223A between two minor slits 223X is 30 degrees.

A resealable opening of the secondary seal 233 may be defined by the intersection of the one or more slits 223. In certain embodiments, the resealable opening of the secondary seal 233 is aligned with a resealable opening of the primary seal 231. However, the resealable opening of the primary seal 231 extends farther than that of the secondary seal 233. The resealable opening of the secondary seal 233 and the resealable opening of the primary seal 231 may be aligned with an approximate center of the diaphragm section 125. In this regard, the approximate center of the diaphragm section 125 of valve 120 when retained in airway adapter 100 may be aligned with the axial center 101 of the elongate cavity 115 of the connector body 111 (FIG. 3B). In such examples, the first region 225 of the valve segment 221 can be configured such that an end proximal to the axial center 105 has a thickness of the first thickness and a portion distal from the axial centerline that has a thickness of the second thickness.

In other embodiments, a resealable opening of the secondary seal 233 can be located at a different position on the diaphragm section 125 than proximal to the center of a resealable opening of the primary seal 231 (e.g., FIG. 6E). For example, the resealable opening of the secondary seal 233 may be located within the diaphragm section 125 proximal to the rim 123, whereas resealable opening of the primary seal 231 may be located at the approximate center of the diaphragm section 125. However, in other embodiments, the secondary seal 233 may be formed from a different set of one or more slits 223 than the primary seal 231 within the diaphragm section 125 (e.g., a first set of one or more slits associated with the primary seal and a second set of one or more slits associated with the secondary seal). For example, the slits and first portions of the secondary seal can be located in one of the quadrants defined by the larger slits that make out the primary seal. Moreover, in other embodiments, the one or more first regions 225 may be disposed on the diaphragm section 125 at an intersection of at least some of the one or more slits 223 and have a thinnest thickness at an intersection of the one or more slits 223 (e.g., without including raised areas 224, FIGS. 6D, 6E, and 6F).

Figure 7:
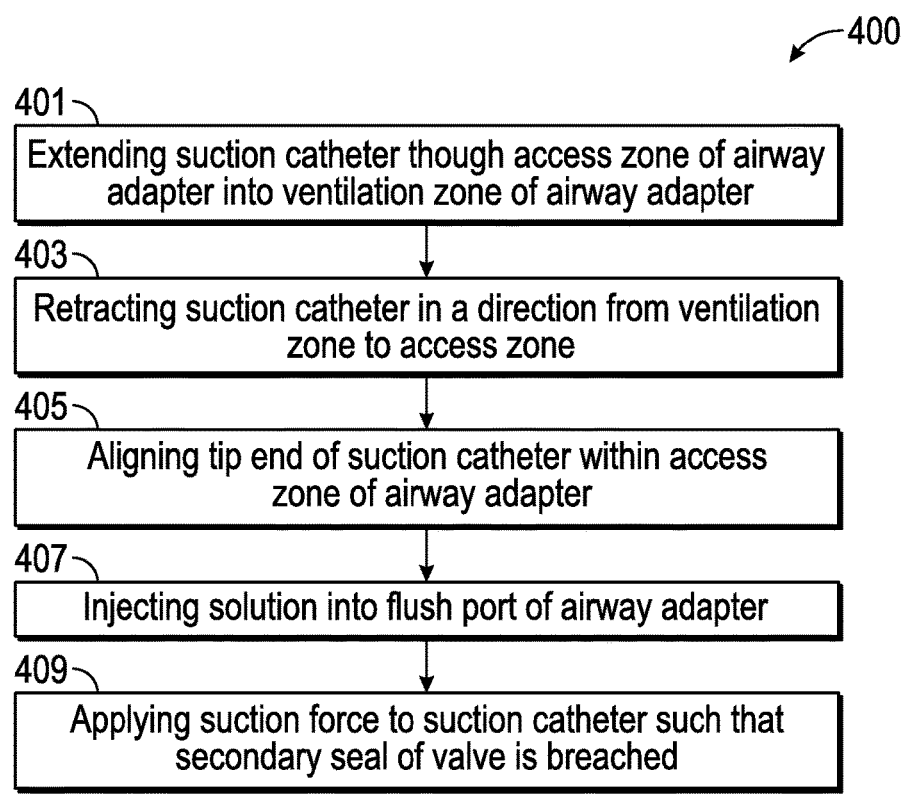
FIG. 7 is a flow chart of an example method of using and cleaning a suction catheter, in accordance with aspects of the present disclosure.

FIG. 7 illustrates a flow diagram of an example method related to use and cleaning aspects of an airway adapter. It is to be understood that the operations in method 400 may be used in conjunction with other methods and aspects of the present disclosure. Although aspects of method 400 are described with relation to the examples provided in FIGS. 8A-8C and 9A-9B, as well as reference to certain examples provided in FIGS. 1 to 6F, process 400 is not limited to such.

Figure 8A:
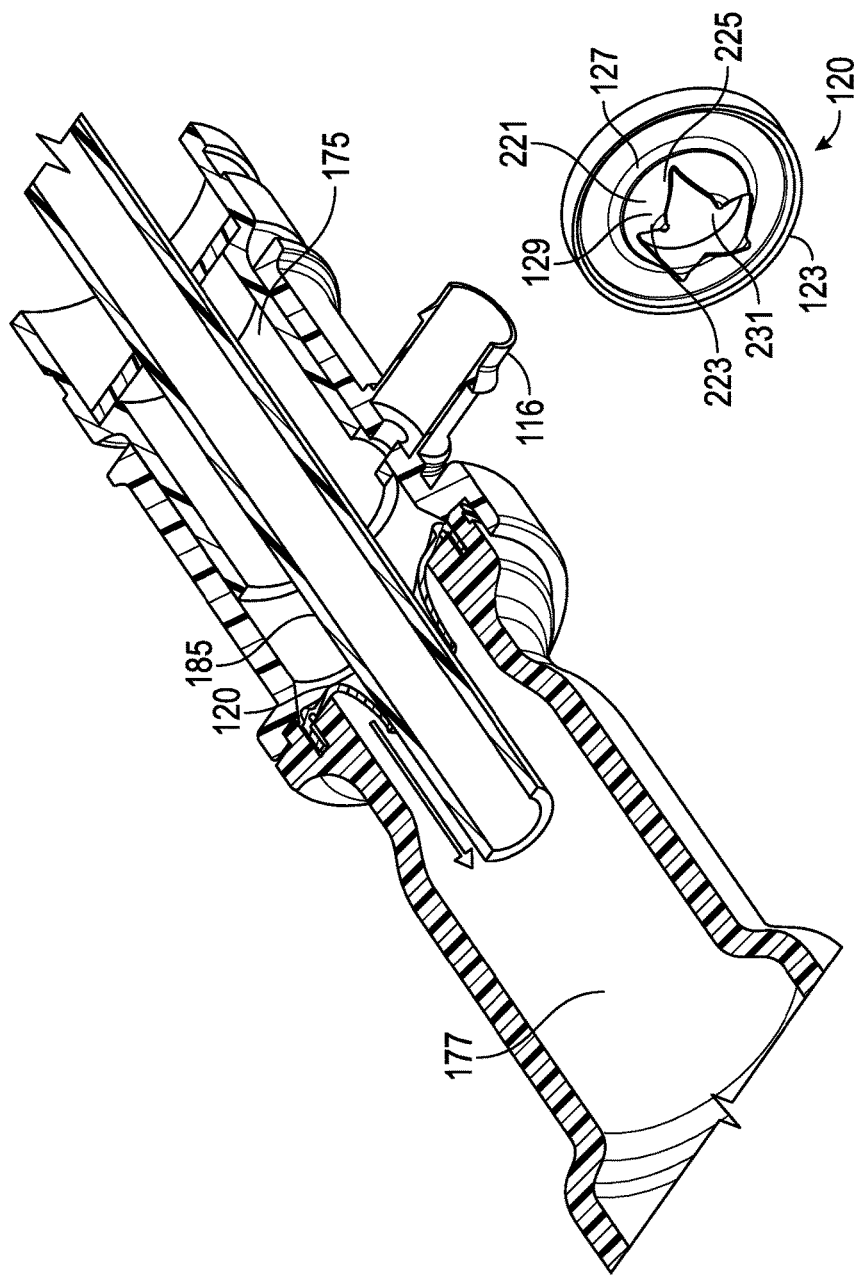
FIG. 8A-8B illustrates cross-sectional perspective views of examples of multiple-port airway adapter in use with a suction catheter, in accordance with aspects of the present disclosure.
Figure 8B:
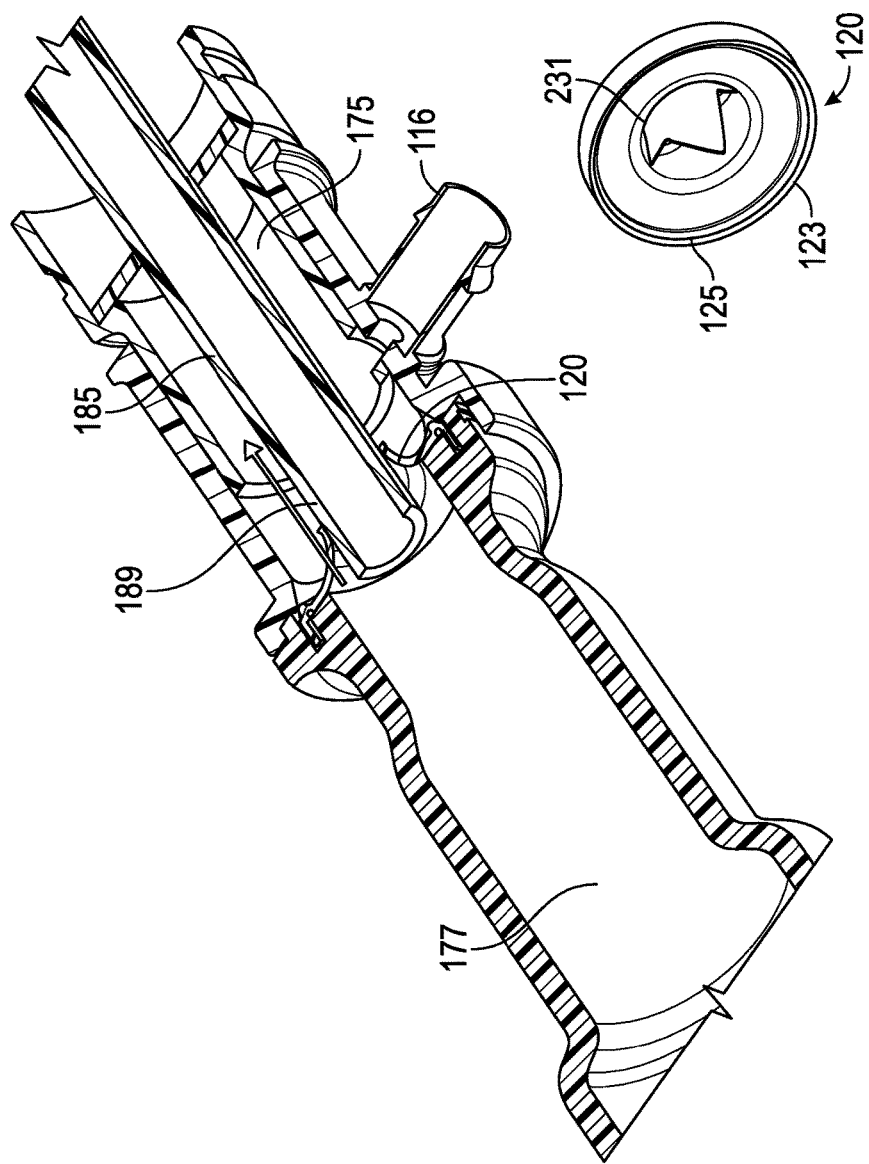
Figure 8C:
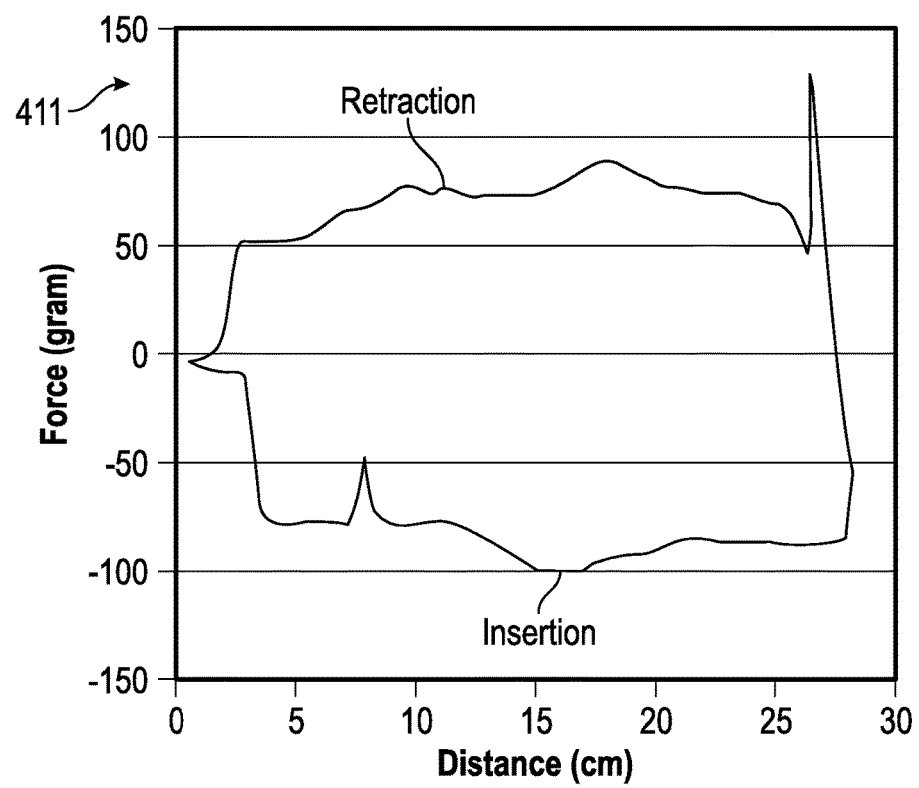
FIG. 8C illustrates a chart of example insertion and retraction forces associated with the suction catheter of FIGS. 8A and 8B, in accordance with aspects of the present disclosure.

In block 401, a suction catheter may be extended through an access zone of an airway adapter into a ventilation zone of the airway adapter such that a primary seal formed by a plurality of valve segments is breached. For example, with reference to FIG. 8A, suction catheter 185 may be extended through access zone 175 into ventilation zone 177 such that a primary seal 231 of valve 120 formed by a plurality of valve segments 221 is breached. In some aspects, at least some of the valve segments 221 extend toward the ventilation zone 177. Friction forces on the suction catheter 185 with respect to the distance extended into a patient airway in accordance with certain embodiments are illustrated in the chart of FIG. 8C.

In block, 403 the suction catheter may be retracted in a direction from the ventilation zone to the access zone. For example, with reference to FIG. 8B, suction catheter 185 (or tubing coupled thereto) may be retracted or retrieved from the ventilation zone 177 to the access zone 175. In some aspects, at least some of the valve segments 221 of valve 120 extend toward the ventilation zone 177. As described herein, one or more raised areas 224 may aid in keeping direct contact with the suction catheter 185 and causing the valve segments 221 to invert and extend toward the access zone 175.

In this regard, a function of certain valve 120 embodiments can be to scrape a surface of the suction catheter 185 as it is retracted or withdrawn from the patient's airway so as to clean, at least partially, the catheter surface, for example. However, unless the mucus, secretions, and other fluids from the lungs are removed by the suction catheter, these substances may accumulate and potentially occlude the airway. Therefore, configuring valve 120 such that the valve segments 221 (particularly the one or more second regions 227) are sufficiently rigid and flexible such that the valve segments 221 can effectively support and/or scrape the suction catheter 185 as well as invert toward the access zone 175 during retraction so the mucus, secretions, and other fluids accumulate where these substances can be removed by the suction catheter provides an advantage of an airway adapter comprising valve 120.

In certain aspects, the plurality of valve segments 221 of the valve 120 may be configured to form a primary seal 231 and a secondary seal 233. Valve 120 is configured such that it will revert back to an unbiased configuration when the suction catheter 185 is fully retracted into the access zone 175 and no longer engaged with the valve 120. As described herein, third region 229 of valve 120 may provide a biasing function of valve 120 with the inner angled wall portion 117 of the airway adapter 100 such that the valve 120 may return to an unbiased position after removal of the suction catheter 185. In the unbiased configuration, the primary seal 231 and secondary seal 233 will again form a fluid barrier between the ventilation zone 177 and the access zone 175.

Additionally, friction forces on the suction catheter 185 with respect to distance retracted from a patient airway in accordance with certain embodiments are illustrated in the chart of FIG. 8C.

Figure 8D:
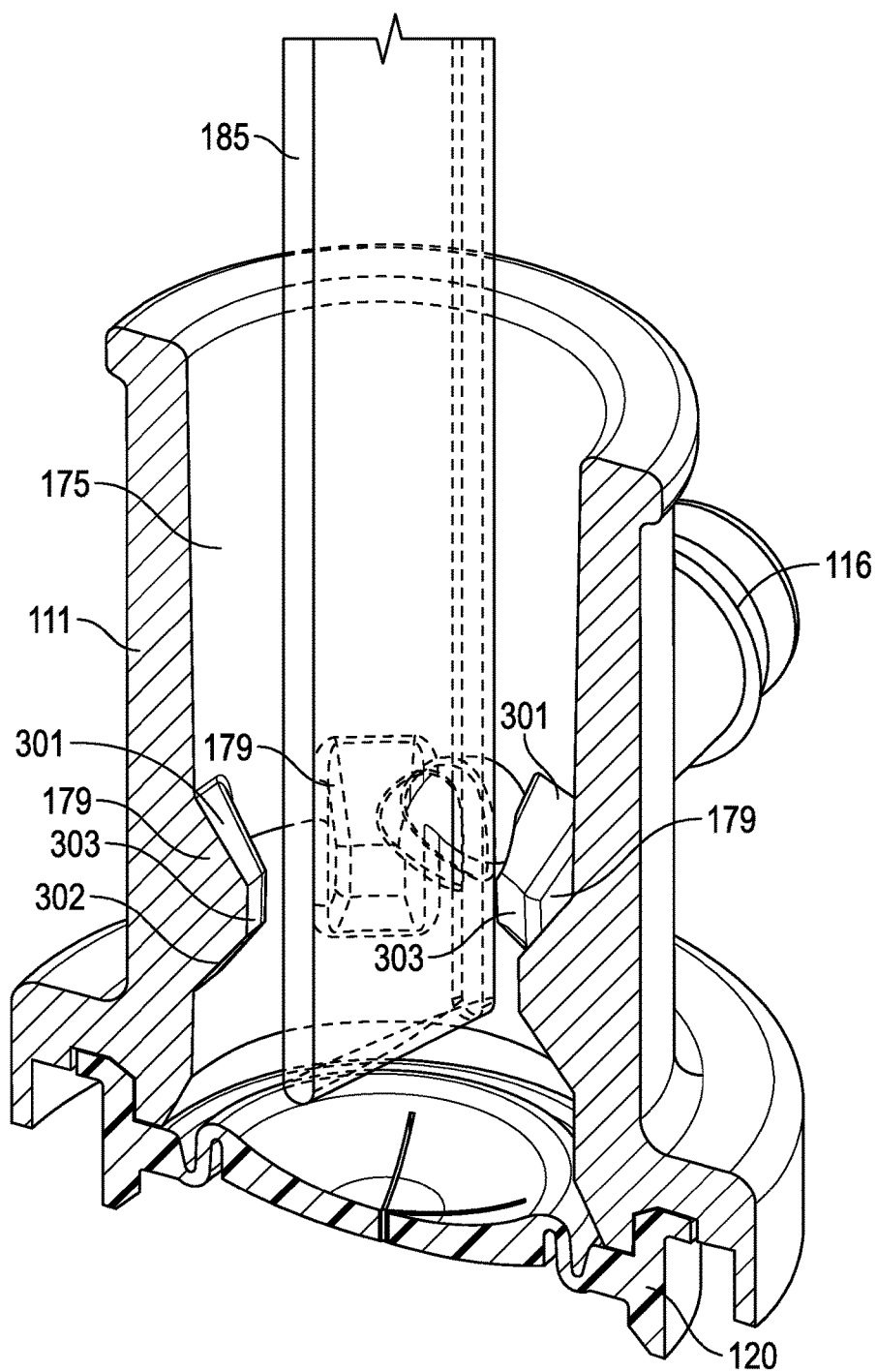
FIG. 8D illustrates cross-sectional perspective view of an example of multiple-port airway adapter in use with a suction catheter, in accordance with aspects of the present disclosure.

In some aspects, for example, the embodiment illustrated in FIG. 8D, one or more protrusions 179 may be disposed on an inner wall of the connector body 111 in the access zone 175. The protrusions 179 may extend from the inner wall toward the axial center of the elongate cavity 115. Each protrusion 179 comprises an inclination surface 301, a return surface 302 extending transversely to the inclination surface 301, and an apex area 303 that transitions between the ramp surface and the engagement surface. In an embodiment, the apex area 303 is parallel to the axial center of the elongate cavity 115.

The protrusions 179 direct a suction catheter 185 toward the axial center of the elongate cavity 115. In some embodiments, the protrusions 179 extend an equal distance toward the axial center of the elongate cavity 115 such that the suction catheter 185 aligned with the center of the valve 120. In some embodiments, the protrusions 179 extend varying distances into the elongate cavity 115 such that the suction catheter 185 is aligned a radial distance from the center of the valve 120. For example, where a valve such as that illustrated in FIG. 6I is used, the protrusions 179 extend varying distances into the elongate cavity 115 such that the suction catheter 185 is aligned with the intersection 226 of the slits, a distance 228 from the center of the valve 120.

When a suction catheter 185 is extended through access zone 175 toward ventilation zone 177, tip end 189 of the suction catheter 185 may engage one or more inclination surface 301 such that suction catheter 185 is generally directed toward a point between the apex areas 303 of the protrusions 179. As the suction catheter 185 is further extended through access zone 175, the suction catheter 185 will remain between the apex areas 303. Maintaining alignment of the suction catheter 185 within the elongate cavity 115 provides control over the point of engagement between the tip end 189 of the suction catheter 185 and the valve 120. Further, the protrusions 179 maintain the suction catheter 185 in coaxial alignment with the elongate cavity 115 during insertion and retraction through the access zone 175.

In block 405, a tip end of a suction catheter may be aligned within an access zone 175 of an airway adapter. For example, with reference to FIG. 9A, suction catheter 185 may be aligned or positioned such that tip end 189 of the suction catheter 185 is positioned between valve 120 and an airway adapter coupler 170.

As previously described, each of the primary and secondary seals 231, 233 provides a breachable seal between access zone 175 and ventilation zone 177 of the airway adapter. In some aspects, the airway adapter coupler 107 includes a wiper seal 172 having a wall portion and an access aperture. The wiper seal 172 may be configured to provide a slidably frictional fitting with the suction catheter 185.

In block 407, a solution may be injected into a flush port of the airway adapter that is in fluid communication with the access zone 175. For example, with reference to FIG. 9A, the tip end 189 of the suction catheter 185 may be positioned in the access zone 175. Saline or a cleaning solution may then be injected via flush port 116 into the access zone 175 fluidly coupled to the flush port 116, for example, thereby providing a cleaning chamber for the suction catheter 185. In some aspects, saline or a cleaning solution may be injected into the flush port 116 via a wash port valve assembly 600 (e.g, FIGS. 2A-2K and 9C-9E).

In block 409, a suction force to the suction catheter may be applied. For example, with reference to FIG. 9A, suction source 195 may be applied to the suction catheter 185 such that the secondary seal 233 of the valve 120 is breached, causing airflow from the ventilation zone 177 into the access zone 175.

Accordingly, an airway adapter comprising valve 120 may include a volume (e.g., access zone 175 or elongate cavity 115) for cleaning a catheter tip or other medical implement (e.g., Mini-BAL device or a bronchoscope) following a suctioning or other airway procedure. Valve 120 is configured to allow a small amount of air (relative to the amount and flow generated by a ventilation source of a particular patient's artificial airway circuit) through the seal so as to entrain air into the fluid flow of saline or cleaning solution so as to improve the cleaning procedure effectiveness.

Figure 9A:
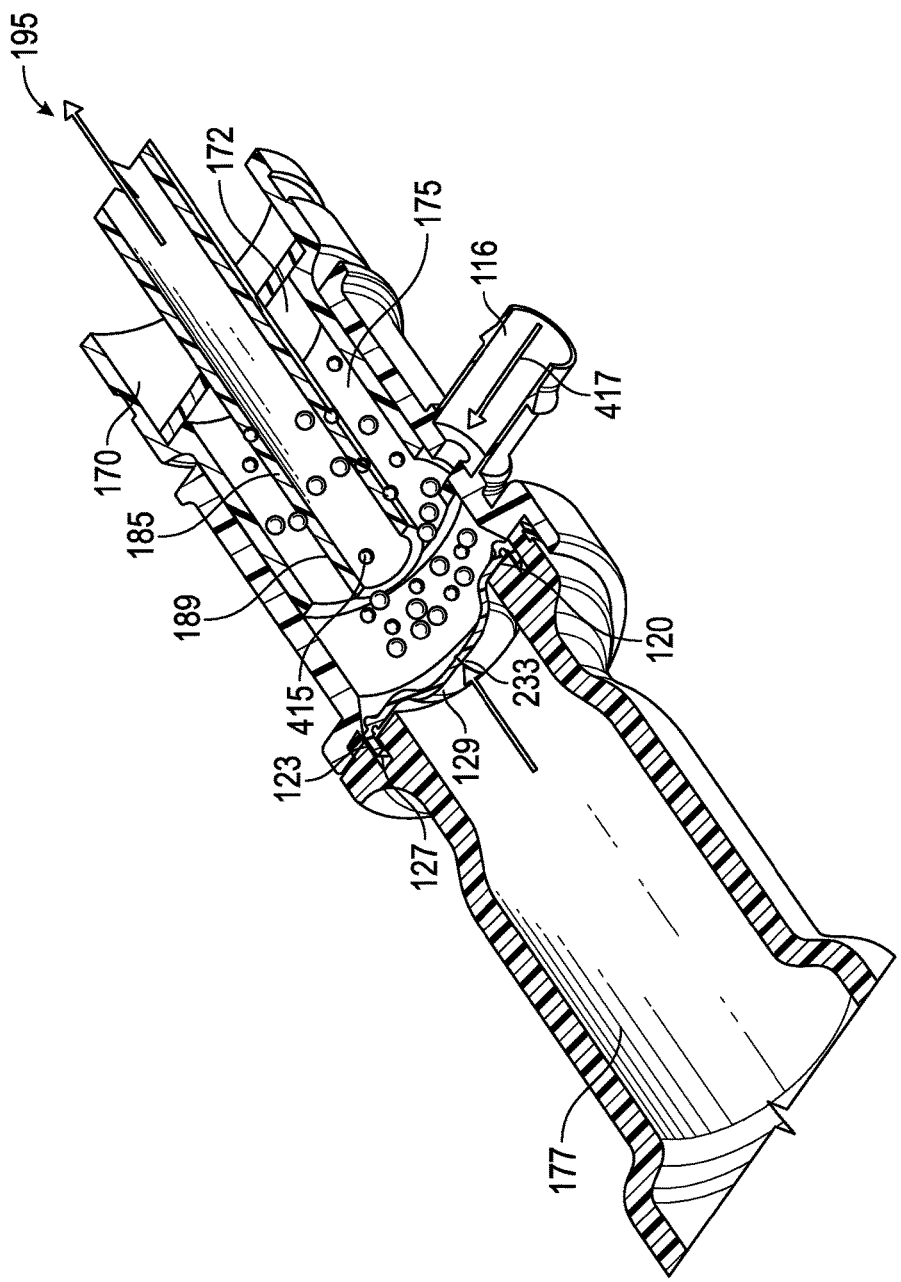
FIG. 9A illustrates a cross-sectional perspective view of an example of a multiple-port airway adapters in use with a suction catheter, in accordance with aspects of the present disclosure.
Figure 9B:
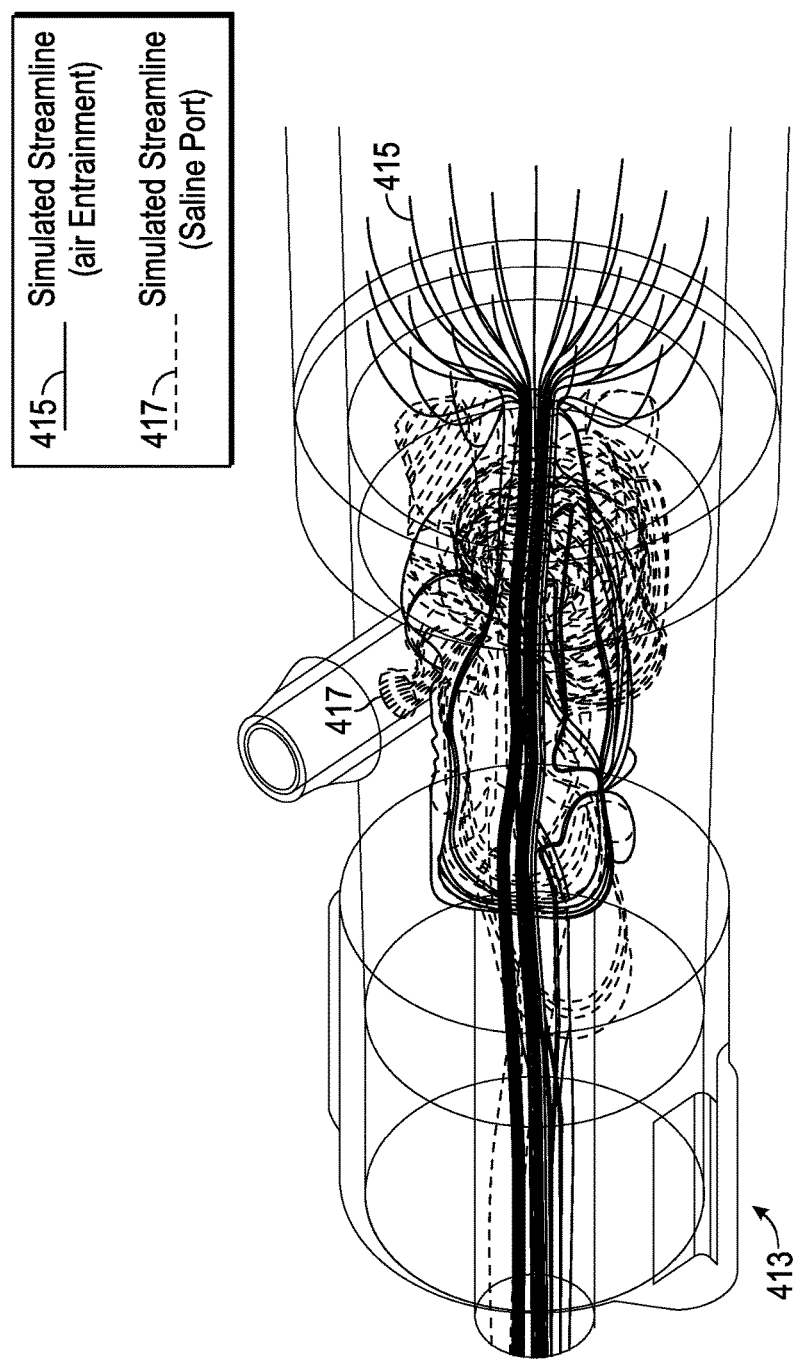
FIG. 9B illustrates a perspective view of an example air-entrainment simulation of the multiple-port airway adapter in use with the suction catheter of FIG. 9A, in accordance with aspects of the present disclosure.

FIG. 9B illustrates an example of an air-entrainment simulation of the multiple-port airway adapter used with the suction catheter provided in the example of FIG. 9A. Air-entrainment simulation 413 includes air entrainment traces 415 and solution traces 417. As can be seen in air-entrainment simulation 413, agitation of the solution with the air significantly enhances the effectiveness of the cleaning procedure, for example, in the small volume cavity or chamber in which the suction catheter or medical implement is cleaned.

As noted above, in some embodiments, a medical implement other than a suction catheter can be used in method 400. In this regard, the connector body may include an additional suction port in fluid communication with the elongate cavity such that both solution injection and suction can be performed without use of the suction catheter. Alternatively, the airway adapter coupler may include a suction port and a medical implement feed port enabling suctioning of the saline or cleaning solution during the cleaning process.

Various aspects of method 400 and an airway adapter comprising valve 120 according to the present disclosure may include the following. In some aspects, valve 120 is resiliently flexible so as to have a biasing (or springing) characteristic, which returns the valve 120 to a normally fluidly closed configuration. Such resealing aspects may be compromised in a device without the benefit of the present disclosure if mucus or other fluids are not properly scraped from the surface a suction catheter, thereby allowing an excessive volume of material to enter the cleaning chamber and compromising the cleaning procedure. Alternatively, a device without the benefit of the present disclosure may have a valve that scrape large volumes of mucus and other fluids from the catheter, but block or entrap these fluids whereby the mucus and fluids are displaced to a position from which the displaced mucus and fluids cannot be easily suctioned away as a suction catheter is withdrawn. The mucus and outer fluids from a device without the benefit of the present disclosure may then accumulate to the point of occluding or contaminating an airway of a patient causing harm to the patient. Method 400 and an airway adapter comprising valve 120 minimize the aforementioned patient risks, and represent an improvement in the art.

Various aspects of method 400 and an airway adapter comprising valve 120 according to the present disclosure may further include the following. Valve 120 may be formed from a single elastomeric web of material with specific morphological and elastic properties (e.g., durometer, elongation, tear strength, etc.), in accordance with examples and embodiments disclosed herein. Valve 120 may be seated and sealed to the interior structure of airway adapter 100 and thereby retained against accidental dislocation. At pressures below a first cracking pressure, valve 120 may be closed to fluid flow; at pressures ranging from the first cracking pressure to a second cracking pressure, a small flow of air from the patient's airway (relative to the total flow of ventilator air) may be entrained into a cleaning space or access zone in the airway adaptor; and at pressures above the second cracking pressure, valve 120 will open causing air to flow through the valve. Specific attributes of valve 120 may vary depending upon an intended patient population for which a particular valve is designed. For example, a particular valve designed for a 6 Fr. catheter, used for neonatal patients may have first and second cracking pressures lower than a particular valve designed for 16 Fr. catheters used on adults. Valve 120 may be designed such that the one or more slits in the diaphragm section of the valve 120 can stretch to allow passage of the closed suction catheter or other airway instruments (e.g. a Mini-BAL device or a bronchoscope) without tearing the valve 120.

Various aspects of method 400 and an airway adapter comprising valve 120 according to the present disclosure may further include the following. In accordance with method 400, upon insertion of a suction catheter, valve 120 may substantially conform to an outer diameter of the suction catheter and extend and/or elongate in a direction of catheter motion, forming a conical volume on a ventilation zone or ventilator machine side of the valve 120. Upon retraction of the suction catheter, a shape of valve 120 may invert, forming a conical volume on an access zone or cleaning chamber side of the valve 120. As the suction catheter continues to withdraw through valve 120, any mucosal or other fluids adhering to the surface of the suction catheter may be scraped off of the suction catheter. The mucosal or other fluids may then accumulate in the vicinity of the conical volume formed by the diaphragm section of the valve 120 and the access zone or cleaning chamber. As the tip of the suction catheter approaches and passes through the vicinity of accumulated mucosal or other fluids, the suction pressures at the eyes and terminus of the suction catheter will evacuate much of the accumulated mucosal or other fluids, thus cleaning the area of excessive and potentially occluding fluids.

Figure 9C:
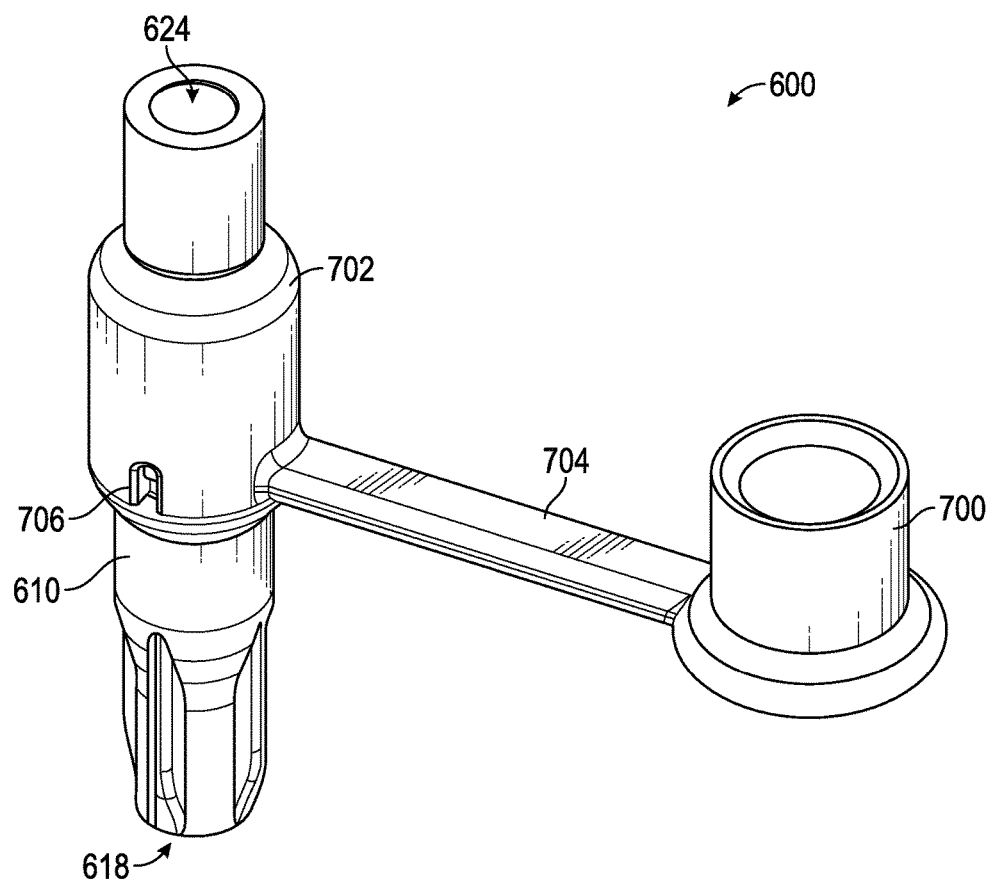
FIG. 9C illustrates a perspective view of an example wash port valve assembly in accordance with aspects of the present disclosure.
Figure 9D:
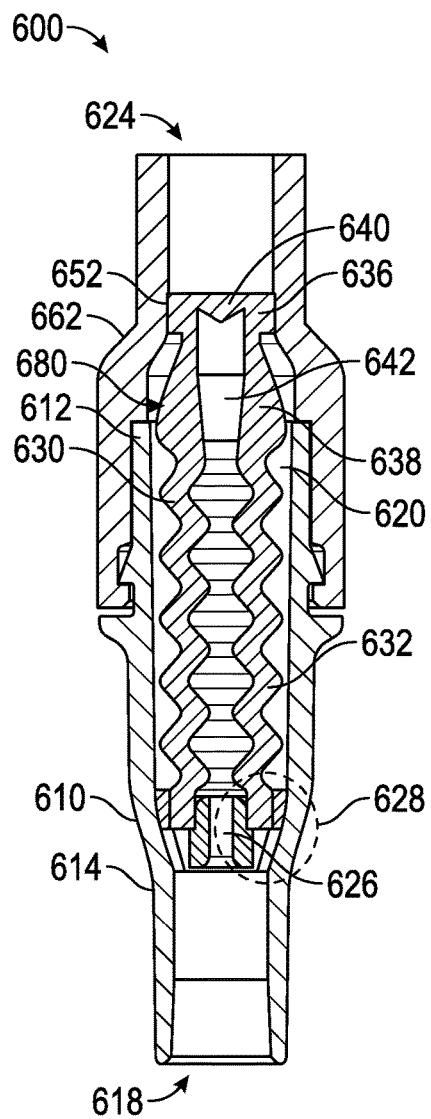
FIGS. 9D and 9E illustrate a cross-sectional view of the wash port valve assembly of FIG. 9C.
Figure 9E:
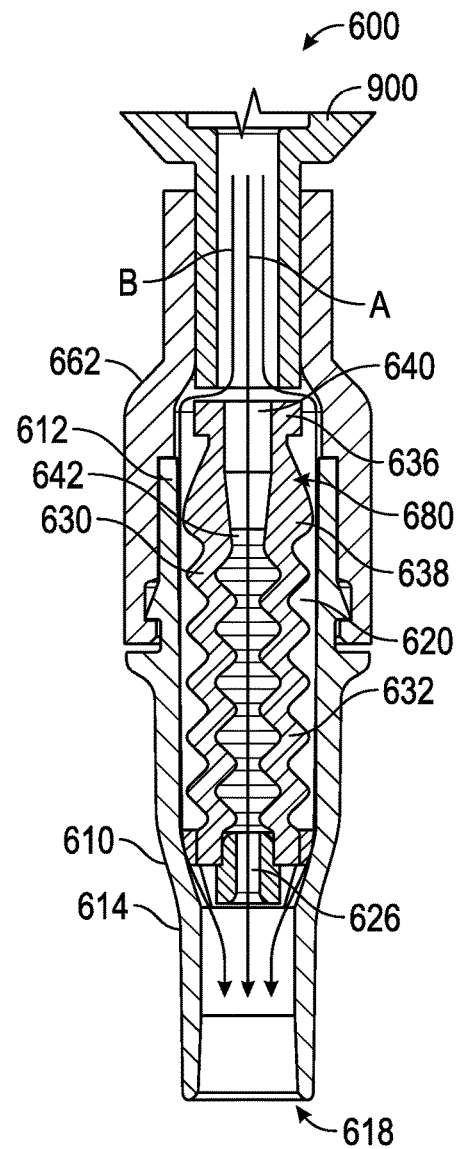

FIGS. 9C-9E illustrate a wash port valve assembly 600. The wash port valve assembly 600 comprises a body 610 and a port 662. An inlet 624 is configured to receive saline or a cleaning solution for injection into the flush port 116, while an outlet 618 is configured to fluidly couple with the tubular connector 602 of the wash port coupling assembly 216. A cap 700 is coupled to the wash port valve assembly 600 through a collar 702 and hinge 704.

Referring to FIGS. 9D-9E, the body 610 comprises a first end 612, a second end 614, an inlet 624, and an outlet 618. The body 610 houses a check valve member 680 comprising a compressible member 630. The port 662 at least partially defines the inlet 624. The body 610 defines a chamber 620, a vent 628, and an outlet channel 626. The vent 628 forms a fluid flow path from a lower portion of the chamber 620 to the outlet 618. Although FIGS. 9D and 9E show two vents 628, in other implementations there may be more or less vents 628, which may be formed in alternate configurations, such as ridges along the inner sidewall of the body 610.

The compressible member 630 comprises a head portion 636, which defines a septum 640, a shoulder portion 638, and a compressible portion 632. A hollow inner channel 642 extends from the septum 640 through the compressible portion 632 and outlet channel 626 to form a primary fluid flow path. The head portion 636 fills the inlet 624 and form a fluid seal at a sealing surface 652 when the compressible member 630 is not compressed, as seen in FIG. 9D. The compressible member 630 is configured to compress when an axial force is applied to the head portion 636 such that the head portion 636 is pushed down and offset from the sealing surface 652, as seen in FIG. 9E. The septum 640 is configured to open when the head portion 636 is pushed down, permitting flow through the primary fluid flow path. When the head portion is pushed down, flow is also permitted through a secondary fluid flow path from the inlet 624, through the chamber 620 and vent 628, to the outlet 618.

The port 662 at least partially defines a hollow sleeve 654 between the inlet 624 and the sealing surface 652. The sleeve 654 permits a fluid delivery device to be inserted into the port 662 a distance toward the sealing surface 652 before engaging the head portion 636 when the head portion 636 is not pushed down, as seen in FIG. 9D.

FIG. 9D shows the check valve member 680 in a closed configuration. In the closed configuration, a syringe 900 or other fluid connection is not connected to the inlet 624 of the port 662. The compressible portion 632 is in an uncompressed state such that the head portion 636 forms a fluid seal against the sealing surface to inlet 624 and the septum 640 remains closed. In the closed configuration, the primary fluid flow path and the secondary fluid flow path are occluded.

FIG. 9E shows the check valve member 680 in an open configuration. When a syringe 900 or other fluid connector is coupled to the port 662, the compressible member 630 is compressed such that head portion 636 dislodged from the sealing surface 652 and pushed down into the chamber 620. With the head portion 636 dislodged from the sealing surface 652, the septum 640 opens to permit flow through the primary fluid flow path illustrated by arrow A in FIG. 9E. With the head portion 636 dislodged from the sealing surface 652, flow is also permitted through the secondary fluid flow path illustrated by arrow B in FIG. 9E.

Referring to FIG. 9C, the cap 700 is rotatably coupled to the collar 702 through a hinge 704. The collar 702 extends around the port 662 and in some aspects, extends around the hollow sleeve 654. The hinge 704 extends from the collar 702 and permits the cap 700 to be biased toward and away from the inlet 624. In some embodiments, the hinge 704 is a living hinge.

The collar 702 is coupled to the wash port valve assembly 600 by inserting the port 662 into the collar 702. The collar 702 is configured to latch onto the wash port valve assembly 600. A wall of the collar 702 includes a notch 706, permitting an adhesive or other bonding material to be inserted into the notch 706. After the collar 702 is latched to the wash port valve assembly 600, the adhesive prevents the collar 702 from becoming unlatched or dislodged. In an embodiment, the port 662 and the collar 702 are a combined such that the hinge 704 extends directly from the port 662.

In an open state, the cap 700 is tethered or coupled to the wash port valve assembly 600 with the inlet 624 uncovered. In a covered state, the cap 700 is rotated to cover the inlet 624. In some aspects, the cap 700 engages the hollow sleeve 654 of the port 662 to cover the inlet 624. In some aspects, the cap 700 engages the collar 702, which extends around the port 662.

Figure 10A:
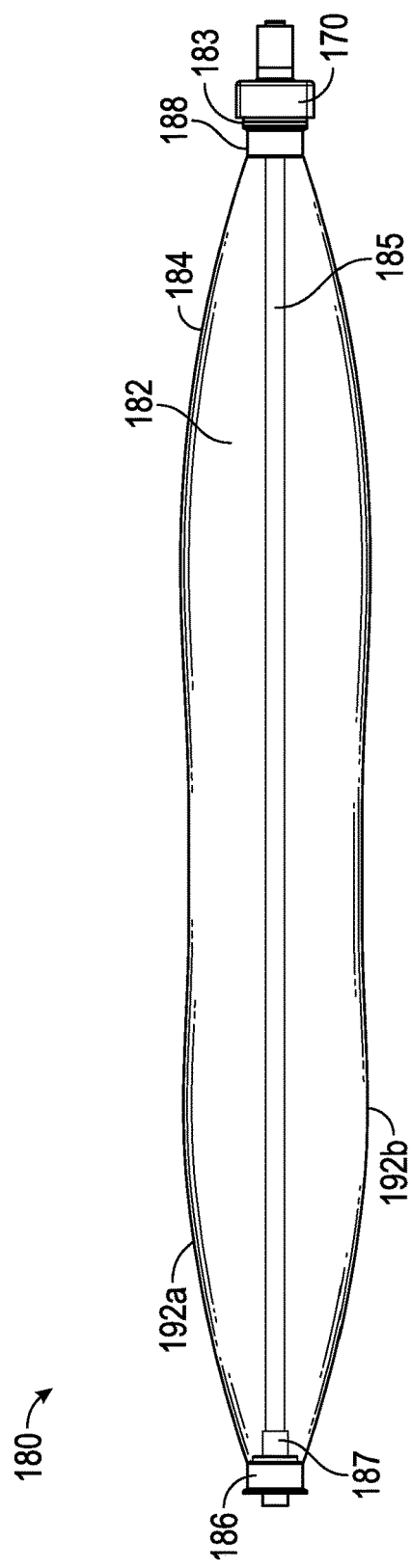
FIG. 10A illustrates a plan view of an example of a closed suction catheter sheath, in accordance with aspects of the present disclosure.
Figure 10B:
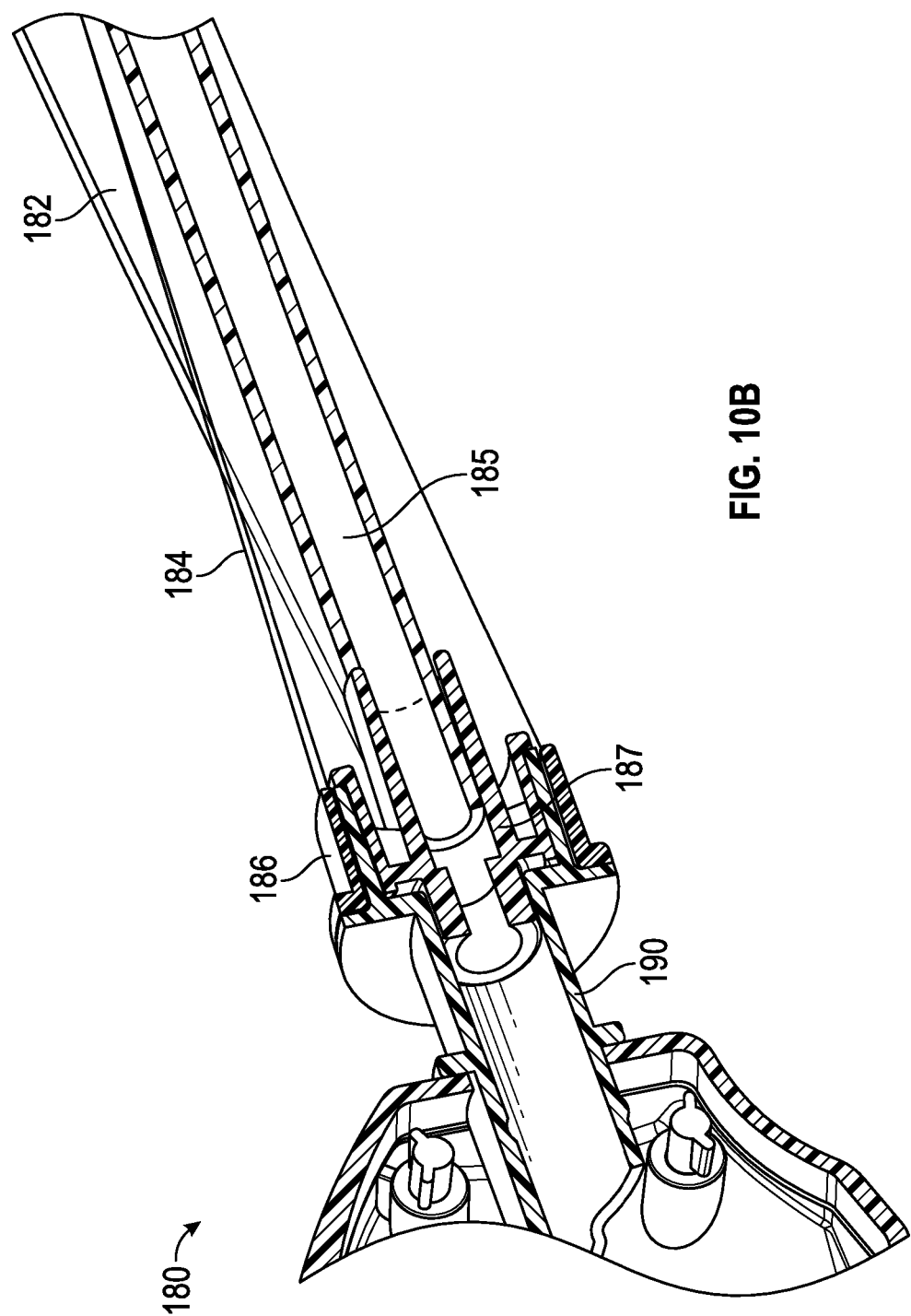
FIGS. 10B and 10C illustrate cross-sectional perspective views of the example closed suction catheter sheath of FIG. 10A, in accordance with aspects of the present disclosure.
Figure 10C:
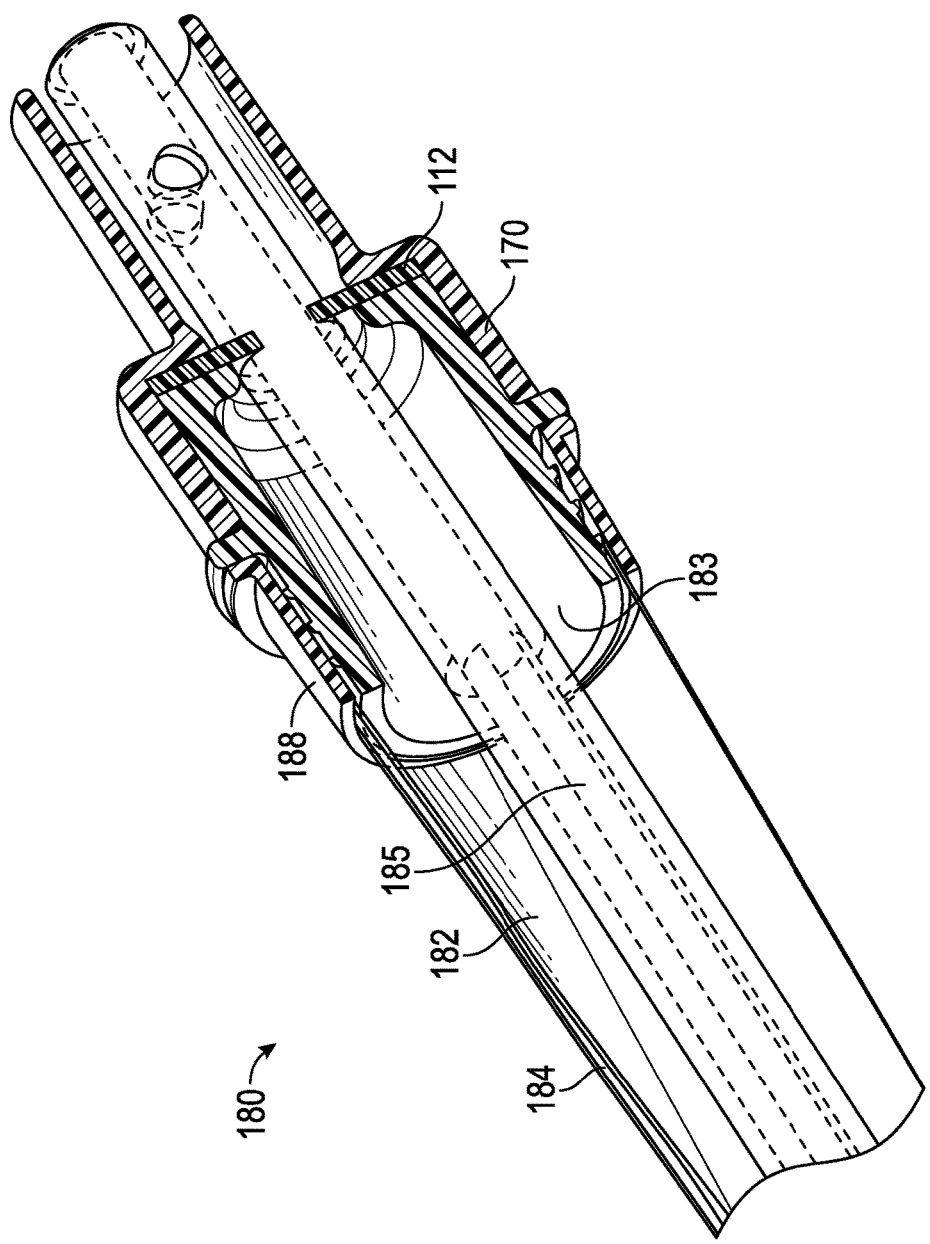

Referring to FIGS. 10A-10C, the suction catheter sheath 180 comprises a first end configured to be coupled to a suction control valve 190, and a second end configured to be coupled to a patient's artificial airway (not shown). The suction catheter sheath 180 comprises a sleeve 182 to enclose a suction catheter 185. The sleeve 182 provides a microbial barrier between the patient's airway and the environment and protects the caregiver from exposure to, for example, the patient's secretions.

The sleeve 182 is, in some embodiments, shaped as a cylinder having a lumen with an interior and exterior surface. The sleeve 182 can have various cross-sectional shapes, such as, for example, circular, oval, elliptical, polygonal (e.g., triangular, square or rectangular, pentagonal, hexagonal, etc.), acorn-shaped (i.e., with a sharp, converging side and an opposing rounded side), flat (i.e., with two flat sheets, one laying on top of the other connected at the edges), marquise, etc. In some embodiments, the sleeve 182 collapses upon itself because the walls of sleeve 182 are flexible and can be manipulated. For example, even though the sleeve 182 can be shaped as a cylinder or have some other configuration, when resting on a table, the sleeve 182 may appear as flattened layers resting atop each other. The sleeve 182 may be fabricated using an extrusion technique, blown film, or sheet film stock. The material may be made of polyether-based polyurethane. For example, a polyether-based polyurethane film of approximately 0.002 inches in thickness, with a hardness of approximately Shore—A80, may be used. The sleeve 182 material may also be selected for reduced noise characteristics, thereby minimizing sensory discomfort to the patient when the sleeve 182 is collapsed or expanded on the closed suction catheter 185.

The material may be textured or frosted on one or more surfaces. The texture may be located in a particular area of the sheath, improving grip or indicating proper usage of the device. For example, the exterior surface of the sleeve 182 may be textured in areas where the caregiver is intended to grasp the suction catheter sheath 180 during usage. The diameter of the sleeve 182 may be selected to prevent binding with the closed suction catheter 185 when the sleeve 182 is collapsed during insertion into a patient's artificial airway 165.

In some embodiments, the elongation capability of the suction catheter sheath 180 is limited by a cord 184 disposed along the longitudinal length of the sleeve 182. By limiting the elongation capacity of the closed suction catheter sheath 180, the distance that the catheter may be withdrawn from the artificial airway is thereby limited, preventing excessive or undesired elongation of the sleeve 182. Excessive or undesired elongation of the sleeve 182 (e.g., beyond the limit provided by the cord 184) may result in plastic deformation or damage to the sleeve 182, such as tearing of the sleeve 182 or slippage between the cord 184 and sleeve 182. The cord 184 may be any material that is axially rigid in tension to prevent undesired elongation and yet, radially flexible to allow the sleeve 182 to flex and compress in an accordion-like fashion. The cord 184 may be a single-strand or multiple strands. The strands may be parallel, twisted, woven, braided, or any combination thereof.

In some embodiments, the cord 184 is embedded within an interior or exterior wall of the sleeve 182. The sleeve 182 may comprise two or more layers, wherein the cord 184 is embedded between the layers. Where the sleeve 182 is fabricated from flat sheet film, the cord 184 may be placed between two strips of film along the long edge of the film 192a. Additionally, a second cord 184 may be placed along the opposite edge of the film 192b. The two layers of film may then be joined at their edges by welding, bonding, or any other suitable technique, and in some embodiments, the cord 184 may be contained within the weld or seam.

Using one strip of flat sheet film, the cord 184 may be placed on a long edge of the film 192a and the opposite edge of the film 192b folded onto the cord 184. The two edges may then be bonded retaining the cord 184 in the seam. In some embodiments the sleeve 182 is manufactured by extrusion. When manufactured by extrusion, the cord 184 may be embedded into a wall of the sleeve 182, as illustrated in FIGS. 10B-10C. For example, the cord 184 may be fed into the sleeve 182 material while in a liquid or viscous state prior to solidification. In some embodiments, the cord 184 is a material applied to a surface of the sleeve 182, or as an additional layer parallel with the sleeve 182. For example, a material having a limited elongation factor may be applied to the sleeve 182 in a lattice or weave pattern.

Referring to FIG. 10B, the suction catheter sheath 180 may be coupled to a suction control valve 190 having a suction catheter 185, in some embodiments, by sliding the suction catheter 185 through the lumen of the sleeve 182 such that the first end of the sleeve 182 is disposed around a suction catheter connector 187. A capture ring 186 may then be affixed around the sleeve 182 and suction catheter connector 187 at the first end. In some embodiments where the suction catheter connector 187 and suction catheter 185 are fixedly attached to a suction control valve 190, the capture ring 186 is disposed around a portion of the suction control valve 190. For example, the capture ring may be disposed around the fixed attachment of the catheter 185 and suction control valve 190. Referring to FIG. 10C, the second end of the sleeve 182 may be coupled to the suction catheter 185. The second end of the sleeve 182 is disposed around a suction catheter connector 183, and then a capture ring 188 is affixed around the second end of the sleeve 182. The suction catheter connectors 187 and 183 and capture rings 186 and 188 may be affixed using, for example, an interference fitting, threaded surfaces, and/or a compression coupling.

Still referring to FIG. 10C, the suction catheter connector 183 is a cylindrically shaped body with a lumen configured to allow the suction catheter 185 to slidably pass through the body. The suction catheter connector 183 may be coupled to a patient's artificial airway 165 through a coupler 170. In some embodiments, the suction catheter connector 183 or coupler 170 may be configured to couple directly to a patient's artificial airway 165 or to an airway adapter 100 as illustrated in FIG. 1A.

Referring back to FIG. 4, coupler 170 may comprise a cylindrical body having a lumen and transversely extending protrusions 174 (e.g., radially or parallel). The transversely extending protrusions 174 provide a torsional grip when the second end of the suction catheter sheath 180 is coupled or decoupled from a patient's artificial airway. The coupler 170 comprises a first end 176 and a second end 178. The first end 176 comprises a larger diameter than the second end 178. The first end 176 is configured to couple with the suction catheter connector 183. The second end 178 comprises a first diameter configured to couple with a patient's artificial airway, e.g., via an artificial airway adapter. Between the first end 176 and second end 178, a radial seat 220 is created in the lumen. In some embodiments, the coupler 170 is constructed of a clear material to allow for visual indication of catheter location through the coupler 170 and suction catheter sheath 180.

The suction catheter sheath 180 may be assembled by sliding the sleeve 182 over a catheter 185 (FIG. 10B) connected to a suction catheter connector 187, the suction catheter connector 187 is connected (e.g., fixedly) to a suction control valve 190 (FIG. 1A). A capture ring 186 is affixed over the sleeve 182 and the coupling of the suction catheter connector 187 and the suction control valve 190 (FIG. 10B). A second suction catheter connector 183 is then inserted onto the catheter 185 so that the second end of the sleeve 182 may be disposed between a capture ring 188 and the second suction catheter connector 183 (FIG. 10C). A coupler 170 having a wiper seal 172 may then be inserted onto the second suction catheter connector 183. Finally, the coupler 170 may be coupled to a patient's artificial airway 165 (FIG. 1A).

In use, the catheter 185 is advanced by a caregiver into the patient's artificial airway 165. As the catheter 185 is advanced into the patient's artificial airway, the suction control valve 190 causes the sheath 180 to collapse, as illustrated in FIG. 1A. When the catheter 185 is retracted, for example, to clean secretions accumulated on the catheter 185 surface, the sleeve 182 expands to its original length. The catheter 185 may be retracted until the catheter tip is between the wiper seal 172 and the patient's artificial airway 165 to prevent ventilator air from entering the sleeve 182. The caregiver may observe the location of the catheter 185 during retraction through the coupler 170, taking care not to allow the catheter 185 tip to enter the sleeve 182. To discourage the caregiver from retracting the catheter tip into the sleeve 182, the suction catheter sheath 180 is configured to reach an axial elastic elongation capacity before the catheter 185 tip enters the closed suction catheter sheath 180. Upon reaching the maximum elongation capacity of the sleeve 182, the caregiver will experience a spike in tensile resistance in the catheter assembly, alerting the caregiver that the catheter has reached its intended limit and that further elongation of the sleeve 182 and cord 184 will likely result in plastic deformation of the sleeve 182 or cord 184, tearing of the sleeve 182, or slippage between the sleeve 182 and cord 184.

However, it should be understood that, in accordance with certain embodiments, sleeve 182 is generally fluidly isolated from a ventilation zone or path by valve 120 when catheter 185 has been retracted through the valve and no suction force is applied to the catheter 185. In this regard, in the event that the tip of catheter 185 is inadvertently retracted beyond the aperture of wiper seal 172 and toward or into the sheath 185, the seal formed by valve 120 between the ventilation zone or path and the access zone or area to which the suction catheter sheath 180 is coupled will prevent the sheath 185 from filling with air from the ventilation zone or path. Thus, in some implementations, a suction catheter sheath may not include a cord or the like, for example.

FIGS. 11A-11D illustrate an example of a suction control valve. Suction control valve 190 may comprise a housing 191 having an interior cavity defined by a first side body 191A and a second side body 191B configured to mate for defining the interior cavity (e.g., a clamshell-type housing configuration). In accordance with certain embodiments, housing 191 of suction control valve 190 may be generally ellipsoid shaped, for example, approximating a tri-axial ellipsoid. Housing 191 of suction control valve 190 may comprise one or more arcuate detents 251 disposed along an external surface of the housing 191.

In certain embodiments, the one or more arcuate detents 251 may be transversely aligned with respect to the long axis of a tri-axial ellipsoid-shaped housing 191, and may be generally shaped as finger grips opposite of a thumb positioning location. However, the one or more arcuate detents 251 may be positioned or spaced along housing 191 at various locations applicable to a particular embodiment.

In this regard, housing 119 may provide ergonomic benefits to caregivers using suction control valve 190. For example, the generally ellipsoidal housing 191 may be sized and contoured so as to resemble a small, smooth "river rock" thereby making the suction control valve 190 comfortable to hold, turn, position, and secure in the hand, and operate without fatigue or discomfort. In certain embodiments, a tri-axial ellipsoidal housing 191 implementation may have a long axis of 5.5 cm to 6.5 cm, an intermediate axis of 3.5 cm to 4.5 cm, and a short axis of 1.5 cm to 2.5 cm. In some embodiments, the housing 191 may further comprise flat portions on one or both sides to facilitate incorporation of logos, identification graphics, stamping, marking or otherwise labeling the suction control valve 190.

Suction control valve 190 may further comprise a tubular segment 193 coupled to housing 191 such that at least a portion of the tubular segment 193 is disposed within the interior cavity defined by the housing 191. For example, the tubular segment 193 may extend through an opening on one end of the housing 191 so that a first end coupling 194 (e.g., a vacuum or suction source machine end) is accessible for removable coupling to a suction source 195. An opposite end of the tubular segment 193 may comprise a second end coupling or a capture ring 186 in some embodiments for connection to a catheter or other medical implement (e.g., a patient-facing side of suction valve assembly). For example, capture ring 186 of suction control valve 190 may be configured for permanent connection to a suction catheter or a closed suction catheter system in some embodiments.

Figure 11A:
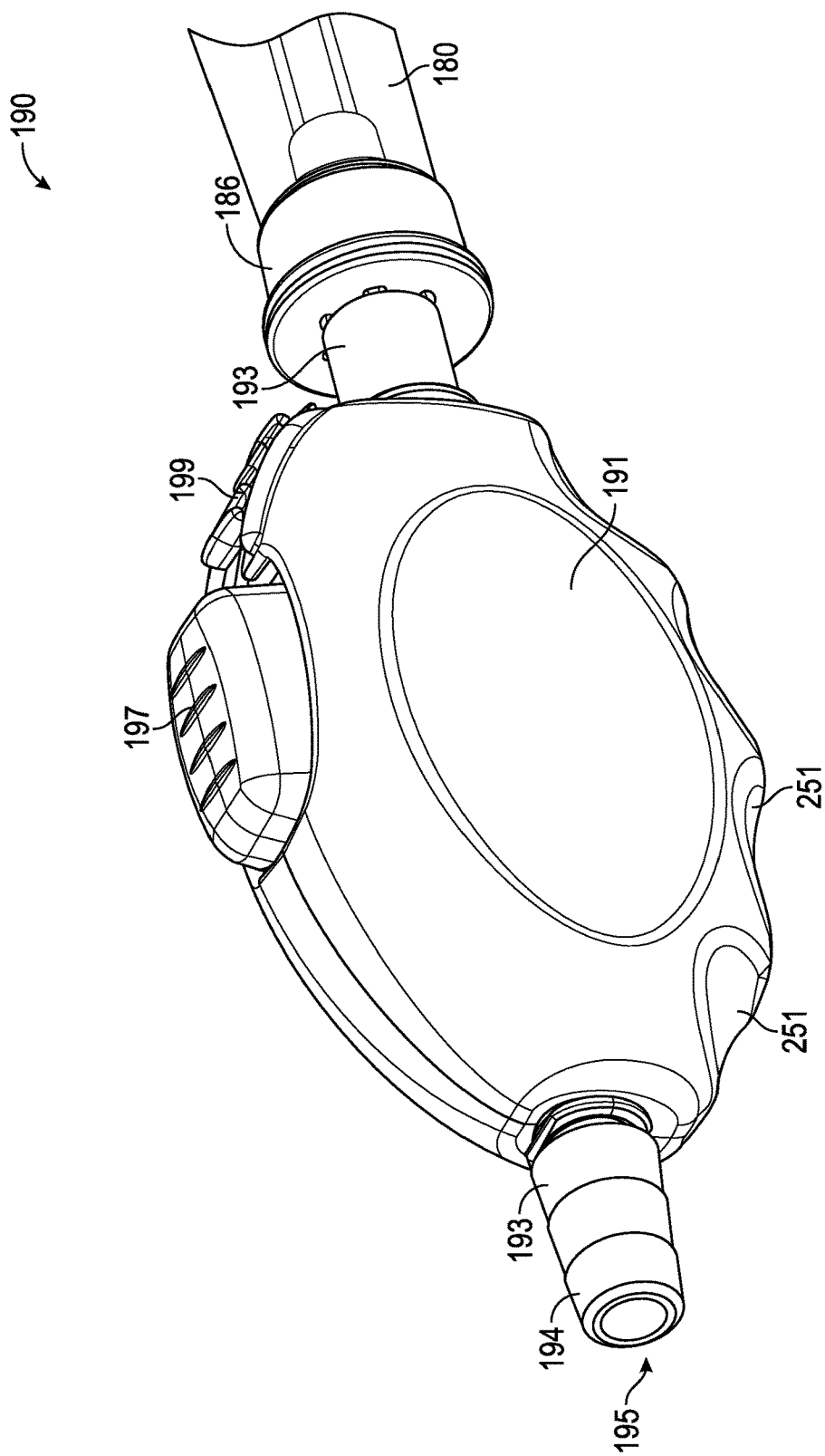
FIG. 11A illustrates a perspective view of an example of a suction control valve, in accordance with aspects of the present disclosure.
Figure 11B:
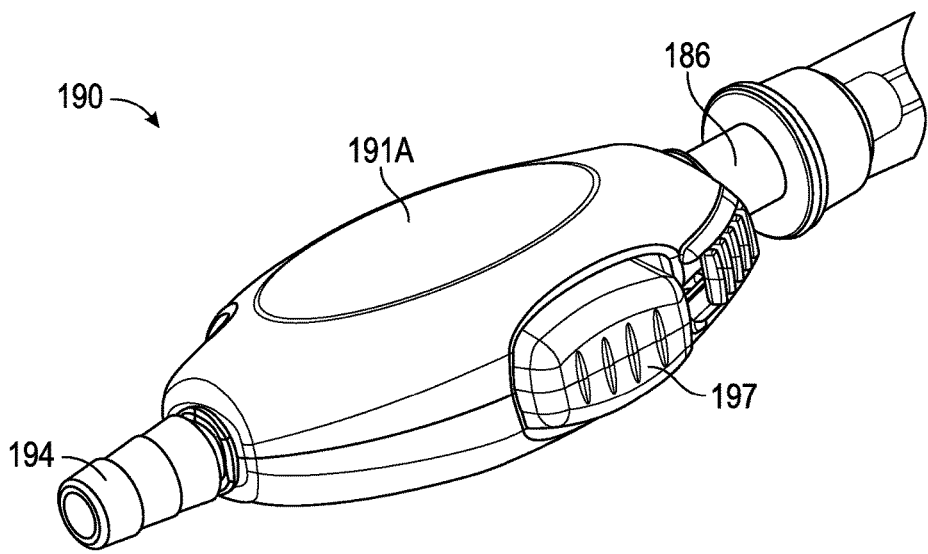
FIG. 11B illustrates a top perspective view of the example suction control valve of FIG. 11A, in accordance with aspects of the present disclosure.
Figure 11C:
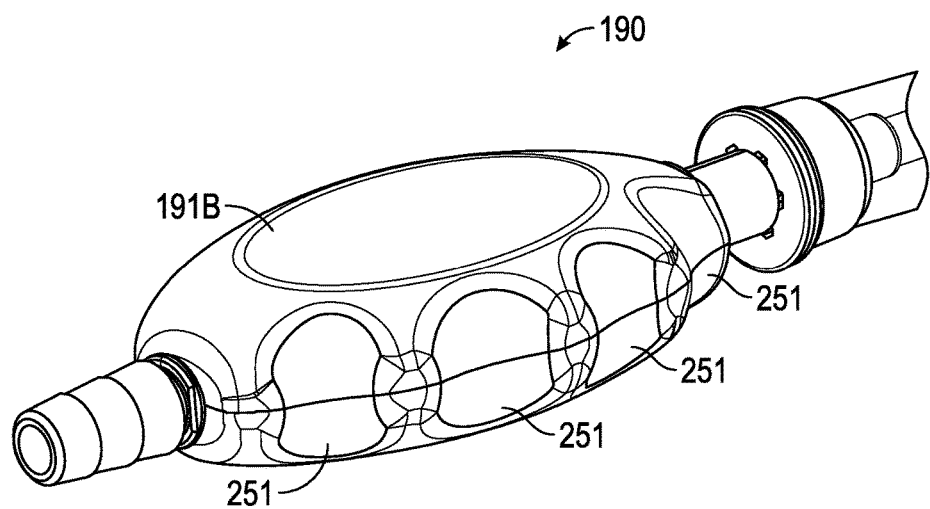
FIG. 11C illustrates a bottom perspective view of the example suction control valve of FIG. 11A, in accordance with aspects of the present disclosure.
Figure 11D:
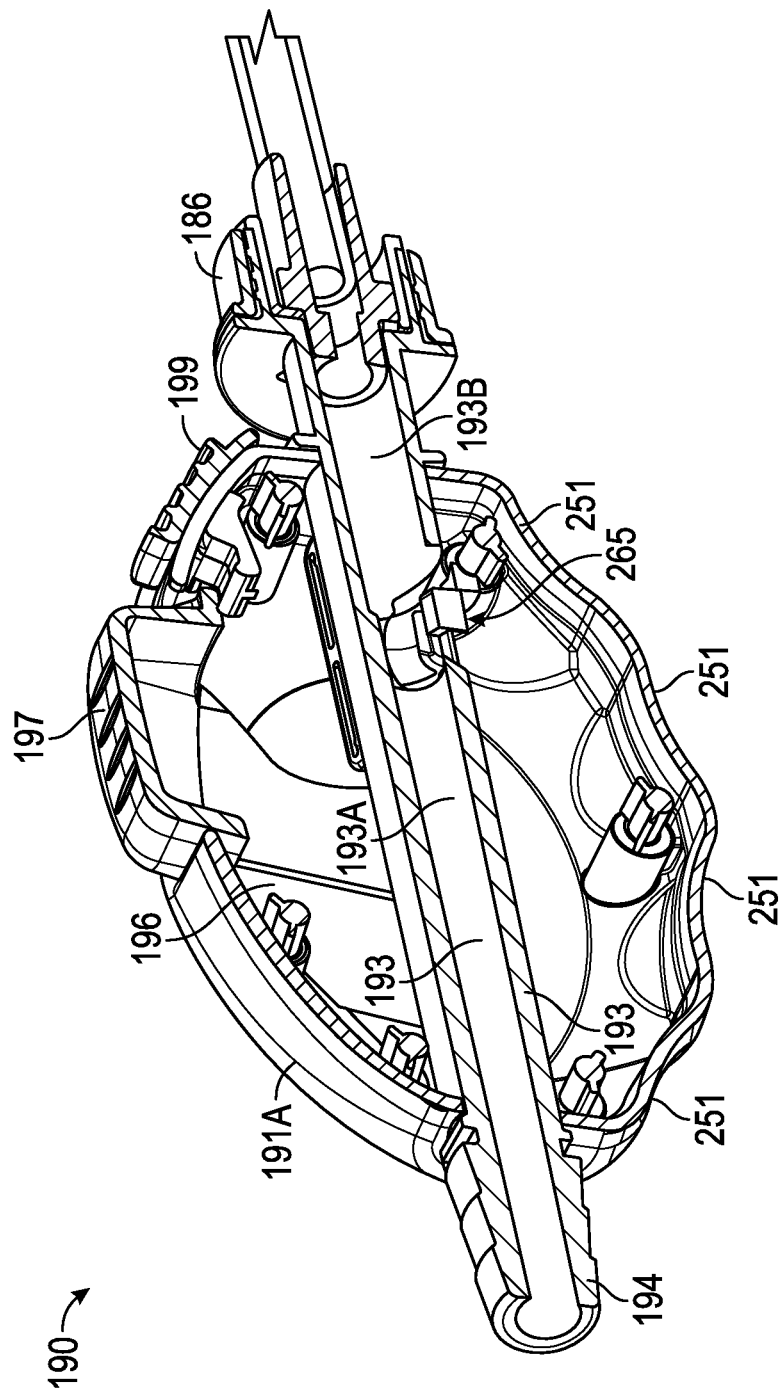
FIG. 11D illustrates a perspective cross-sectional view of an example of a suction control valve, in accordance with aspects of the present disclosure.

As shown in the example of FIG. 11D, a pathway may extend through the tubular segment 193, which includes an access opening 265 to the fluid pathway for providing valve gating features, in accordance with certain embodiments. For example, tubular segment 193 may comprise a first conduit segment 193a extending from first end coupling 194 and a second conduit segment 193b, which may be substantially axially aligned with the first conduit segment 193a that defines the fluid pathway through the suction control valve 190. Access opening 265 (e.g., an opening through a wall of tubular segment 193 transverse to the a longitudinal axis of the tubular segment 193) for valve gating features may be arranged between a valve end or side of the first conduit segment 193a and a valve end or side of the second conduit segment 193b. Second end coupling 198 may be disposed on a side of second conduit segment 193b opposite the valve end.

In certain embodiments, suction control valve 190 includes an actuator 196 for effectuating valve operations associated with access opening 265 and valve gating features therewith disclosed herein. Actuator 196 may comprise a button 197 having a top portion accessible via an opening of the housing 191. In certain embodiments, button 197 for activating or deactivating the suction operation of suction control valve 190 is located between a width of two sidewalls. In this regard, the button 197 of actuator 196 may be protected from accidentally being activated as it is retained within the physical sidewalls of the suction control valve 190.

Figure 12A:
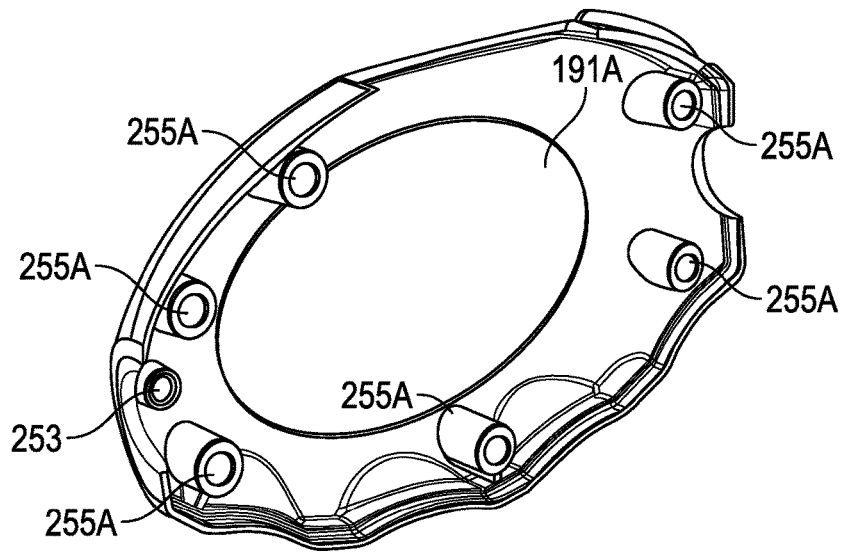
FIGS. 12A and 12B illustrate perspective views of examples of housing bodies, in accordance with aspects of the present disclosure.
Figure 12B:
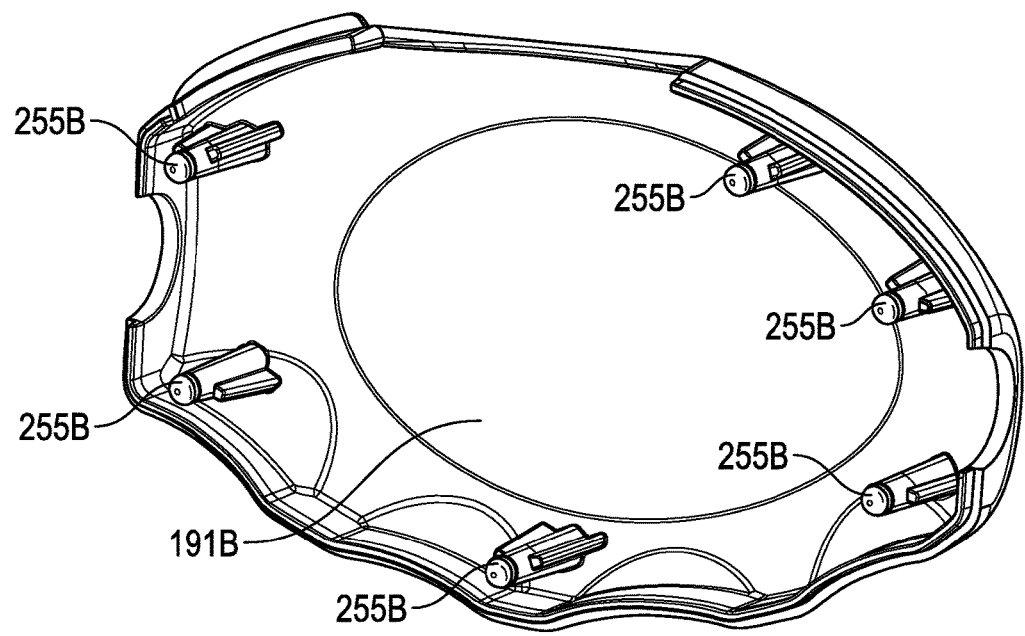

As shown in FIGS. 12A and 12B, the first side body 191A may include female fittings 255a and the second side body 191B may include corresponding male fittings 255b for connecting the first side body 191A and the second side body 191B to form housing 191. However, in some implementations, female fittings may be disposed on the first side body 191A and male fittings may be disposed on the second side body 191B. First side body 191A may also include a female fitting seat 253 for connection and alignment of tubular segment 193 to extend through an opening of housing 191. Additionally, or alternatively, other techniques of connecting the first and second side bodies 191A, body 191B together and securing tubular segment 193 to housing 191 may be used, for example, mating edge flange interconnection, adhesive coupling, cantilever snap connections, etc. Moreover, different housing shapes, sizes, and types are contemplated under the present disclosure.

FIGS. 13A-13D illustrate an example of a tubular section, which may include one or more tubular segments and/or end couplings in accordance with certain embodiments. Aspects of tubular segment 193 include one or more trunnion pins 261 for pivotal engagement with actuator 196. In some implementations, the one or more trunnion pins 261 may be disposed on the first conduit segment 193a of tubular segment 193. Additionally, first conduit segment 193a may include a pin 263 for engagement and alignment with housing 191, for example, with female fitting seat 253 of first side body 191A. Tubular segment 193 may further comprise harness 267 having a plurality of slots 269 for receiving a valve member operatively coupled to access opening 265 for providing valve-gating features.

Tubular segment 193 may be formed of a rigid polycarbonate, rigid acrylic, or other rigid thermoplastic material. In some embodiments, portions of tubular segment 193 may be formed from different materials (e.g., a less rigid plastic material used for first end coupling 194).

Figure 13A:
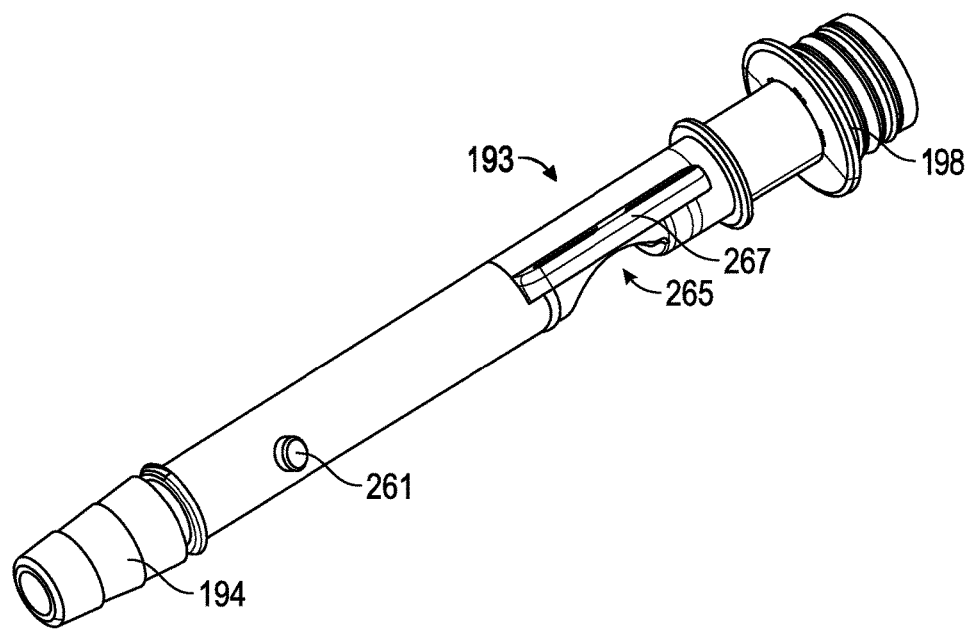
FIG. 13A illustrates a perspective view of an example of a tubular section of a suction control valve, in accordance with aspects of the present disclosure.
Figure 13B:
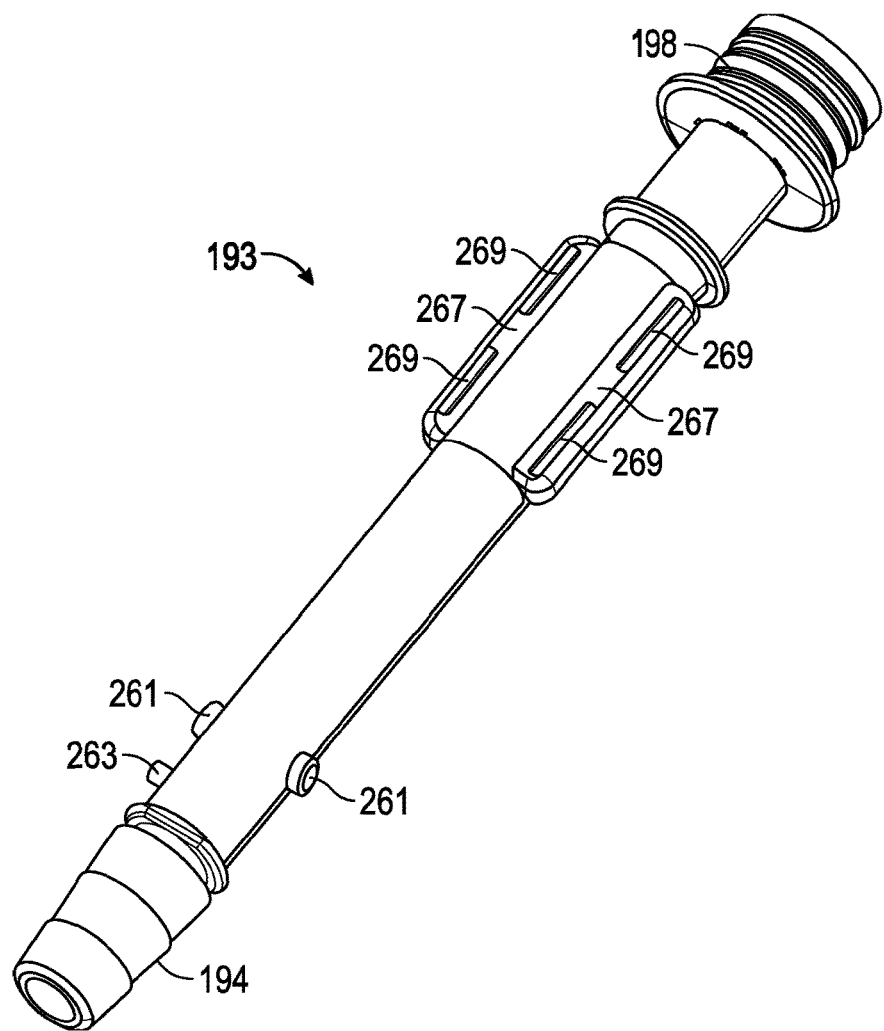
FIG. 13B illustrates a top perspective view of the example tubular section of FIG. 13A, in accordance with aspects of the present disclosure.
Figure 13C:
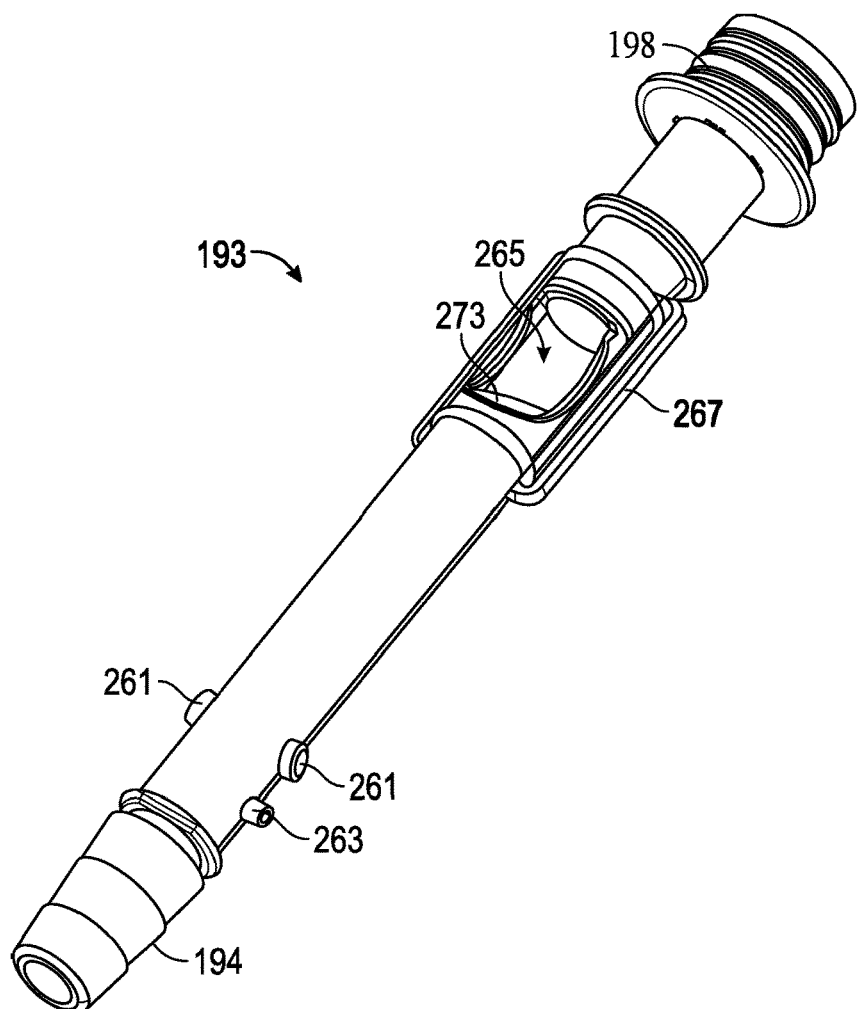
FIG. 13C illustrates a bottom perspective view of the example tubular section of FIG. 13A, in accordance with aspects of the present disclosure.
Figure 13D:
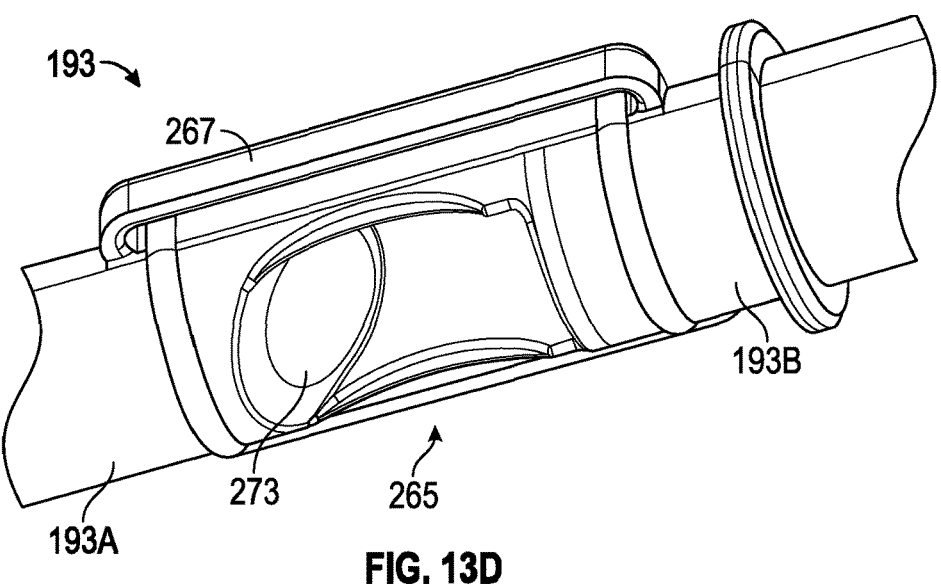
FIG. 13D illustrates a detail perspective of the example tubular section of FIG. 13A, in accordance with aspects of the present disclosure.
Figure 14A:
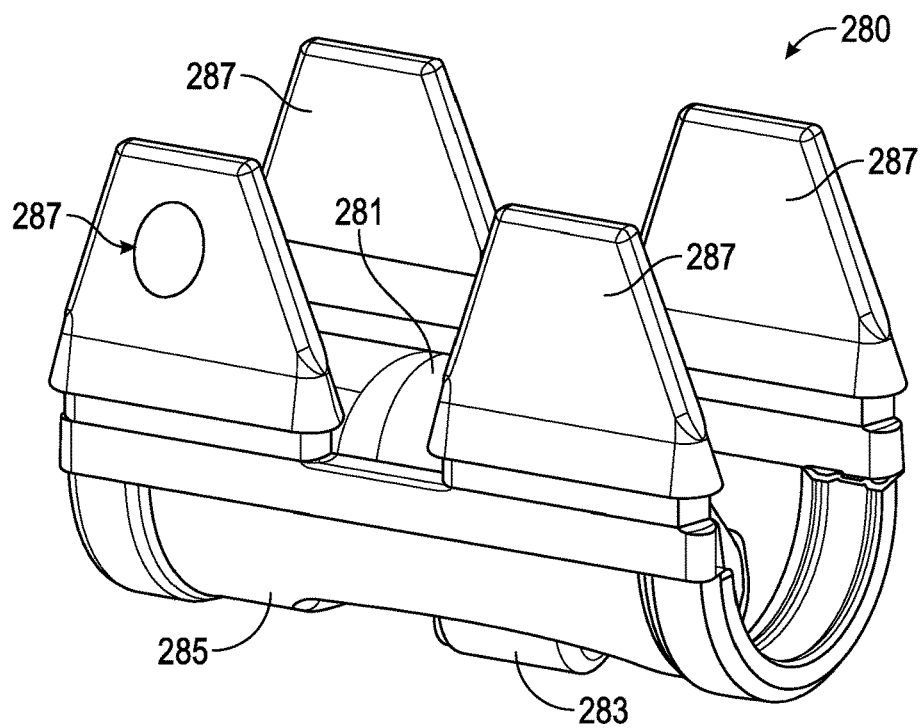
FIG. 14A illustrates a perspective view of an example of an elastomeric valve member, in accordance with aspects of the present disclosure.
Figure 14B:
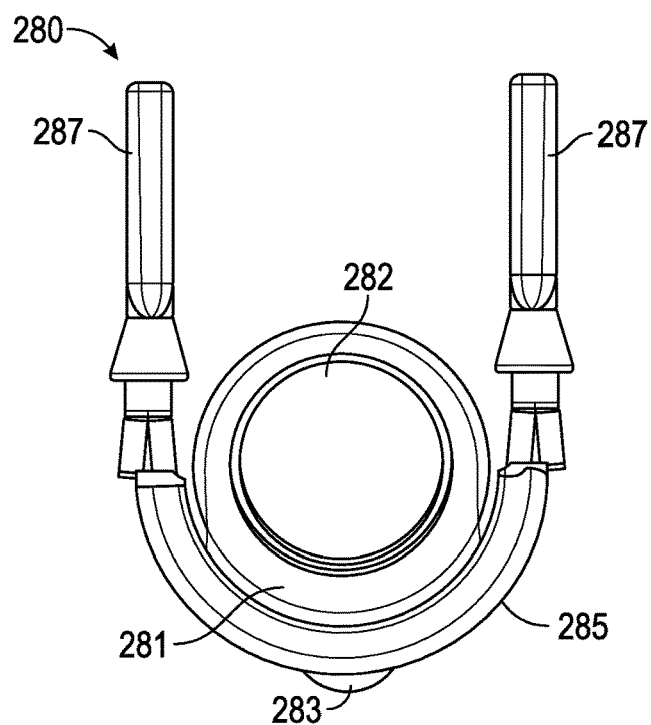
FIG. 14B illustrates a front view of an example of an elastomeric valve member, in accordance with aspects of the present disclosure.
Figure 14C:
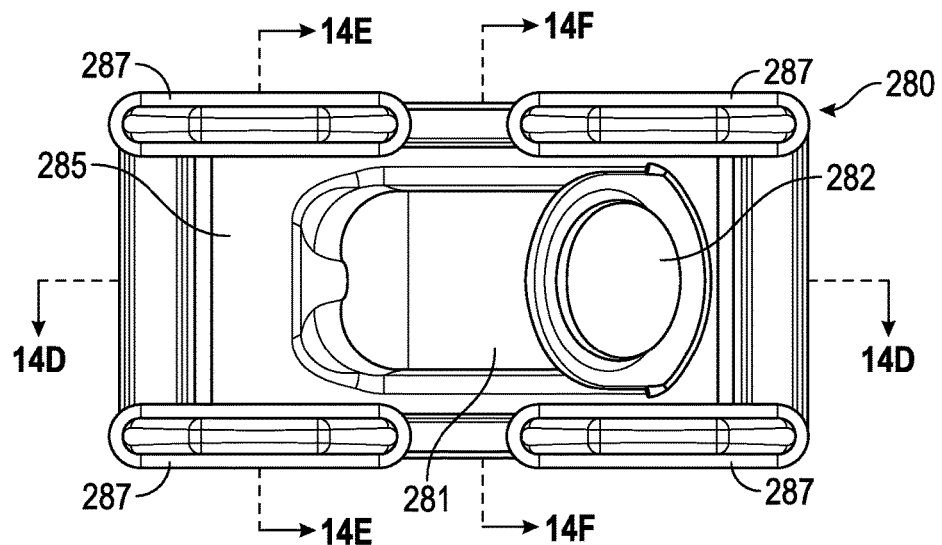
FIG. 14C illustrates a top view of an example of an elastomeric valve member identifying several cross-section lines, in accordance with aspects of the present disclosure.

As shown in the example of FIG. 13D, a valve seat 273 may be arranged at an end of first conduit segment 193a proximal to access opening 265. Valve seat 273 is configured to receive a valve plug 282 of the elastomeric valve member 280 (FIGS. 14B and 14C). In some embodiments, valve seat 273 may be angled with respect to a transverse plane of the first conduit segment 192a (e.g., at an angle oblique to the longitudinal axis of the first conduit segment 192a). Additionally, the valve seat 273 may comprise a step in inside diameters of the tube. Accordingly, an edge thickness of the valve seat is formed on which the valve plug 282 of the elastomeric valve member 280 can sealably engage when the valve member 280 is in a closed position, in certain embodiments.

FIGS. 14A-14F illustrate an example of an elastomeric valve member, in accordance with certain embodiments of the present disclosure. Suction control valve 190 includes an elastomeric valve member 280 comprising a valve body 281 and a protrusion 283. In certain embodiments, the valve body 281 may include a valve plug 282 for sealably engaging with valve seat 273 of tubular segment 193. In accordance with some implementations, valve member 280 can be coupled to and enclose the access opening 265 of the tubular segment 193. Protrusion 283 may be attached to actuator 196 for operating valve gating features provided on or in valve member 280 and access opening 265.

In certain embodiments, valve member 280 may be formed entirely from an elastomeric material, such as but not limited to, a silicone compound. However, in some embodiments, portions of valve member 280 may be formed from a more rigid material or co-molded with a more rigid material (e.g., fortifying a surface of protrusion 283). Valve member 280 may further include a cover portion 285 that serves to enclose the access opening 265 and adjacent areas to provide constitution of the fluid pathway through tubular segment 193, for example. A plurality of tabs 287 may extend from cover portion for securing the valve member 280 to the tubular segment 193 via the plurality of receiving slots 269 of harness 267. In other embodiments, valve member 280 may be attached to the tubular segment 193 by other techniques. For example, valve member 280 may be glued or clamped to the tubular segment 193.

Valve plug 282 may comprise a generally cylindrical or convex extension of elastomeric material configured to interface with valve seat 273. For example, valve plug 282 can have an interior facing wall surface of the bulbous wall segment normally biased toward the conduit segment 193a interior. An exterior facing wall surface of valve body 281 may be coupled to (e.g., attached or integrally formed with) the protrusion 283. In this regard, an angle of the valve seat 273 (FIG. 13D) may aid in urging or guiding valve plug 282 toward the aperture of conduit segment 193a, for example, when a suction source 195 is applied to first end coupling 194. Suction pressure from the suction source 195 may further assist in seating the valve plug 282 securely into the valve seat 273. Accordingly, fluid flow through the tubular segment 193 caused by a suction force provided at the second end coupling 198 and through the suction control valve 190 is ceased when valve plug 282 is securely seated into valve seat 273, in accordance with certain embodiments.

Figure 14D:
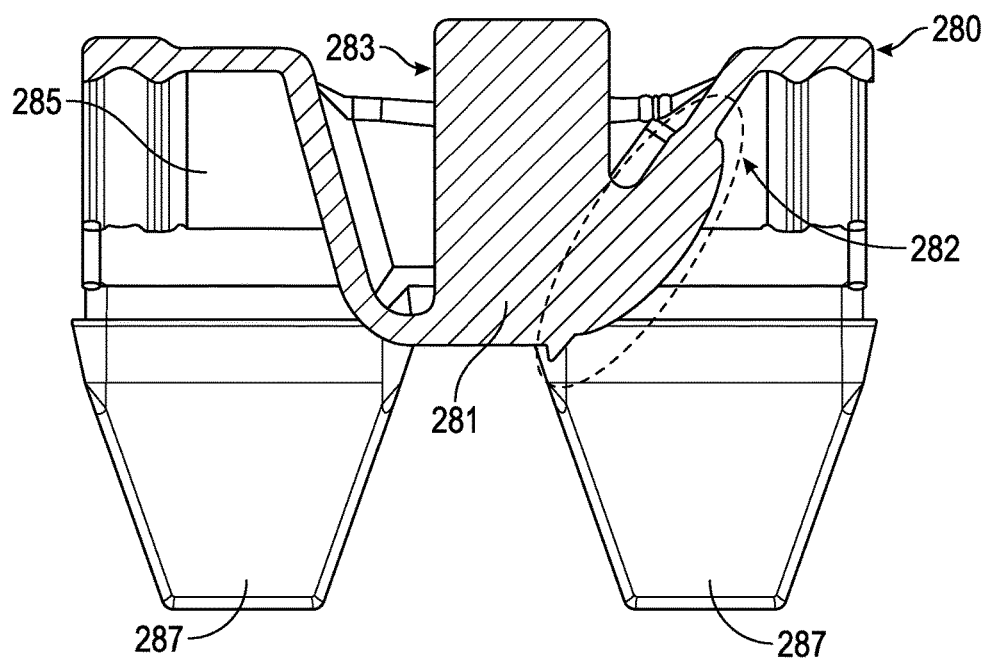
FIG. 14D is a cross-sectional view of the elastomeric valve member of FIG. 14C along cross section 14D, in accordance with aspects of the present disclosure.
Figure 14E:
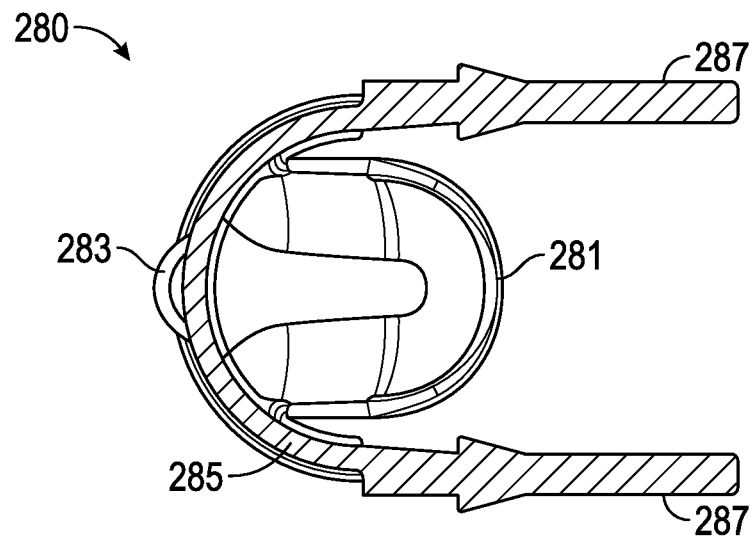
FIG. 14E is a cross-sectional view of the elastomeric valve member of FIG. 14C along cross section 14E, in accordance with aspects of the present disclosure.
Figure 14F:
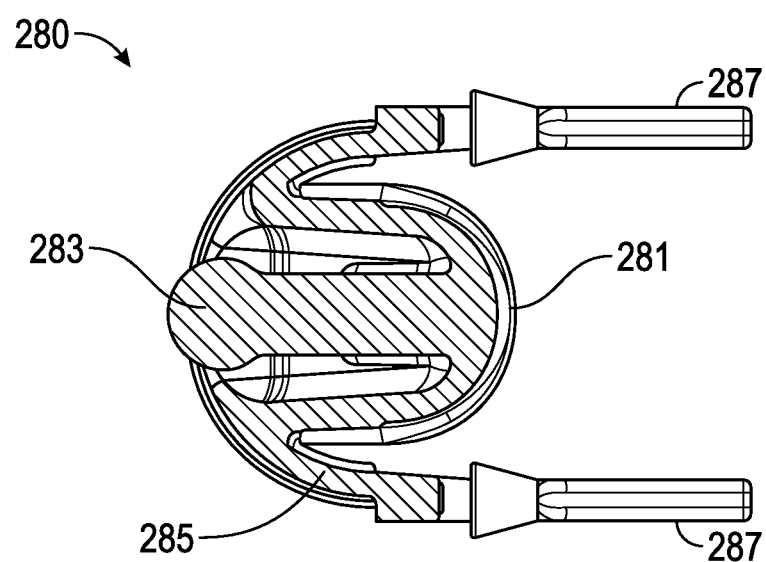
FIG. 14F is a cross-sectional view of the elastomeric valve member of FIG. 14C along cross section 14F, in accordance with aspects of the present disclosure.

Protrusion 283 of valve member 280 may be formed as an axially-oriented vertical wall portion extending outwardly from the interior of the inward-directed valve body 281 and valve plug 282 (e.g., when in an unbiased state). Protrusion 283 provides an attachment point for coupling to the actuator 196, for example. A wall area of body 281 provide a structure or mechanism for pulling the valve plug 282 outwardly away from the aperture of the first conduit 193a, thereby opening the fluid pathway of the tubular segment for suctioning operation. In this regard, the valve body 281 may be seen as inverted or bunched up within the valve member 280 around generally more linear protrusion portion 283 (FIGS. 14D and 14F). Moreover, the resilient and elastic properties of the valve member provide some springing or biasing force for returning (or inverting) the valve body 181 so as to align the valve plug 282 for sealed engagement with the valve seat 273.

Figure 15A:
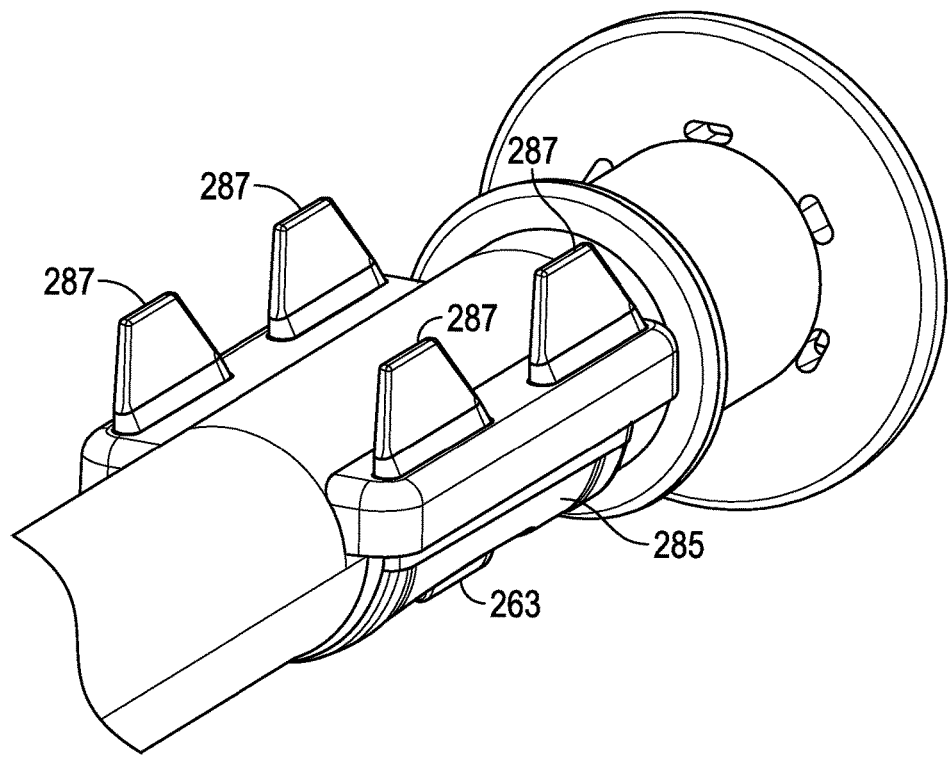
FIGS. 15A and 15B illustrate perspective views of examples of elastomeric valve members coupled to tubular sections, in accordance with aspects of the present disclosure.
Figure 15B:
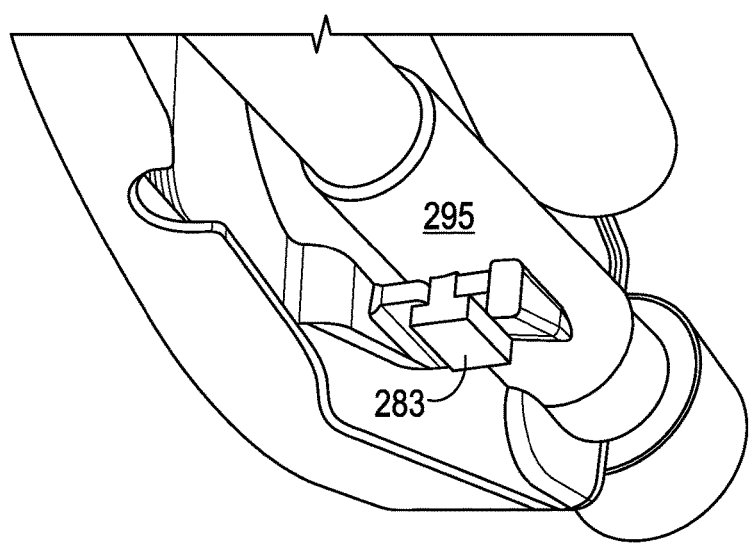

FIGS. 15A and 15B illustrate examples of elastomeric valve members coupled to tubular segments, in accordance with various aspects of the present disclosure. In the example of FIG. 15A, valve member 280 may be coupled to and enclosing the access opening 265 of the tubular segment 193. Cover portion 285 covers access opening 265 and includes a plurality of tabs 287 for coupling to harness 267 having a plurality of receiving slots 269 for securing valve member 280 to the tubular segment 193. In some implementations, the plurality of tabs 287 may be trimmed after insertion through the plurality of receiving slots 269. In this regard, space efficiency within the suction control valve 190 may be optimized, and the plurality of tabs 287 avoid interfering with the actuator 196 or other mechanisms within the interior of the suction control valve 190. The cover portion 285 and valve member 280 may be further pressure fitting, adhered, fused, or sealed around the edges of opening 265 in some fashion.

As shown in the example of FIG. 15B, valve member 280 may comprise a sleeve portion 295 in some embodiments. In such embodiments, sleeve portion 295 may include one or more ribs for aligning and sealing along tubular segment 193 that may include correspondingly mating one or more grooves, for example. The valve member 280 in the example of FIG. 15B may comprise similar aspects regarding valve body 181, valve plug 282, and protrusion 283 as described herein. Moreover, in a similar manner as discussed with respect to cover portion 285, certain portions of sleeve portion 295 may be sealed fused to tubular segment 193.

Figure 16:
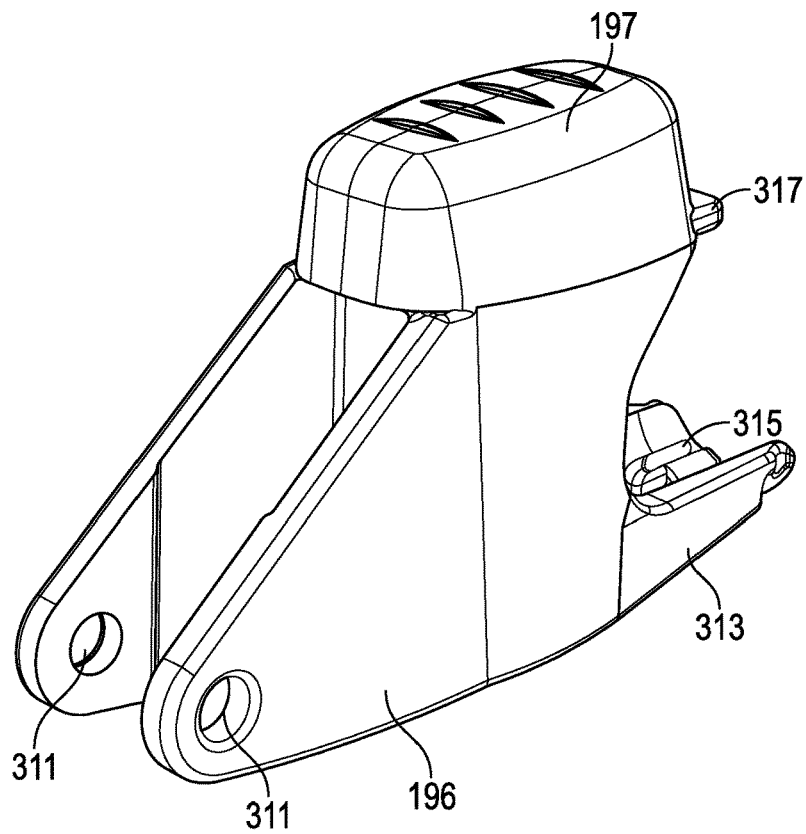
FIG. 16 illustrates a perspective view of an example of an actuator of a suction control valve, in accordance with aspects of the present disclosure.

FIG. 16 illustrates an example of an actuator structure of a suction control valve. In accordance with certain embodiments, actuator 196 may include one or more trunnion bores 311 for receiving one or more trunnion pins 261 disposed on an exterior surface of tubular segment 193 (FIG. 13A) such that actuator 196 is pivotably coupled to tubular segment 193. In some embodiments, one or more trunnion pins may be disposed on actuator 196 with receiving recesses disposed on the exterior surface of tubular segment 193, for example. It is to be understood that actuator 196 may be include other pivot point mechanisms or techniques for pivotably coupling to the actuator 196 to tubular segment 193. Moreover, in other embodiments, actuator 196 may be pivotably coupled to another area of the suction control valve 190, for example, trunnion pins disposed on opposite sides of first side housing body 191a and second side housing body 191b.

Actuator 196 may be formed of a rigid plastic or the like. In some embodiments, actuation may comprise a button 197, two walls extending from the button area comprising the one or more trunnion bores 311, whereby the walls are spaced apart so as to straddle tube segment 193. Actuator may also comprise a locking protrusion 317 for engagement with a lock 199 or locking mechanism, for example. In accordance with certain embodiments, actuator 196 may be a unitary piece. However, in other embodiments, certain aspects of actuator 196 may be separately, but interactively combined to provide an actuator structure for suction control valve 190 operation.

Actuator 196 may further comprise an actuation lever 313 coupled to the valve member 280. For example, the actuation lever 313 may be coupled to protrusion 283 of the valve member 280. During assembly, the protrusion 283 may be fixably adhered or fused to actuation lever 313 for securement thereto. In operation, the actuator 196 may be configured to move the actuation lever 313 and connected protrusion 283 along an arcuate path away from the access opening 265 so as to elastically deform the valve member 280. Accordingly, valve plug 282 may be advantageously pried away from valve seat 273 for valve opening operation due to the arcuate path defined by the actuation lever 313.

Figure 17:
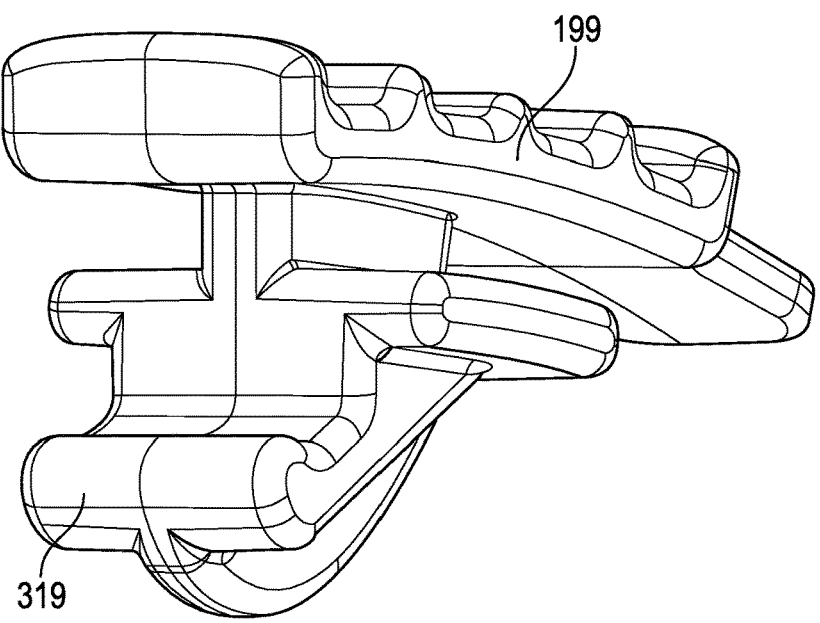
FIG. 17 illustrates a perspective view of an example of locking mechanism of a suction control valve, in accordance with aspects of the present disclosure.

FIG. 17 illustrates an example of a locking mechanism of a suction control valve. Lock 199 may be slidably movable along an exterior surface of the housing 191 and configured to engage with the actuator 196. Lock 199 may include a latch portion 319 for engaging with locking protrusion 317 of actuator 196. Accordingly, lock 199 can prevent button 197 and actuator 196 from articulating. Once the locking component is moved or slid away from the actuation lever, the lever can again be rotated. In this manner, the valve can be protected from accidental actuation.

When assembled in suction control valve 190, button 197 and lock 199 are positioned on housing 191 so that the button 197 and lock 199 may be accessible by a thumb of a hand of a user when one or more fingers of the user's same hand are aligned with the one or more arcuate detents arrange on the housing 191.

Figure 18A:
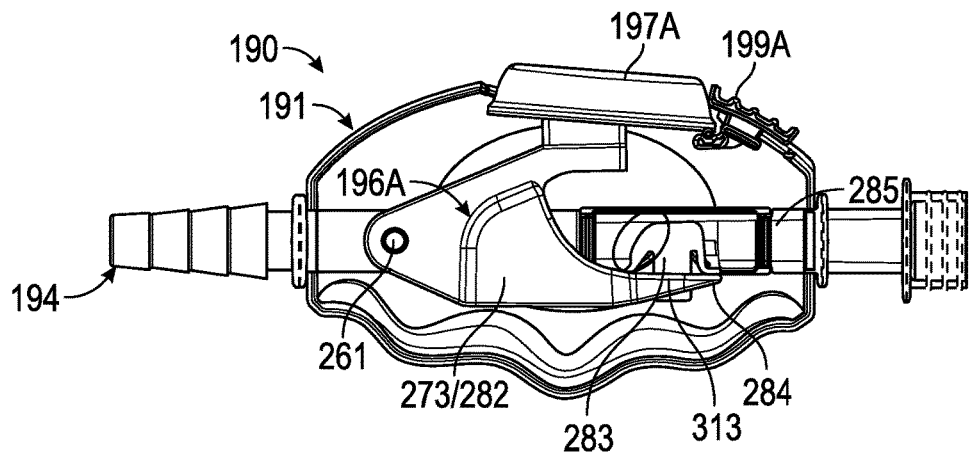
FIG. 18A illustrates a cross-section view of an example of a suction control valve in a first configuration, in accordance with aspects of the present disclosure.
Figure 18B:
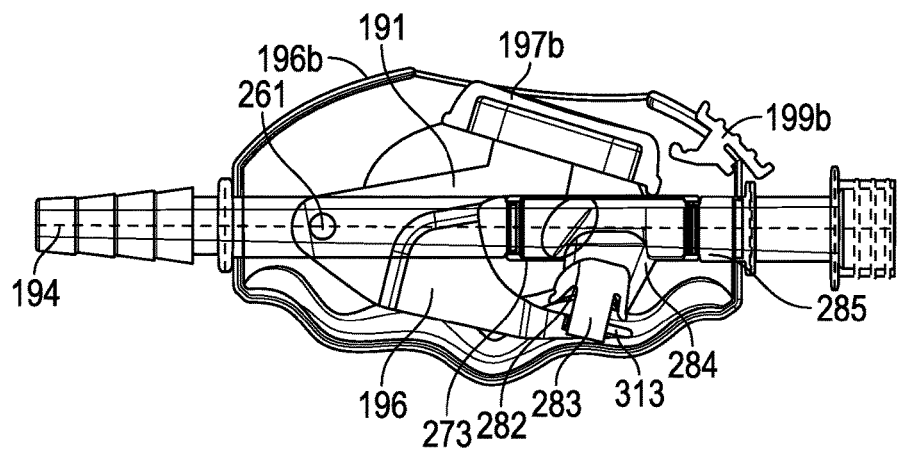
FIG. 18B illustrates a cross-sectional view of the example suction control valve in a second configuration, in accordance with aspects of the present disclosure.

FIG. 18A illustrates a cross-section view of an example of a suction control valve in a first configuration, and FIG. 18B illustrates a cross-sectional view of the example suction control valve in a second configuration, in accordance with certain aspects. For example, in FIG. 18A, features and components of suction control valve 190 may be in a first configuration (e.g., with respect to valve gating operation) such that valve plug 282 of valve member 280 is seated and occluding the fluid pathway of tubular segment 193.

In some embodiments, suction control valve 190 may comprise a biasing band 284 for coupling between the actuation lever 313 of the actuator 196 and the tubular segment 193 proximate to the access opening 265 area of the valve (e.g., aligned between segments of the harness 267 in some implementations). In such implementations, biasing band 284 may be configured to provide a biasing force against movement of the actuation lever 313 along an arcuate path away from the access opening 265. However, it is to be understood that other techniques for providing bias to the actuator 196 of suction control valve 190 may be employed in various embodiments. For example, a biasing mechanism may be located between a portion of housing 191 and a portion of actuator 196 (e.g., using a compression spring, leaf spring, cantilever mechanism, or other such biasing or spring member) so that actuation lever 313 may return to a position that causes valve member 280 to sealably engage with tubular segment 193.

In certain embodiments, the biasing band 284 may be a rubber O-ring or the like formed from a non-metallic material. It is to be appreciated that biasing member and suction control valve 190 may be configured so as to exclude any metallic elements (e.g., metal springs, pins, screws, etc.) in accordance with certain embodiments. Accordingly, such embodiments can continue to be used in emergency or routine procedure involving medical radiography (e.g., x-ray and CT scanning).

As illustrated in the example of FIG. 18A, lock 199 may be engaged with button 197 of actuator 196. In this regard, lock 199 may be configured to engage with the actuator 196 such that actuator 196 is restrained from articulating the protrusion 283 of the valve member 280 from a first position shown in FIG. 18A to a second position shown in FIG. 18B.

In certain embodiments, the valve member 280 of suction control valve 190 is configured such that, when the protrusion 283 is in the first position, the protrusion 283 is positioned at a contiguous space proximal to the access opening between first conduit segment 193a and second conduit segment 193b. As shown in the example of FIG. 18A, valve plug 282 is in contact with valve seat 273, thus blocking fluid flow. In this regard, protrusion 283 is external to an interior wall of the fluid pathway defined through the tubular segment 193.

As illustrated in the example of FIG. 18B, when a user or caregiver presses button 197, actuator 196 causes actuation lever 313 to pivot with respect to the trunnion pins 261 (or any other such pivot point mechanism) such that the actuation lever 313 pulls protrusion 283 of valve member 280 and thereby elastically deforming the valve member from an unbiased state or orientation. Accordingly, the actuation lever 313 acts to move the protrusion 283 and valve plug 282 of the valve member 280 in an arcuate manner defined by the rotation of the actuation lever 313 (e.g., downwardly in an arc toward an edge of housing 191). In this regard, sufficient rotation may be provided by the arrangement of the components such that the valve plug 282 and moves completely out of the fluid pathway, thereby providing an unobstructed path for the fluid flow.

Accordingly, in certain embodiments, valve member 280 may be configured such that valve plug 282 occludes the valve end of the first conduit segment when the protrusion 283 is in the first position (e.g., a closed configuration so that suction control valve 190 does not allow a suction force at the second end coupling 198). The valve member 280 may also be configured such that a contiguous space free from obstructions is formed internal to the valve member 280 between the valve seat 273 of first conduit segment 193a and a valve end of the second conduit segment 193b when the protrusion 283 is in the second position (e.g., an open configuration so that suction control valve 190 may allow a suction force at the second end coupling 198.

In accordance with some embodiments, the contiguous space between first conduit 193a and second conduit 193b within the valve member 280 enclosing the access opening 265 refers to a space that would allow an extension of the same cross-sectional area of the first conduit segment to extend across the access opening and connect to the second conduit segment 193b (e.g., the fluid pathway as if tubular segment 193 did not have an access opening and were a contiguous conduit from the first coupling end to the second coupling end).

It is to be understood that the process of inserting a suction catheter into a patient's airway and applying suction to the catheter within the patient's airway can be a traumatic event to an intubated or tracheostomy patient. Accordingly, efficient and effective suctioning procedures enabled by embodiments of suction control valve 190 are beneficial in certain patient care settings.

For example, a method for applying suction to an airway of a patient 13 (FIG. 2) may be performed by a caregiver (or other user) using a suction catheter coupled to a suction control valve (e.g., suction control valve 190). A caregiver 11 (FIG. 2) may secure an airway access point (e.g., an access port of airway adapter 100, endotracheal tube access or attachment point, or tracheostomy access or attachment point) with a first hand of the caregiver. Caregiver 11 may advance the suction catheter into an artificial airway of the patient 13 with a second hand. After the suction catheter has been inserted into the artificial airway a desired depth, the caregiver 11 may grasp the suction control valve with the second hand of the caregiver 11. The suction control valve may comprise a generally ellipsoidal housing including one or more arcuate detents, actuator structure including an actuator button having a top portion accessible via an opening of the housing, and a locking mechanism slidably movable along an exterior surface of the housing and configured to engage with the actuator structure. For example, to securely grasp the suction control valve, the caregiver 11 may align one or more fingers of the first hand with the one or more arcuate detents, and position a thumb of the first hand over a portion of the housing where the actuator button and locking mechanism are disposed.

In accordance with certain aspects, if, when caregiver 11 grasps the suction control valve with the second hand, the suction control valve is in a locked position, the caregiver may slide, with the thumb of the second hand, the locking mechanism of the suction control valve so as to unlock the actuator structure. This may be accomplished while keeping the first hand in contact with the airway access point. In this regard, the locking mechanism can be moved to the unlocked position one-handedly without releasing the first hand that is securing the airway access point into which the suction catheter is inserted. Moreover, the grip of the second hand on the suction control valve (e.g., the grip by one or more fingers curled around the one or more arcuate detents) may not require any adjustment to unlock the suction control valve as the actuator button and locking mechanism are positioned proximal to and configured to be operated by the thumb of the caregiver's hand holding the suction control valve. Accordingly, this aspect of the suction control valve and other aspects of the disclosure provide the advantage of keeping the airway access point stable, and avoiding discomfort to the patient 13 and excessive delays in withdrawing the catheter from the patient's airway.

Caregiver 11 may pull the suction control valve away from the airway access point to withdraw the suction catheter from the artificial airway of the patient 13. Caregiver 11 may depress the actuator button with the thumb of the second hand to cause suctioning of the suction catheter. During the withdrawal of the suction catheter thereby suctioning fluids, secretions, or the like from the airway of the patient 13, caregiver 11 may hold the actuator button in a biased position with the thumb of the second hand.

When the suctioning process is completed (e.g., the suction catheter is removed from the airway access point or a tip of the suction catheter aligned within a cleaning chamber of the airway adapter), caregiver may release the actuator button so as to allow the actuator button to return to an unbiased position. In this regard, when the actuator button is in the unbiased state, the suction force through the suction control valve applied to the suction catheter is ceased, in accordance with aspects of the present disclosure.

The subject technology is illustrated, for example, according to various aspects described above. Various examples of these aspects are described as embodiments. These embodiments are provided as examples and do not limit the subject technology.

In certain embodiments, a multiple-port airway adapter for connection to an artificial airway of a patient, may comprise a first port configured to be coupled to the artificial airway; a second port, distal from the first port, configured to be coupled to an auxiliary device, wherein a fluid pathway is formed between the first port and second port; and a third port comprising a conduit having a first end and a second end, the first end connected to the fluid pathway through an articulable connection such that the third port is articulable about the fluid pathway in at least two axes, and the second end being configured to be coupled to a ventilation device.

In some embodiments, the at least two axes may be offset by at least ten degrees.

In some embodiments, the articulable connection may comprise a ball and socket connection.

In some embodiments, the ball may be retained in the socket by a capture ring.

In some embodiments, the ball and socket connection may comprise a seal.

In some embodiments, the seal may be toroidal.

In some embodiments, the seal may be disposed about a circumference of the ball.

In other embodiments, the seal may disposed on the socket.

In some embodiments, a flexible tube may be disposed through the ball and socket connection between the first and second end of the third port.

In some embodiments, the flexible tube comprises a first end coupled to the fluid pathway and a second end extending through a cylindrical extension of the ball.

In some embodiments, the second end of the flexible tube comprises a radially extending flange.

In some embodiments, the radially extending flange is retained between an end of the cylindrical extension and a ventilator conduit coupler.

In some embodiments, the ventilator conduit coupler is connected over the articulable connection such that a ridge of the cylindrical extension engages a ridge of the ventilator conduit coupler.

In some embodiments, the second port comprises an articulable connection.

In some embodiments, the articulable connection comprises a flexible conduit.

In some embodiments, the flexible conduit comprises a wall having a corrugated shape.

In some embodiments, the flexible conduit comprises popple tubing.

In some embodiments, the flexible conduit comprises a wall having an elongate member axially extending between a first end and a second end of the flexible conduit. In some embodiments, the elongate member has a flexibility that is less than that of the flexible conduit. In certain embodiments, the elongate member comprises a wire.

In some embodiments, the first port comprises an articulable connection. In some embodiments, the articulable connection comprises a flexible conduit. In some embodiments, the flexible conduit comprises a wall having a corrugated shape, which in some embodiments, comprises popple tubing.

In some embodiments, both the first port and the second port comprise articulable connections, as described above.

In some embodiments, a flush port may be fluidly connected to the fluid pathway proximal to the second port.

In some embodiments, the flush port comprising a needleless valve having a compressible member with a hollow inner channel.

In some embodiments, the adapter may further comprise a valve that occludes the fluid pathway between the flush port and the third port, the valve having a leading edge proximal to the flush port and a trailing edge distal from the flush port.

In some embodiments, the adapter may further comprise a valve retaining structure formed along the fluid pathway between the flush port and third port, the valve retaining structure comprising an upper circumferential surface configured to engage the leading edge of the rim; and a lower circumferential surface configured to engage the trailing edge of the rim; and wherein at least one of the upper and lower surfaces forms a groove configured to receive the valve rim.

In some embodiments, a lens is disposed through an outside surface proximal to the second port.

In some embodiments, a distal most end of the first port may comprise an annular swivel feature coupled to the first port by an intermediate ring, the intermediate ring being disposed around the annular swivel feature and affixed to the first port.

In some embodiments, a distal end of the first port may comprise an annular swivel feature coupled to the first port by an intermediate ring, wherein the annular swivel feature is rotatable about an axis of the fluid pathway with respect to at least one of the intermediate ring or the first port.

In some embodiments, a distal end of the first port may comprise an annular swivel feature coupled to the first port by an intermediate ring, wherein the annular swivel feature comprises one or more transverse protrusions extending from a circumferential surface of the annular swivel feature.

In certain embodiments, a multiple-port airway adapter for connection to an artificial airway of a patient, may comprise a first port configured to be coupled to the artificial airway; a second port, distal from the first port, configured to be coupled to an auxiliary device, wherein a fluid pathway is formed between the first port and second port; a third port comprising a conduit having a first end and a second end, the first end connected to the fluid pathway through an articulable connection such that the third port is articulable about at least two axes, and the second end being configured to be coupled to a ventilation device; a fourth port coupled to the fluid pathway proximal to the second port; and a valve configured to occlude the fluid pathway between the third port and fourth port.

In certain embodiments, a multiple-port airway adapter system for connection to an artificial airway of a patient, may comprise a body comprising, a first port configured to be coupled to the artificial airway; a second port, distal from the first port, wherein a fluid pathway is formed between the first port and second port; a third port comprising a conduit having a first end and a second end, the first end connected to the fluid pathway through an articulable connection such that the third port is articulable about the fluid pathway in at least two axes, and the second end configured to be coupled to a ventilation device; a catheter coupled to the second port; and a ventilator device coupled to the third port.

In some embodiments, the body may further comprise a fourth port that is coupled to the fluid pathway between the second port and the third port.

In some embodiments, the multiple-port airway adapter system may further comprise a valve positioned within the body, the valve that is configured to occlude the fluid pathway between the second port and the fourth port.

In certain embodiments, a valve may comprise an outer rim section configured to engage with valve retention structure; and an inner resiliently flexible diaphragm section integrally connected to the outer rim section, the inner resiliently flexible diaphragm section comprising a plurality of valve segments defined by one or more slits, wherein one or more of the valve segments include one or more first regions and one or more second regions, the one or more first regions having a gradient thickness including a first thickness and a second thickness such that the second thickness is greater than the first thickness, the one or more first regions being disposed on the resiliently flexible diaphragm section at an intersection of at least some of the one or more slits, and the one or more second regions having a third thickness, greater than the second thickness of the one or more first regions, wherein a primary seal is formed by the plurality of valve segments, and wherein a secondary seal is formed by an arrangement of the one or more first regions of the plurality of the valve segments.

In some embodiments, a resealable opening of the secondary seal may be aligned with a resealable opening of the primary seal.

In some embodiments, the resealable opening of the secondary seal and the resealable opening of the primary seal may be aligned with an approximate center of the inner resiliently flexible diaphragm section.

In other embodiments, a resealable opening of the secondary seal may be located at a different position on the inner resiliently flexible diaphragm section than a center of a resealable opening of the primary seal.

In other embodiments, the resealable opening of the secondary seal may be located within the inner resiliently flexible diaphragm section proximal to the outer rim section and the resealable opening of the primary seal may be located at an approximate center of the inner resiliently flexible diaphragm section.

In some embodiments, one or more of the valve segments may further comprise one or more raised areas being thicker than the first thickness of the one or more first regions.

In some embodiments, the inner resiliently flexible diaphragm section may comprise an arcuate cross-sectional biasing feature disposed proximal to the outer rim section, and wherein the arcuate cross-sectional biasing feature may have an apex thickness greater than the first thickness of the one or more first regions.

In some embodiments, the arcuate cross-sectional biasing feature has an S-shape between the diaphragm section and the outer rim section.

In some embodiments, the one or more slits intersect at a point radially offset from an axis through the connector body.

In some embodiments, one or more minor slit extends from the one or more slits. In some embodiments, the one or more minor slit extends from the one or more slits at an end of the one or more slits. For example, in some embodiments, two minor slits extend from the end of the one or more slits, and the two slits extend at an angle from each other. In some embodiments, the angle is about 30 degrees.

In some embodiments, the outer rim section may define a circumferential drum volume of the valve, and the inner resiliently flexible diaphragm section are disposed within circumferential drum volume when the valve is in an unbiased configuration.

In some embodiments, the outer rim section and the inner resiliently flexible diaphragm section may comprise one of polysilicone, polyurethane, or polythermoplastic elastomer.

In certain embodiments, an airway adapter assembly may comprise a connector body portion having a first end and a second end, the connector body portion defining an elongate cavity having an axial center between the first and the second end; and a valve coupled to the second end of the connector body, the valve comprising: an outer rim section configured to engage with a valve retention structure; and an inner resiliently flexible diaphragm section integrally connected to the outer rim section, the inner resiliently flexible diaphragm section comprising a plurality of valve segments defined by one or more slits, wherein one or more of the valve segments include one or more first regions and one or more second regions, wherein a primary seal is formed by the plurality of valve segments, and a secondary seal is formed by an arrangement of the one or more first regions of the plurality of the valve segments, and wherein the secondary seal has a first cracking pressure, and the primary seal has a second cracking pressure different from the first cracking pressure.

In some embodiments, the first cracking pressure may be less than the second cracking pressure.

In some embodiments, the first cracking pressure may be within a range between 68 cm $H_2O$ and 188 cm $H_2O$.

In some embodiments, the one or more first regions may have a gradient thickness including a first thickness and a second thickness such that the second thickness is greater than the first thickness, and the one or more second regions having a third thickness, greater than the second thickness of the one or more first regions.

In some embodiments, the connector body portion may further comprise a flush port disposed between the first end and the second end, the flush port being in fluid communication with the elongate cavity.

In some embodiments, the airway adapter assembly may further comprise an airway adapter coupler coupled to the first end of the connector body portion, the airway adapter coupler comprising a wiper seal with an access aperture, and configured to receive a medical implement for accessing the elongate cavity of the connector body portion; and a ventilation base member comprising a tubular portion coupled to the second end of the connector body portion.

In some embodiments, the valve member may be configured such that the primary and secondary seals provide a fluid barrier between the elongate cavity of the connector body portion and a ventilation chamber of the ventilation base member.

In some embodiments, the ventilation base member may further comprise a manifold structure having a respiratory conduit section and a ventilation source opening, the ventilation source opening being fluidly coupled to the tubular portion and the respiratory conduit section, and wherein the valve member may be disposed adjacent to an end of the tubular portion such that the valve is not located in a direct fluid pathway from the ventilation source opening and the respiratory conduit section.

In accordance with certain embodiments, a method for cleaning a catheter in a suction catheter system may comprise aligning a tip end of a suction catheter within an access zone of an airway adapter such that the tip end of a suction catheter is positioned between a valve and an airway adapter coupler, wherein the valve includes a plurality of valve segments configured to form a primary seal and a secondary seal, each of the primary and secondary seals providing a breachable seal between the access zone and a ventilation zone of the airway adapter, and wherein the airway adapter coupler includes a wiper seal with an access aperture configured to provide a slidably frictional fitting with the suction catheter; injecting a solution into a flush port of the airway adapter that is in fluid communication with the access zone; and applying a suction force to the suction catheter such that the secondary seal of the valve is breached, causing airflow from the ventilation zone into the access zone.

In some embodiments, the method may further comprise extending the suction catheter through the access zone of the airway adapter into the ventilation zone of the airway adapter such that the primary seal formed by the plurality of valve segments is breached and at least some of the valve segments extend toward the ventilation zone.

In some embodiments, the method may further comprise retracting the suction catheter in a direction from the ventilation zone to the access zone such that the at least some of the valve segments extend toward the access zone.

In certain embodiments, an elongation limiting closed suction catheter sheath may comprise a flexible sleeve for enveloping a closed suction catheter, the sleeve having a first end and a second end; and a cord, having a cord length, embedded within a wall of the flexible sleeve, the cord being configured to limit axial elastic elongation of the sleeve along the cord length.

In some embodiments, an exterior surface of the sleeve may comprise texturing.

In some embodiments, the cord may have a length that is substantially the same length as the flexible sleeve.

In some embodiments, the sleeve may comprise two or more layers.

In some embodiments, the cord may be embedded onto an exterior layer of the two or more layers.

In some embodiments, the cord may be embedded between two layers of the sleeve.

In some embodiments, the cord may comprise a layer of the flexible sleeve.

In some embodiments, the sleeve may be formed by extruding the sleeve with the cord embedded into a wall of the sleeve.

In some embodiments, the sleeve may be formed from a flat sheet, folded along an intermediate portion between edges of the flat sheet, wherein the edges are bonded together and the cord is embedded between the bonded edges.

In some embodiments, the sleeve may be comprised two or more flat sheets bonded along long edges of each sheet, wherein at least one cord is embedded between the two or more flat sheets where the edges are bonded.

In some embodiments, a capture ring may be disposed on an end of the sleeve.

In some embodiments, the sleeve may comprise a polyurethane film of approximately 0.002 inches in thickness with a hardness of approximately Shore—A80.

In certain embodiments, an elongation limiting closed suction catheter sheath may comprise a flexible sleeve for enveloping a closed suction catheter, the sleeve having a first end and a second end; a cord, having a cord length, embedded within a wall of the flexible sleeve, the cord being configured to limit axial elongation of the sleeve along the cord length; wherein the flexible sleeve has a capture ring at the first end configured to be coupled to a catheter; and wherein the flexible sleeve has a capture ring at the second end configured to be coupled to a suction catheter connector.

In some embodiments, the suction catheter connector may be configured to be coupled to an artificial airway via a coupler, and wherein the coupler comprises radially extending protrusions on an external surface.

In some embodiments, the catheter may be fixedly attached to a suction valve and the capture ring is disposed around the fixed attachment of the catheter and suction valve.

In some embodiments, a seal may be disposed between the second end and the artificial airway, the seal having an aperture such that the catheter may slidably pass through the seal.

In certain embodiments, a method for limiting the elongation of a closed suction catheter sheath, may comprise embedding a cord within a wall of a flexible sleeve having a first end and a second end; joining the first end of the sleeve to a suction catheter such that the catheter is enveloped by the sleeve; joining a second end of the sleeve to an artificial airway; and wherein a distance the catheter may be withdrawn into the sleeve is limited to a length of the cord.

In some embodiments, the method may further comprise embedding the cord onto an exterior wall of the sleeve.

In some embodiments, the method may further comprise embedding the cord between two or more layers of the flexible sleeve.

In some embodiments, the method of claim 17 may further comprise disposing a seal having an aperture between the second end and the artificial airway.

In certain embodiments, a suction control valve assembly may comprise a housing having an interior cavity of the housing; a rigid tubular section coupled to the housing and having at least a portion of the rigid tubular section disposed within the interior cavity of the housing, the rigid tubular section having a first end, a second end, a pathway extending between the first end and the second end, and a pathway access opening arranged between the first end and the second end; an elastomeric valve member being coupled to and enclosing the pathway access opening of the rigid tubular section; and a pivotable actuator structure having a lever portion coupled to the elastomeric valve member, wherein the lever portion is configured to move along an arcuate path away from the pathway access opening so as to elastically deform the elastomeric valve member.

In some embodiments, the elastomeric valve member may comprise a cover portion having a plurality of taps wherein the rigid tubular section comprises a harness having a plurality of slots, and wherein the plurality of tabs are coupled to the plurality of slots for securing the elastomeric valve member to the rigid tubular section.

In other embodiments, the elastomeric valve member may comprise a sleeve portion having one or more ribs or grooves, and wherein the rigid tubular section comprises one or more corresponding grooves or ribs, and wherein the one or more ribs are aligned with the one or more grooves for sealing the elastomeric valve member against the rigid tubular section.

In some embodiments, the rigid tubular section may further comprise a pivot point mechanism disposed on an external surface, and wherein the pivotable actuator structure is coupled to the pivot point mechanism.

In some embodiments, the pivotable actuator structure may comprise an actuator button having a top portion accessible via an opening of the housing.

In some embodiments, the pivotable actuator structure may be a unitary piece.

In some embodiments, the suction control valve assembly may further comprise a biasing member coupled between the lever portion of the pivotable actuator structure and the rigid tubular section, wherein the biasing member is configured to provide a biasing force against movement of the lever portion along the arcuate path away from the pathway access opening.

In some embodiments, the suction control valve assembly may further comprise a locking mechanism slidably movable along an exterior surface of the housing and configured to engage with the pivotable actuator structure.

In some embodiments, the housing may be generally ellipsoid shaped.

In some embodiments, the housing may comprise one or more arcuate detents disposed along an external surface of the housing.

In certain embodiments, a suction control valve assembly for controlling suction to a suction catheter, may comprise a housing having an interior cavity of the housing; a rigid tubular section coupled to the housing and having at least a portion of the rigid tubular section disposed within the interior cavity of the housing, the rigid tubular section defining a fluid pathway and comprising a first conduit segment having a suction source end and valve end, a second conduit segment substantially axially aligned with the first conduit segment and having a catheter end and a valve end, and a pathway access opening arranged between the valve end of the first conduit segment and the valve end of the second conduit segment; an elastomeric valve member comprising an attachment protrusion and a plug portion, the elastomeric valve member being coupled to and enclosing the pathway access opening of the rigid tubular section; and an actuator structure coupled to the attachment protrusion of the elastomeric valve member configured to articulate the attachment protrusion from a first position to a second position, wherein the elastomeric valve member is configured such that (i) the plug portion occludes the valve end of the first conduit segment when the attachment protrusion is in the first position and (ii) a contiguous space free from obstructions is formed between the valve end of the first conduit segment and the valve end of the second conduit segment when the attachment protrusion is in the second position.

In some embodiments, the elastomeric valve member may be further configured such that, when the attachment protrusion is in the first position, the attachment protrusion is positioned at the contiguous space between the valve end of the first conduit segment and the valve end of the second conduit segment.

In some embodiments, the valve end of the first conduit segment may comprise a valve seat configured to receive the plug portion of the elastomeric valve member.

In some embodiments, the valve seat may be angled with respect to a transverse plane of the first conduit segment.

In some embodiments, the suction control valve assembly may further comprise a biasing member coupled to rigid tubular section and the actuator structure, wherein the biasing member is configured to provide a biasing force against articulating the attachment protrusion from the first position to the second position.

In some embodiments, the biasing member may comprise a non-metallic material.

In some embodiments, the suction control valve assembly may further comprise a locking mechanism slidably movable along an exterior surface of the housing and configured to engage with the pivotable actuator structure, wherein the locking mechanism is configured to engage with the actuator structure such that actuator structure is restrained from articulating the attachment protrusion of the elastomeric valve member from the first position to the second position.

In certain embodiments, a method for applying suction to an airway of a patient performed by a caregiver using a suction catheter coupled to a suction control valve, may comprise securing an airway access point with a first hand of the caregiver; advancing the suction catheter into an artificial airway of the patient with a second hand of the caregiver; grasping the suction control valve with the second hand of the caregiver, wherein the suction control valve comprises a generally ellipsoidal housing including one or more arcuate detents, an actuator structure including an actuator button having a top portion accessible via an opening of the housing, and a locking mechanism slidably movable along an exterior surface of the housing and configured to engage with the actuator structure; pulling the suction control valve away from the airway access point to withdraw the suction catheter from the artificial airway; and depressing the actuator button with the thumb of the second hand to cause suctioning of the suction catheter.

In some embodiments, the airway access point may comprise an access port of an airway adapter.

In some embodiments, the method may further comprise if, when grasping the suction control valve with the second hand, the suction control valve is in a locked position, sliding, with the thumb of the second hand, the locking mechanism of the suction control valve so as to unlock the actuator structure, while keeping the first hand in contact with the airway access point.

In some embodiments, an airway adapter assembly includes a connector body portion having a first end and a second end, the connector body portion defining an elongate cavity having an axial center between the first and the second end; a valve coupled to the second end of the connector body, the valve comprising an outer rim section configured to engage with a valve retention structure and an inner resiliently flexible diaphragm section integrally connected to the outer rim section, the inner resiliently flexible diaphragm section comprising a plurality of valve segments defined by one or more slits, wherein one or more of the valve segments include one or more first regions and one or more second regions, wherein a primary seal is formed by the plurality of valve segments, and a secondary seal is formed by an arrangement of the one or more first regions of the plurality of the valve segments, and wherein the secondary seal has a first cracking pressure, and the primary seal has a second cracking pressure different from the first cracking pressure; and a ventilation base member comprising a tubular portion coupled to the second end of the connector body portion and ventilator port, wherein the ventilator port comprises a conduit having a first conduit end and a second conduit end, wherein the first conduit end is coupled to the tubular portion through an articulable connection such that the ventilator port is articulable about the tubular portion in at least two axes.

In some embodiments, the first cracking pressure is less than the second cracking pressure.

In some embodiments, the first cracking pressure is within a range between 68 cm H2O and 188 cm H2O.

In some embodiments, the one or more first regions have a gradient thickness including a first thickness and a second thickness such that the second thickness is greater than the first thickness.

In some embodiments, the one or more second regions has a third thickness, greater than the second thickness of the one or more first regions.

In some embodiments, one or more of the plurality of valve segments further comprise one or more raised areas being thicker than the first thickness of the one or more first regions.

In some embodiments, the inner resiliently flexible diaphragm section comprises an arcuate cross-sectional biasing feature disposed proximal to the outer rim section, and wherein the arcuate cross-sectional biasing feature has an apex thickness less than the first thickness of the one or more first regions.

In some embodiments, the at least two axes of the articulable connection are offset by at least ten degrees.

In some embodiments, the articulable connection comprises a ball and socket connection.

In some embodiments, a closed suction catheter system includes a suction control valve assembly comprising: a housing having an interior cavity of the housing, a rigid tubular section coupled to the housing and having at least a portion of the rigid tubular section disposed within the interior cavity of the housing, the rigid tubular section having a first end, a second end, a pathway extending between the first end and the second end, and a pathway access opening arranged between the first end and the second end, an elastomeric valve member being coupled to and enclosing the pathway access opening of the rigid tubular section, and a pivotable actuator structure having a lever portion coupled to the elastomeric valve member; and a closed suction catheter sheath comprising a catheter and a flexible sleeve for enveloping the catheter, wherein the catheter is fixedly attached to the suction control valve assembly.

In some embodiments, the lever portion is configured to move along an arcuate path away from the pathway access opening so as to elastically deform the elastomeric valve member, wherein the rigid tubular section further comprises a pivot point mechanism disposed on an external surface, and wherein the pivotable actuator structure is coupled to the pivot point mechanism.

In some embodiments, the housing of the suction control valve assembly is generally ellipsoidal housing including one or more arcuate detents disposed along an external surface of the generally ellipsoidal housing.

In some embodiments, the suction catheter sheath further comprises a cord, having a cord length, embedded within a wall of the flexible sleeve, the cord being configured to limit axial elongation of the sleeve along the cord length, wherein the flexible sleeve has a first end, a second end, a first capture ring at the first end configured to be coupled to the catheter, and a second capture ring at the second end configured to be coupled to a suction catheter connector.

In some embodiments, the suction catheter connector is configured to be coupled to an artificial airway via a coupler, and wherein the coupler comprises transversely extending protrusions on an external surface.

In some embodiments, the cord has a length that is substantially the same length as the flexible sleeve.

In some embodiments, an exterior surface of the sleeve comprises texturing.

In some embodiments, the sleeve comprises two or more layers.

Some methods of using a closed suction catheter system include securing an airway adapter; advancing a suction catheter into an artificial airway of a patient through the airway adapter; and providing a depth indicator of the suction catheter via a lens disposed on the airway adapter.

Some methods further include providing a suction control valve comprising a generally ellipsoidal housing including one or more arcuate detents, an actuator structure including an actuator button having a top portion accessible via an opening of the housing, and a locking mechanism slidably movable along an exterior surface of the housing and configured to engage with the actuator structure; withdrawing the suction catheter from the artificial airway; and depressing the actuator button to cause suctioning of the suction catheter.

Some methods further include aligning a tip end of the suction catheter within an access zone of an airway adapter such that the tip end of the suction catheter is positioned between a valve and an airway adapter coupler, wherein the valve includes a plurality of valve segments configured to form a primary seal and a secondary seal, each of the primary and secondary seals providing a breachable seal between the access zone and a ventilation zone of the airway adapter, and wherein an end portion of a suction catheter assembly proximal to the tip end of the suction catheter is coupled to the access zone and includes a wiper seal with an access aperture configured to provide a slidably frictional fitting with the suction catheter; injecting a solution into a flush port of the airway adapter that is in fluid communication with the access zone; and depressing the actuator button to cause suctioning of the suction catheter, wherein a suction force applied by the suction catheter is sufficient to cause airflow from the ventilation zone into the access zone through the valve.

Some methods of using a closed suction closed suction catheter system include securing an airway adapter with a first hand of a caregiver; advancing a suction catheter into an artificial airway of the patient with a second hand of the caregiver; and viewing a depth indicator of the suction catheter via a lens disposed on the airway adapter.

Some methods further include grasping the suction control valve with the second hand of the caregiver, wherein the suction control valve comprises a generally ellipsoidal housing including one or more arcuate detents, an actuator structure including an actuator button having a top portion accessible via an opening of the housing, and a locking mechanism slidably movable along an exterior surface of the housing and configured to engage with the actuator structure; pulling the suction control valve away from the airway adapter to withdraw the suction catheter from the artificial airway; and depressing the actuator button with the thumb of the second hand to cause suctioning of the suction catheter.

Some methods further include aligning a tip end of the suction catheter within an access zone of an airway adapter such that the tip end of the suction catheter is positioned between a valve and an airway adapter coupler, wherein the valve includes a plurality of valve segments configured to form a primary seal and a secondary seal, each of the primary and secondary seals providing a breachable seal between the access zone and a ventilation zone of the airway adapter, and wherein an end portion of a suction catheter assembly proximal to the tip end of the suction catheter is coupled to the access zone and includes a wiper seal with an access aperture configured to provide a slidably frictional fitting with the suction catheter; injecting a solution into a flush port of the airway adapter that is in fluid communication with the access zone; and depressing the actuator button with the thumb of the second hand to cause suctioning of the suction catheter, wherein a suction force applied by the suction catheter is sufficient to cause airflow from the ventilation zone into the access zone through the valve.

It is understood that any specific order or hierarchy of blocks in the processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. An airway adapter assembly comprising:
   a connector body portion having an elongate cavity, extending between a first end and a second end of the connector body portion, and a flush port coupled to the elongate cavity between the first and second ends of the connector body portion;
   a ventilation base member comprising a tubular portion, extending between a first end and a second end of the ventilation base member, and a ventilator port, the ventilator port comprising a conduit having a first conduit end and a second conduit end, wherein the first conduit end is coupled to the tubular portion through an articulable connection such that the ventilator port is articulable about the tubular portion in at least two axes; and a valve coupled between the second end of the connector body and the first end of the ventilation base member, the valve comprising an outer rim section configured to engage with a valve retention structure and an inner resiliently flexible diaphragm section integrally connected to the outer rim section, the inner resiliently flexible diaphragm section comprising a plurality of valve segments defined by one or more slits, wherein one or more of the valve segments include one or more first regions and one or more second regions, wherein a primary seal is formed by the plurality of valve segments, and a secondary seal is formed by an arrangement of the one or more first regions of the one or more the valve segments, and wherein the secondary seal has a first cracking pressure, and the primary seal has a second cracking pressure different from the first cracking pressure; and wherein the primary seal is larger than the secondary seal such that the primary seal allows insertion of a medical implement to pass therethrough and the first cracking pressure of the secondary seal allows and regulates a small amount of air to pass therethrough.

2. The airway adapter assembly of claim 1, wherein the first cracking pressure is less than the second cracking pressure.

3. The airway adapter assembly of claim 1, wherein the first cracking pressure is within a range between 68 cm $H_2O$ and 188 cm $H_2O$.

4. The airway adapter assembly of claim 1, wherein the one or more first regions have a gradient thickness including a first thickness and a second thickness such that the second thickness is greater than the first thickness.

5. The airway adapter assembly of claim 4, wherein the one or more second regions having a third thickness, greater than the second thickness of the one or more first regions.

6. The airway adapter assembly of claim 4, wherein one or more of the plurality of valve segments further comprise one or more raised areas being thicker than the first thickness of the one or more first regions.

7. The airway adapter assembly of claim 4, wherein the inner resiliently flexible diaphragm section comprises an arcuate cross-sectional biasing feature disposed proximal to the outer rim section, and wherein the arcuate cross-sectional biasing feature has an apex thickness less than the first thickness of the one or more first regions.

8. The airway adapter assembly of claim 1, wherein the at least two axes of the articulable connection are offset by at least ten degrees.

9. The airway adapter assembly of claim 1, wherein the articulable connection comprises a ball and socket connection.

10. The airway adapter assembly of claim 1, wherein the plurality of valve segments extend radially inward from the outer rim section, and comprise a thickness that tapers between the outer rim section and an intersection of the plurality of valve segments.

11. The airway adapter assembly of claim 10, wherein the thickness of the plurality of valve segments tapers toward the intersection of the plurality of valve segments.

12. The airway adapter assembly of claim 10, wherein the thickness of the plurality of valve segments tapers along one or more slits.

13. The airway adapter assembly of claim 1, wherein the valve comprises a biasing portion extending between the outer rim section and the plurality of valve segments, wherein a thickness of the biasing portion is less than any of the outer rim section and the plurality of valve segments.

14. The airway adapter assembly of claim 1, wherein the elongate cavity comprises an axial center between the first and the second end, the axial center extending through the intersection of the plurality of valve segments.

* * * * *